United States Patent
Froehlich et al.

(10) Patent No.: US 10,619,147 B2
(45) Date of Patent: Apr. 14, 2020

(54) CHIMERIC POLYPEPTIDES HAVING XYLOSE ISOMERASE ACTIVITY

(71) Applicant: LALLEMAND HUNGARY LIQUIDITY MANAGEMENT LLC, Budapest (HU)

(72) Inventors: Allan Froehlich, Hartland, VT (US); Brooks Henningsen, Lebanon, NH (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 136 days.

(21) Appl. No.: 14/820,695

(22) Filed: Aug. 7, 2015

(65) Prior Publication Data

US 2016/0040152 A1    Feb. 11, 2016

Related U.S. Application Data

(60) Provisional application No. 62/035,752, filed on Aug. 11, 2014.

(51) Int. Cl.
| | | |
|---|---|---|
| *C12N 9/90* | (2006.01) | |
| *C12N 1/16* | (2006.01) | |
| *C12P 7/06* | (2006.01) | |
| *C12N 9/92* | (2006.01) | |
| *C12N 15/62* | (2006.01) | |

(52) U.S. Cl.
CPC ............... *C12N 9/92* (2013.01); *C12N 15/62* (2013.01); *C12P 7/06* (2013.01); *C12Y 503/01005* (2013.01); *Y02E 50/16* (2013.01); *Y02E 50/17* (2013.01)

(58) Field of Classification Search
CPC ............... C12N 9/90; C12N 1/15; C12N 1/19
See application file for complete search history.

(56) References Cited

U.S. PATENT DOCUMENTS

| | | |
|---|---|---|
| 2013/0004998 A1 | 1/2013 | Subbian et al. |
| 2014/0186930 A1 | 7/2014 | Argyros et al. |

FOREIGN PATENT DOCUMENTS

| | | |
|---|---|---|
| WO | 2012/097091 A2 | 7/2012 |
| WO | 2013/138339 A1 | 9/2013 |

OTHER PUBLICATIONS

[No Author Listed] "Xylose Isomerase From Thermotoga neapolitana," RCSB Protein Data Bank; http://www.rcsb.org/pdb/explore/explore.do?structureid=1AOE, 2 pages, deposited Nov. 28, 2011.
Bhosale, S. H., et al., "Molecular and industrial aspects of glucose isomerase," Microbiological Reviews, 1996, v. 60, pp. 280-300.
Chang, C., et al., "Crystal structures of thermostable xylose isomerases from Thermus caldophilus and Thermus thermophilus: possible structural determinants of thermostability," J. Mol. Biol., 1999, v. 288, pp. 623-634.
Demeke, M. M., et al., "Development of a D-xylose fermenting and inhibitor tolerant industrial *Saccharomyces cerevisiae* strain with high performance in lignocellulose hydrolysates using metabolic and evolutionary engineering," Biotechnol Biofuels. 2013; v. 6: pp. 1-24.
Gibson, D. G., et al., "Gibson Assembly®—Building a Synthetic Biology Toolset," https://www.neb.com/tools-and-resources/feature-articles/gibson-assembly-building-a-synthetic-biology-toolset; accessed Mar. 17, 2016. Published May 2012, 4 pages, copyright, New England Biolabs Inc.
Henrick, K., et al., "Structures of D-xylose isomerase from Arthrobacter strain B3728 containing the inhibitors xylitol and D-sorbitol at 2.5 A and 2.3 A resolution, respectively," J Mol. Biol. Jul. 5, 1989;208(1):129-57.
Invitation to Pay Additional Fees and Partial Search Report for Application No. PCT/IB2015/056104, dated Nov. 11, 2015 (7 pages).
International Search Report and Written Opinion for Application No. PCT/IB2015/056104, dated Jan. 21, 2016. (18 pages).
Meaden, P.G. et al., "The xylose isomerase-encoding gene (xylA) of Clostridium thermosaccharolyticum: cloning, sequencing and phylogeny of Xy1A enzymes," Gene, 1994, v. 141, pp. 97-101.
Nakamura, Y., et al.,"Codon Usage Tabulated from International DNA Sequence Databases: Status for the Year 2000," Nucl. Acids Res., 28:292, Oxford University Press, United Kingdom (2000).
Parachin, N. S. et al., "Isolation of xylose isomerases by sequence- and function-based screening from a soil metagenomic library," Biotechnology for Biofuels, 2011, v. 4, pp. 1-10.
Sharp, P.M. et al., "The codon adaptation index—a measure of directional synonymous codon usage bias, and its potential applications," Nucleic Acids Res. 15(3):1281-1295, IRL Press Limited, England (1987).
Vangrysperre, W. et al., "Localization of the essential histidine and carboxylate group in D-xylose isomerases," Biochem J. 1990; v. 265(3):pp. 699-705.

*Primary Examiner* — Maryam Monshipouri
(74) *Attorney, Agent, or Firm* — Nutter McClennen & Fish LLP

(57) ABSTRACT

There is provided chimeric polypeptides capable of converting xylose to xylulose, engineered host cells that express the chimeric polypeptides, methods of creating chimeric polypeptides, and methods of fermenting cellulosic biomass to produce biofuels, including ethanol.

6 Claims, 11 Drawing Sheets

Specification includes a Sequence Listing.

Figure 1: Schematic representation of xylose fermentation in genetically engineered *S. cerevisiae*
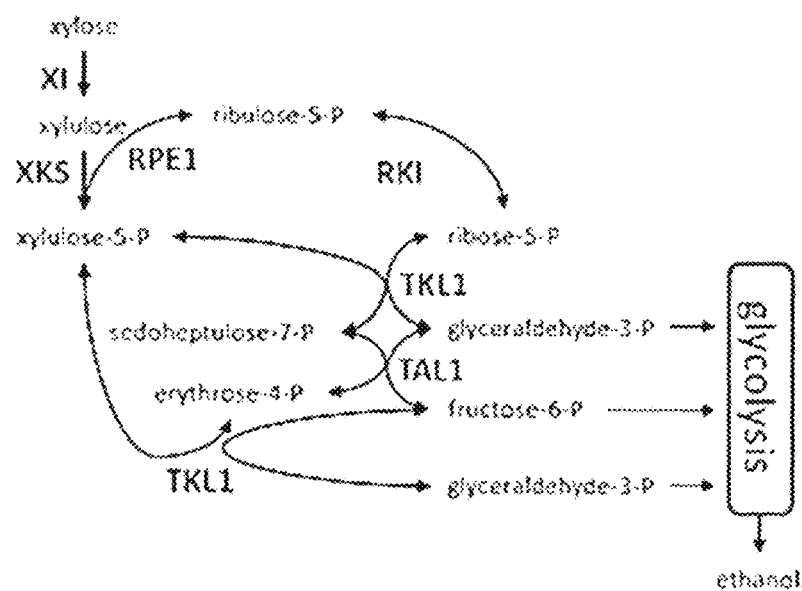

Figure 2: Vector Map of Vector Used in the XI Library
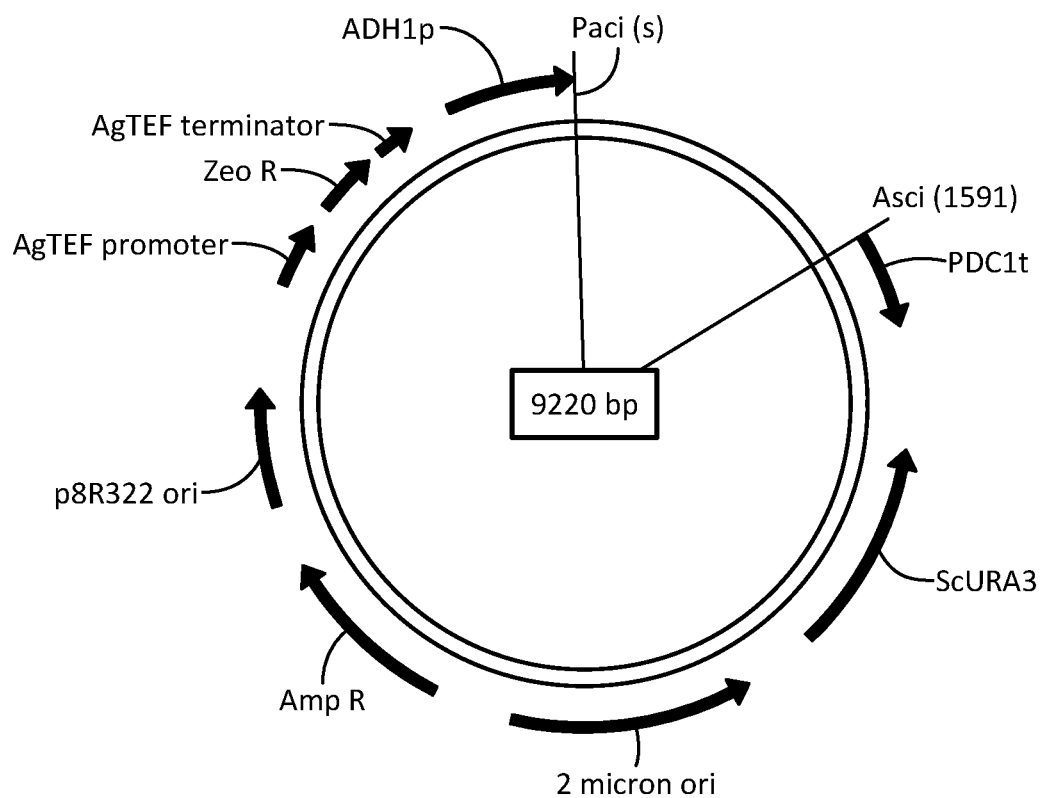

Figure 3: Chimeric XI library assembly
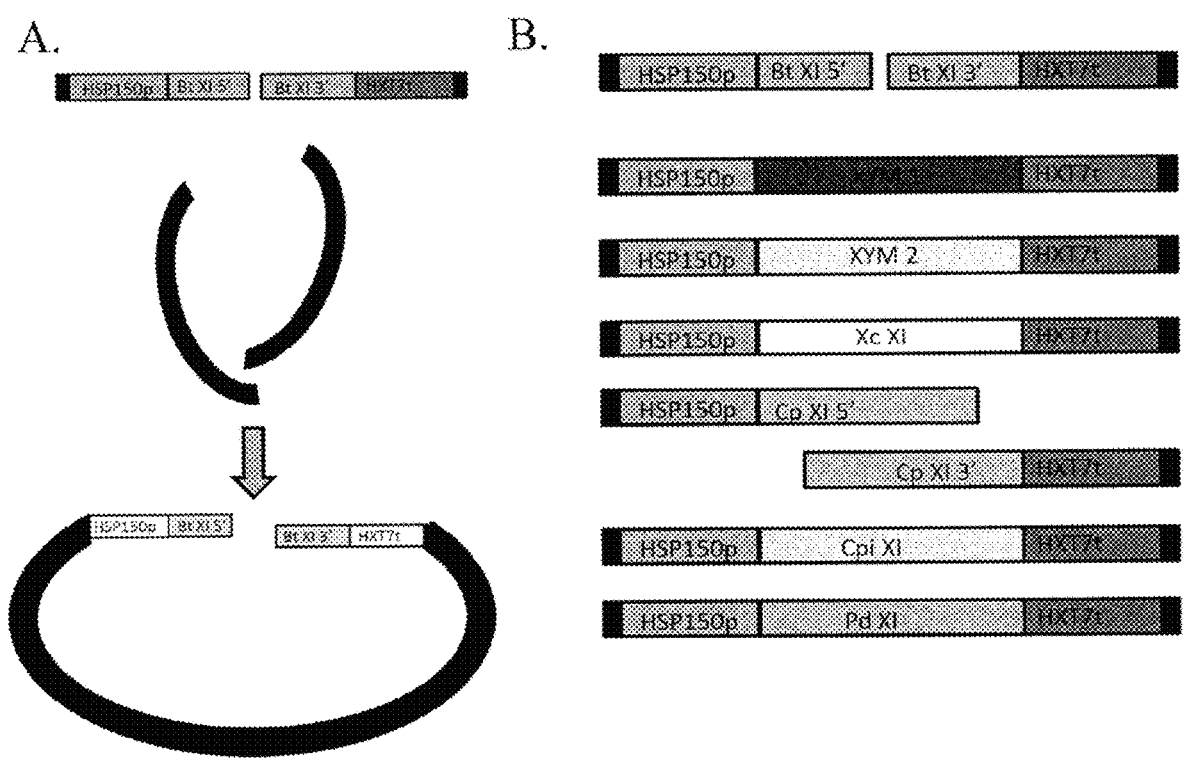

Figure 4: Schematic of XI fragments used in the chimeric XI library assembly
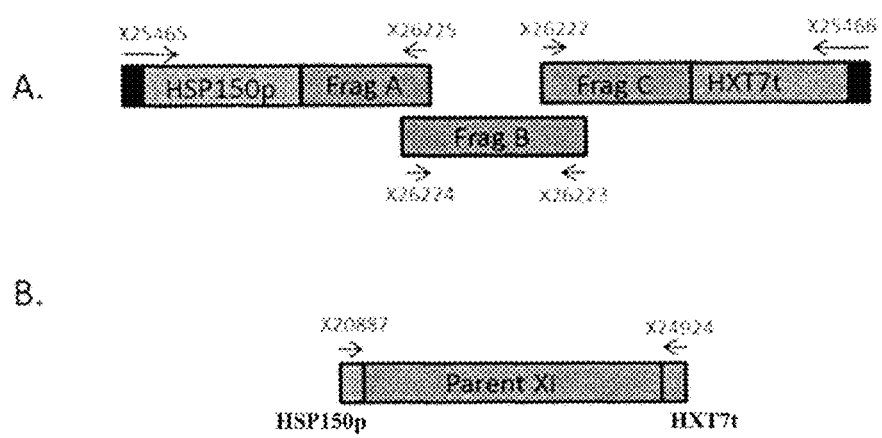

Figure 5: Schematic of homologous recombination to create chimeric polypeptides
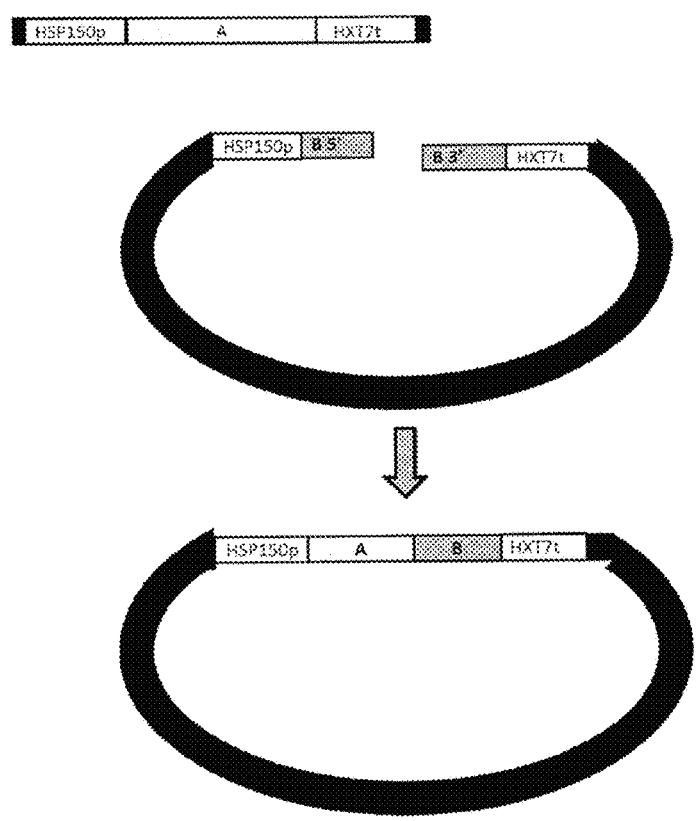

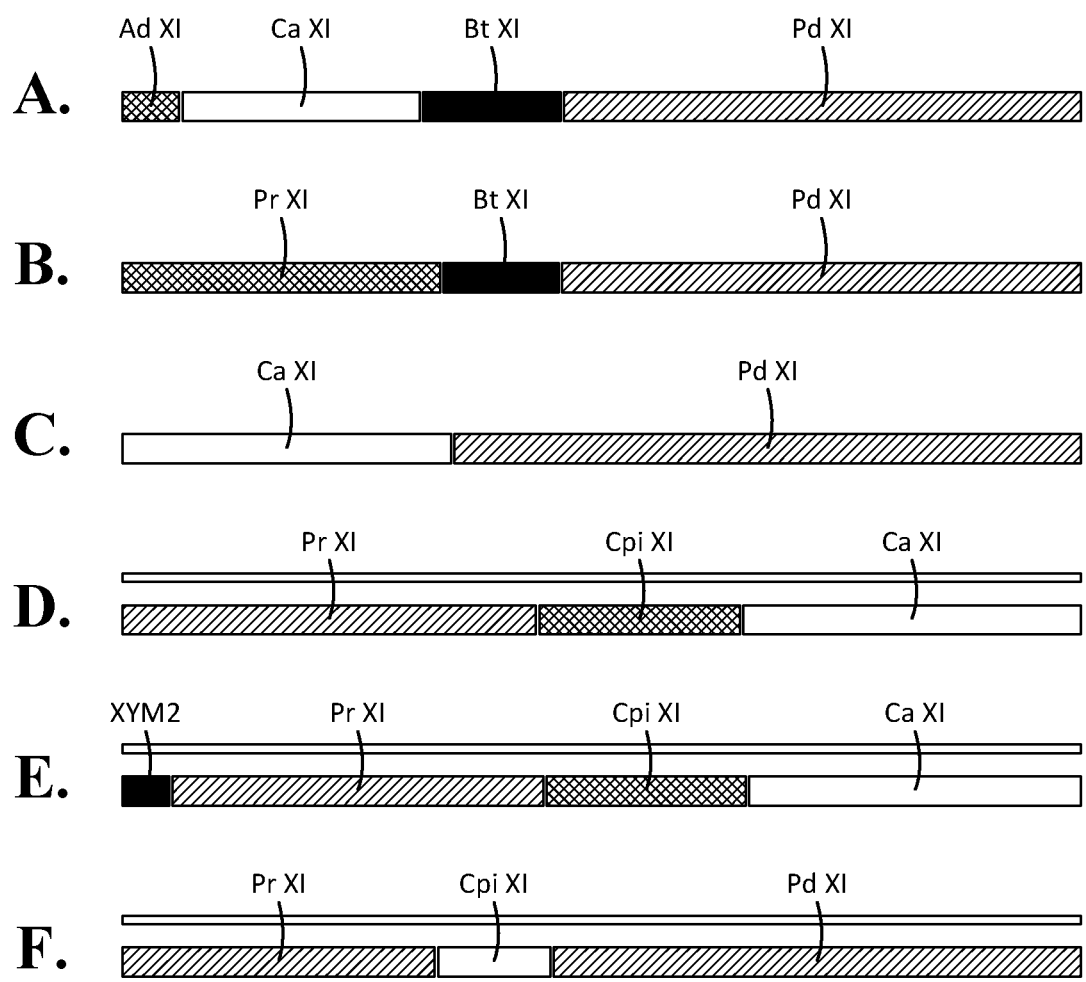
Figure 6: Schematic representations of chimeric XIs

Figure 7: Growth of strains on xylose media
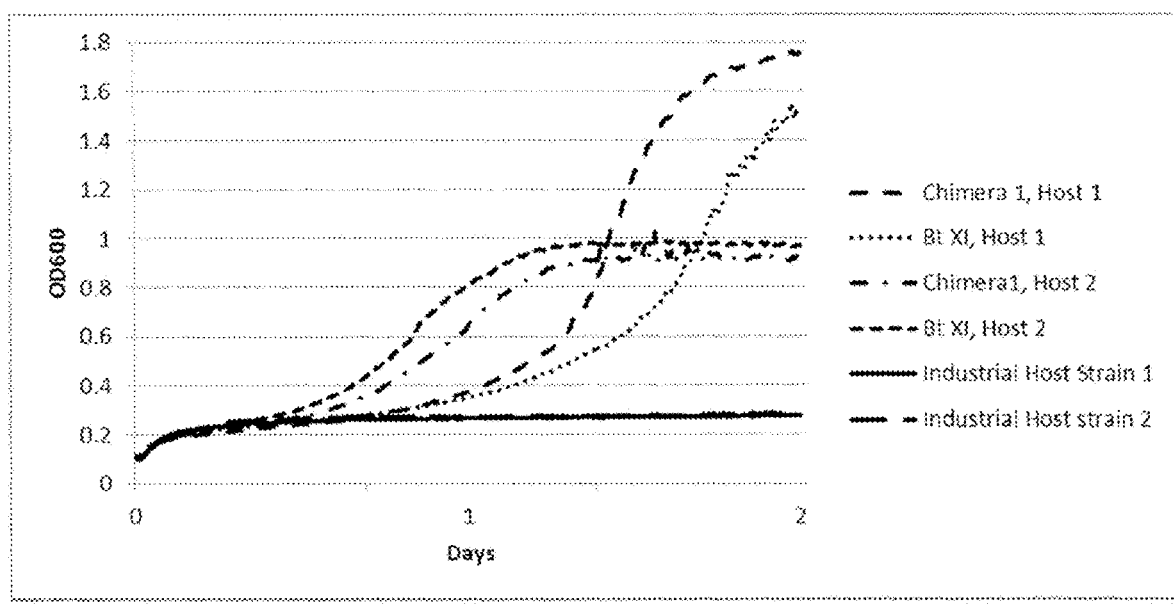

Figure 8a: Growth of strains on xylose media
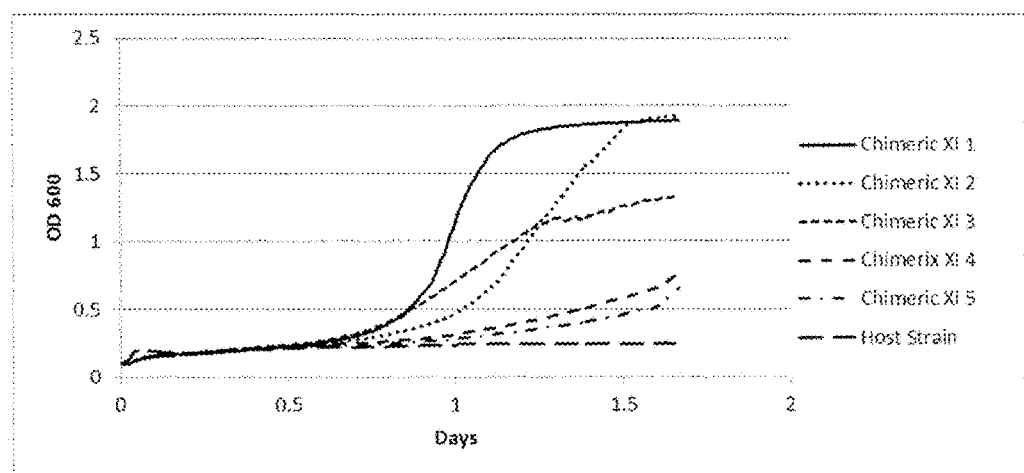
Figure 8B: Growth of Strains on xylose media
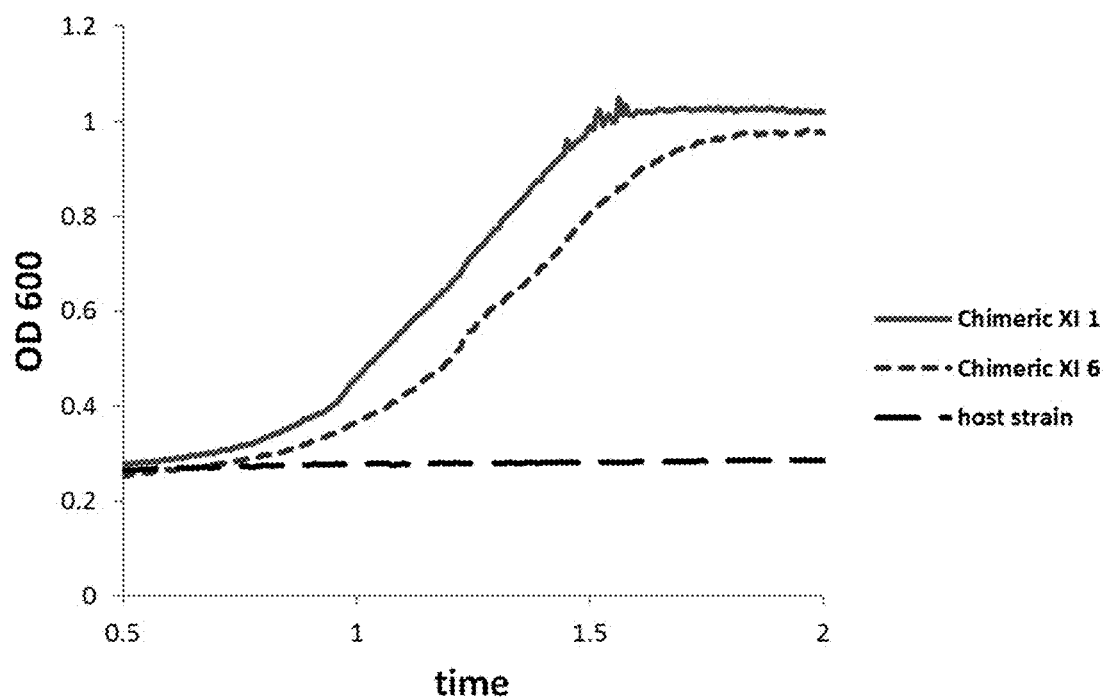

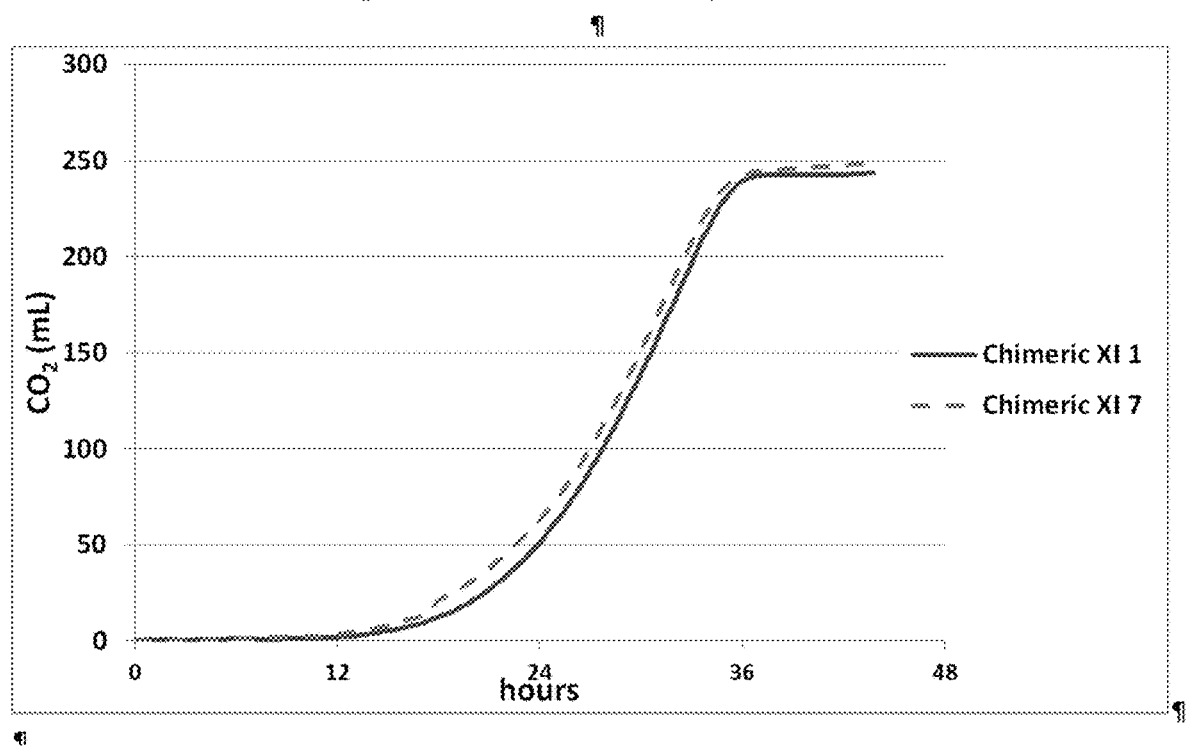

Figure 9: Ethanol production by *YPR1* deletion strains
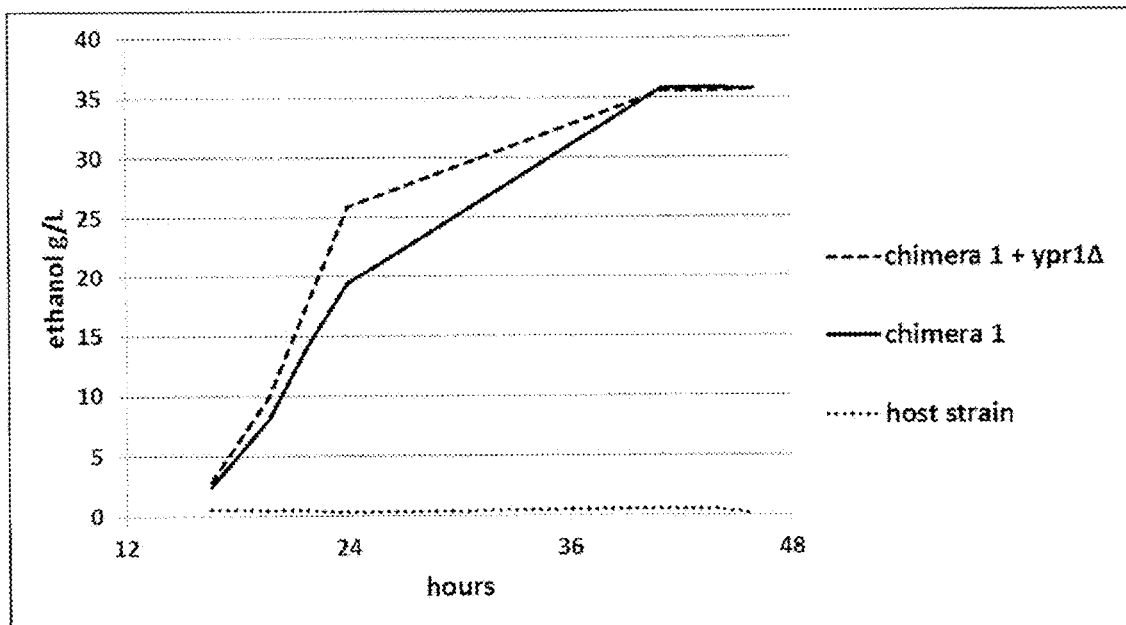

Figure 10: Growth of strains overexpressing *PGM1* on xylose media
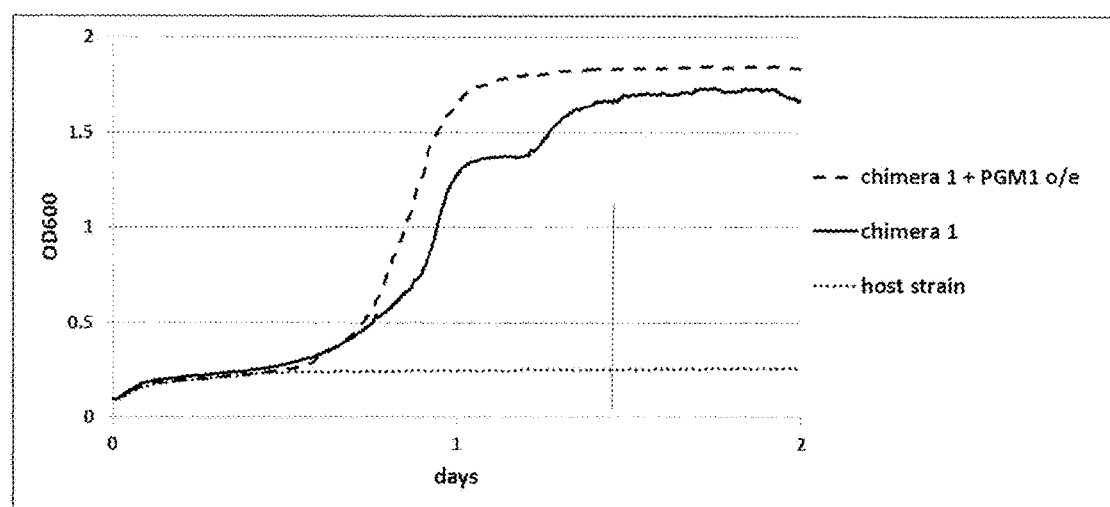

US 10,619,147 B2

CHIMERIC POLYPEPTIDES HAVING XYLOSE ISOMERASE ACTIVITY

CROSS-REFERENCE TO RELATED APPLICATION

This application claims priority from U.S. patent application Ser. No. 62/035,752 filed on Aug. 11, 2014, which is incorporated by reference in its entirety.

FEDERALLY SPONSORED RESEARCH OR DEVELOPMENT

This invention was funded, in part, by the Bioenergy Science Center, Oak Ridge National Laboratory, a U.S. Department of Energy Bioenergy Research Center supported by the Office of Biological and Environmental Research, under contract DE-P502-06ER64304. The government has certain rights in the invention.

REFERENCE TO SEQUENCE LISTING SUBMITTED ELECTRONICALLY VIA EFS-WEB

The content of the electronically submitted sequence listing (Name: 115235-192USSeqListUpdated.txt; Size: 79,958 bytes; Date of Creation: Aug. 7, 2015) is in accordance with 37 C.F.R. § 1.821-1.825, and is incorporated by reference in its entirety.

FIELD OF THE INVENTION

The field of the invention generally relates to chimeric polypeptides capable of converting xylose to xylulose, engineered host cells that express the chimeric polypeptide, methods of creating chimeric polypeptides, and methods of fermenting cellulosic biomass to produce biofuels, including ethanol.

BACKGROUND OF THE INVENTION

*Saccharomyces cerevisiae* is the primary biocatalyst used in the commercial production of "first generation" fuel ethanol from sugar based substrates such as corn, sugarcane, and sugarbeet. Second generation ethanol production, also known as cellulosic ethanol production, extends the carbohydrate source to more complex polysaccharides, such as cellulose and hemicellulose, which make up a significant portion of most plant cell walls and therefore most plant material.

Feedstocks commercially considered for second generation ethanol production include wood, agriculture residues such as corn stover and wheat straw, sugarcane bagasse and purpose grown materials such as switchgrass. The cellulose and hemicellulose must be hydrolyzed to monomeric sugars before fermentation using either mechanical/chemical means and/or enzymatic hydrolysis. The liberated monomeric sugars include glucose, xylose, galactose, mannose, and arabinose with glucose and xylose constituting more than 75% of the monomeric sugars in most feedstocks. For cellulosic ethanol production to be economically viable and compete with first generation ethanol, the biocatalyst must be able to convert the majority, if not all, of the available sugars into ethanol.

*S. cerevisiae* is the preferred organism for first generation ethanol production due to its robustness, high yield, and many years of safe use. However, naturally occurring *S. cerevisiae* is unable to ferment xylose into ethanol. For *S. cerevisiae* to be a viable biocatalyst for second generation ethanol production, it must be able to ferment xylose.

There are two metabolic pathways of xylose fermentation that have been demonstrated in *S. cerevisiae*. The pathways differ primarily in the conversion of xylose to xylulose. In the first pathway, the XR-XDH pathway, a xylose reductase (XR) converts xylose to xylitol, which is subsequently converted to xylulose by a xylitol dehydrogenase (XDH). The XR and XDH enzyme pairs tested to date differ in required cofactor, NADH and NADPH, leading to difficulties achieving redox balance. The second commonly tried pathway converts xylose directly to xylulose using a xylose isomerase (XI) with no redox cofactor requirements. XIs from both bacterial and fungal systems have been successfully utilized in *S. cerevisiae*. Both pathways utilize the same downstream metabolic engineering: up regulation of the native xylulose kinase (XKS1) and four genes of the pentose phosphate pathway, specifically ribulose-phosphate 3-epimerase (RPE1), ribose-5-phosphate ketol-isomerase (RKI1), transaldolase (TAL1), and transketolase (TKL1) (FIG. 1). Use of the XI pathway also commonly entails deletion of the native aldose reductase gene (GRE3) to eliminate product lost to xylitol formation.

BRIEF SUMMARY OF THE INVENTION

Aspects of the invention are directed to novel chimeric polypeptides capable of converting xylose directly to xylulose and methods of their creation and use are described herein. In some embodiments, the invention is directed to host cells that express one or more chimeric polypeptide.

In some embodiments of the present invention, the chimeric polypeptide has at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any one of SEQ ID NOs: 1, 3, 5, 7, and/or 9. In some embodiments, the chimeric polypeptide has an amino acid sequence of SEQ ID NOs: 1, 3, 5, 7, or 9.

In some embodiments of the present invention, the chimeric polypeptide has at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with SEQ ID NO: 25. In some embodiments, the chimeric polypeptide has an amino acid sequence of SEQ ID NO: 25.

In some embodiments of the present invention, the chimeric polypeptide has at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with SEQ ID NO: 27. In some embodiments, the chimeric polypeptide has an amino acid sequence of SEQ ID NO: 27.

In some embodiments, the chimeric polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any one of SEQ ID NOs: 2, 4, 6, 8, and/or 10. In some embodiments, the chimeric polypeptide is encoded by a polynucleotide sequence of SEQ ID NOs: 2, 4, 6, 8, or 10. In some embodiments, the polynucleotide sequence is contained in a vector.

In some embodiments, the chimeric polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with SEQ ID NO: 26. In some embodiments, the chimeric polypeptide is encoded by a polynucleotide sequence of SEQ ID NO: 26. In some embodiments, the polynucleotide sequence is contained in a vector.

In some embodiments, the chimeric polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with SEQ ID NO: 28. In some embodiments, the chimeric polypeptide is encoded by a polynucleotide sequence of SEQ ID NO: 28. In some embodiments, the polynucleotide sequence is contained in a vector.

In some aspects of the present invention, the chimeric polypeptide is created by combining two or more fragments from existing XIs. In some embodiments the donor XI sequences are isolated from nucleotide sequences from such as *Bacteroides thetaiotaomicron, Abiotrophia defectiva, Parabacteroides distasonis, Chitinophaga pinensis, Cyllamyces aberensis, Prevotella ruminicola*, and/or a related bacteria. In some embodiments, the nucleotide sequences are codon-optimized, e.g. for expression in yeast. In some embodiments, one or more of the donor XI sequences has a nucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any one of SEQ ID NOs: 12, 14, 16, 18, 20, 22, or 24. In some embodiments, one or more of the donor XI sequences has a nucleotide sequence of SEQ ID NOs: 12, 14, 16, 18, 20, 22, or 24. In some embodiments, at least one donor XI sequence has a nucleotide sequence encoding a polypeptide having an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any one of SEQ ID NOs: 11, 13, 15, 17, 19, 21, and/or 23. In some embodiments, at least one donor XI sequence has a nucleotide sequence encoding a polypeptide having an amino acid sequence of SEQ ID NOs: 11, 13, 15, 17, 19, 21, and/or 23.

In some embodiments the chimeric polypeptides are created by utilizing homologous recombination in yeast cells. In some embodiments, the chimeric polypeptides are created using *S. cerevisiae* cells. In some embodiments, the boundaries of the combined DNA fragments are not specifically chosen, but instead recombination of the fragments occurs in the yeast via its native homologous recombination machinery. In some embodiments, a chimeric XI can be identified and selected for by growing recombinant yeast cells on a medium having xylose as the only carbon source. In some embodiments, colonies capable of growing on xylose as the sole carbon source are selected and characterized as expressing a functional chimeric polypeptide capable of converting xylose to xylulose.

In some embodiments, the donor XI sequence encodes an XI polypeptide capable of conferring xylose isomerase activity onto a host cell, e.g. a *S. cerevisiae* cell. In some embodiments, the donor XI sequence encodes an XI polypeptide that is not capable of conferring xylose isomerase activity onto a host cell, e.g. a *S. cerevisiae* cell. In some embodiments, the chimeric polypeptide is comprised of at least two donor sequences, wherein at least one donor sequence encodes an XI capable of conferring xylose isomerase activity onto a host cell, e.g. a *S. cerevisiae* cell, and at least one donor sequence encodes an XI not capable of conferring xylose isomerase activity onto a host cell, e.g. a *S. cerevisiae* cell.

In some embodiments, a host cell is engineered to express one or more of the chimeric polypeptides. In some embodiments, the host cell is a yeast cell, e.g. a *S. cerevisiae* cell. In some embodiments the host cell is further modified to have mutations affecting at least one gene encoding a protein involved in the pentose phosphate pathway. In some embodiments, the host cell has at least one mutation that increases the expression or causes the up-regulation of XKS1, RKI1, RPE1, TKL1, and/or TAL1. In some embodiments, the host cell has a modification of one or more aldose reductase genes. In some embodiments, the aldose reductase gene is GRE3. In some embodiments, the host cell has a deletion or disruption of all or part of the endogenous GRE3 gene. In some embodiments, the aldose reductase gene is YPR1. In some embodiments, the host cell has a deletion or disruption of all or part of the endogenous YPR1 gene. In some embodiments, the host cell has a deletion or disruption of all or part of both the endogenous GRE3 gene and the endogenous YPR1 gene. In some embodiments, the host cell has a modification of PGM1 (phosphoglucomutase 1) and/or PGM2. In some embodiments, the host cell overexpresses PGM1 and/or PGM2. In some embodiments, the host cell has increased levels of Pgm1 and/or Pgm2 polypeptide and/or mRNA relative to a comparable host cell lacking a modification of PGM1 and/or PGM2.

In some embodiments, the host cell comprises a deletion or disruption of one or more endogenous enzymes that function to produce glycerol and/or regulate glycerol synthesis. In some embodiments, the host cell produces less glycerol than a control recombinant microorganism without deletion or disruption of said one or more endogenous enzymes that function to produce glycerol and/or regulate glycerol synthesis. In some embodiments, the one or more endogenous enzymes that function to produce glycerol are encoded by a GPD1 polynucleotide, a GPD2 polynucleotide, or both a GPD1 polynucleotide and a GPD2 polynucleotide. In some embodiments, one or both of the endogenous GPD1 and/or GPD2 genes are modified by mutation or deletion. In some embodiments, the host cell comprises a heterologous ADHE sequence. In some embodiments, the heterologous ADHE is from *Bifidobacterium adolescentis*. In some embodiments the native STL1 gene is upregulated by either modifying the promoter of the native copies or by introducing additional copies of STL1. In some embodiments the host cell comprises an ortholog of the native STL1. In some embodiments the native ACS2 gene is upregulated by either modifying the promoter of the native copies or by introducing additional copies of ACS2. In some embodiments, a yeast strain is used as the host cell. In some embodiments, the background of the yeast strain is an industrial yeast strain. One having ordinary skill in the art would be aware of many potential known yeast strains that can be modified according to the present invention, and this invention contemplates all such potential background yeast strains.

In some embodiments of the invention, the recombinant host cell is used to produce a fermentation product from a cellulosic or lignocellulosic material. In some embodiments, the fermentation product is ethanol, lactic acid, 3-hydroxypropionic acid, hydrogen, butyric acid, acrylic acid, acetic acid, succinic acid, citric acid, malic acid, fumaric acid, an amino acid, 1,3-propane-diol, ethylene, glycerol, acetone, isopropyl alcohol, butanol, a β-lactam, an antibiotic, a cephalosporin, or a combination thereof. In some embodiments, the cellulosic or lignocellulosic material is insoluble cellulose, crystalline cellulose, pretreated hardwood, paper sludge, pretreated corn stover, pretreated sugar cane bagasse, pretreated corn cobs, pretreated switchgrass, pretreated municipal solid waste, pretreated distiller's dried grains, pretreated wheat straw, corn fiber, agave, or a combination thereof.

In some embodiments, one or more of the chimeric polypeptides are purified. In some embodiments, the one or more chimeric polypeptides are purified from a recombinant yeast host cell of the invention, a composition of the invention, a media supernatant of the invention, or a yeast strain of the invention. In some embodiments, one or more chimeric polypeptides in the composition are from a crude extract. In some embodiments, the crude extract is from a recombinant yeast host cell of the invention, a composition of the invention, a media supernatant of the invention, or a yeast strain of the invention.

One aspect of the invention is directed to a composition comprising a lignocellulosic material and a recombinant yeast host cell comprising as least one chimeric polypeptide having xylose isomerase activity. Another aspect of the invention is directed to a media supernatant generated by incubating a recombinant yeast host comprising as least one chimeric polypeptide having xylose isomerase activity with a medium containing xylose as the only carbon source. In some embodiments, the medium comprises a cellulosic or lignocellulosic material. In some embodiments, the cellulosic or lignocellulosic material is insoluble cellulose, crystalline cellulose, pretreated hardwood, paper sludge, saw mill or paper mill discards, pretreated corn stover, pretreated sugar cane bagasse, pretreated corn cobs, pretreated switchgrass, pretreated municipal solid waste, pretreated distiller's dried grains, pretreated wheat straw, corn fiber, agave, or a combination thereof.

BRIEF DESCRIPTION OF THE DRAWINGS

FIG. 1 depicts a schematic representation of xylose fermentation in genetically engineered S. cerevisiae.

FIG. 2 depicts a schematic representation of the vector used to create the XI library.

FIG. 3 depicts a schematic representation of an example of the pieces used to assemble a chimeric XI library. FIG. 3A illustrates the process of assembling a vector backbone comprising 5' and 3' fragments of the B. thetaiotaomicron (Bt) XI coding sequence together with the yeast HSP150 promoter and HXT7 terminator regulatory elements. The vector does not contain the complete Bt XI sequence and therefore does not contain a functional XI and also cannot circularize via homologous recombination resulting in a linear non-replicating DNA fragment. The black bar representing the vector backbone would contain DNA sequences required for selection and replication of the plasmid in S. cerevisiae (e.g. 2 micron or CEN origin of replication, antibiotic selection marker such as ZEO) FIG. 3B provides representative drawings of individual examples of XI donor sequences to be recombined with the vector DNA depicted in FIG. 3A via yeast native homologous recombination resulting in a circular plasmid and in some cases a functional XI. The examples shown in FIG. 3 are not exhaustive of the XI donor sequence libraries contemplated or described herein.

FIG. 4 depicts a schematic representation of XI fragments used in the chimeric XI library assembly. FIG. 4A shows methodology and primers used for the amplification of functional parent XIs. FIG. 4B shows the methodology and primers used for the amplification of non-functional parent XIs.

FIG. 5 depicts a schematic representation of homologous recombination, creating chimeric polypeptide encoding sequences resulting from at least two donor sequences, designated here as "A" and "B". Solid black segments represent the vector backbone.

FIG. 6 depicts a schematic representation of example chimeric polypeptides having xylose isomerase activity created using the methods described herein. Figures A-E represent the chimeric polynucleotides having the nucleotide sequences represented by SEQ ID NOs: 2, 4, 6, 8, and 10 respectively, and the chimeric polypeptides having the amino acid sequences represented by SEQ ID NOs: 1, 3, 5, 7, and 9, respectively. Figure F represents the chimeric polynucleotides having the nucleotide sequences represented by SEQ ID NOs: 26 or 28, and the chimeric polypeptides having the amino acid sequences represented by SEQ ID NOs: 25 or 27.

FIG. 7 provides an example of the relative growth of yeast cells expressing a chimeric polypeptide having xylose isomerase activity, having an amino acid sequence of SEQ ID NO:1, on xylose as compared to B. thetaiotaomicron xylose isomerase, in two different host strains.

FIGS. 8A, B and C provide examples of the relative growth of yeast cells expressing various chimeric polypeptides having xylose isomerase activity, wherein the selected chimeric sequences are integrated within the xylose screening background. "Chimeric XI 1" refers to the chimeric XI represented by the amino acid sequence of SEQ ID NO:1, "Chimeric XI 2" refers to SEQ ID NO:3, "Chimeric XI 3" refers to SEQ ID NO:5, "Chimeric XI 4" refers to SEQ ID NO:7, "Chimeric XI 5" refers to SEQ ID NO:9, "Chimeric XI 6" refers to the chimeric XI represented by the amino acid sequence of SEQ ID NO:25, and "Chimeric XI 7" refers to the chimeric XI represented by the amino acid sequence of SEQ ID NO:7.

FIG. 9 provides an example of ethanol production by yeast cells expressing a chimeric polypeptide having xylose isomerase activity, having an amino acid sequence of SEQ ID NO:1, on xylose, wherein the cells optionally have a deletion of the endogenous YPR1 aldose reductase gene ("ypr1Δ").

FIG. 10 provides an example of the relative growth of yeast cells expressing a chimeric polypeptide having xylose isomerase activity, having an amino acid sequence of SEQ ID NO:1, on xylose, wherein the cells optionally over express ("o/e") PGM1.

DETAILED DESCRIPTION OF THE INVENTION

I. Definitions

Unless defined otherwise, all technical and scientific terms used herein have the same meaning as commonly understood to one of ordinary skill in the art of microbial metabolic engineering. Although methods and materials similar or equivalent to those described herein can be used in the practice of the disclosed methods and compositions, exemplary methods, devices and materials are described herein.

The embodiment(s) described, and references in the specification to "one embodiment", "an embodiment", "an example embodiment", etc., indicate that the embodiment(s) described can include a particular feature, structure, or characteristic, but every embodiment does not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

The description of "a" or "an" item herein refers to a single item or multiple items. It is understood that wherever embodiments are described herein with the language "comprising," otherwise analogous embodiments described in terms of "consisting of and/or "consisting essentially of are also provided. Thus, for example, reference to "a polynucleotide" includes a plurality of such polynucleotides and reference to "the microorganism" includes reference to one or more microorganisms, and so forth.

A "fragment" refers to any portion of a nucleic or amino acid sequence that is less than the entire sequence. A fragment of a nucleotide or an amino acid sequence can be any length of nucleotides or amino acids that is less than the entire length of the cited sequence and more than two nucleotides or amino acids in length. In some embodiments, the fragment can be from a donor sequence.

A "vector," e.g., a "plasmid" or "YAC" (yeast artificial chromosome) refers to an extrachromosomal element often carrying one or more genes that are not part of the central metabolism of the cell, and can be in the form of a linear or circular double-stranded DNA molecule. Vectors and plasmids can be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

An "expression vector" is a vector that is capable of directing the expression of genes to which it is operably associated.

The term "integrated" as used herein refers to genetic elements that are placed, through molecular biology techniques, into the genome of a host cell. For example, genetic elements can be placed into the chromosomes of the host cell as opposed to in a plasmid carried by the host cell. Methods for integrating genetic elements into the genome of a host cell are well known in the art and include homologous recombination. In some embodiments, more than one copy of the genetic elements are placed into the genome of a host cell. In some embodiments, 2, 3, 4, 5, 6, 7, 8, 9, 10, or more copies of the genetic elements are placed into the genome of a host cell.

The term "heterologous" when used in reference to a polynucleotide, a gene, a polypeptide, or an enzyme refers to a polynucleotide, gene, polypeptide, or an enzyme not normally found in the host organism. "Heterologous" also includes a native coding region, or portion thereof, that is removed from the source organism and subsequently reintroduced into the source organism in a form that is different from the corresponding native gene, e.g., not in its natural location in the organism's genome. The heterologous polynucleotide or gene can be introduced into the host organism by, e.g., gene transfer. A heterologous gene can include a native coding region that is a portion of a chimeric gene including non-native regulatory regions that is reintroduced into the native host. Foreign genes can comprise native genes inserted into a non-native organism, or chimeric genes. A heterologous polynucleotide, gene, polypeptide, or an enzyme can be derived from any source, e.g., eukaryotes, prokaryotes, viruses, or synthetic polynucleotide fragments. The term "heterologous" as used herein also refers to an element of a vector, plasmid or host cell that is derived from a source other than the endogenous source. Thus, for example, a heterologous sequence could be a sequence that is derived from a different gene or plasmid from the same host, from a different strain of host cell, or from an organism of a different taxonomic group (e.g., different kingdom, phylum, class, order, family, genus, or species, or any subgroup within one of these classifications). The term "heterologous" is also used synonymously herein with the term "exogenous." The term "heterologous expression" refers to the expression of a heterologous polynucleotide or gene by a host.

The term "domain" as used herein refers to a part of a molecule or structure that shares common physical or chemical features, for example hydrophobic, polar, globular, helical domains or properties, e.g., a DNA binding domain or an ATP binding domain. Domains can be identified by their homology to conserved structural or functional motifs. Examples of cellobiohydrolase (CBH) domains include the catalytic domain (CD) and the cellulose binding domain (CBD).

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which can be single-stranded or double-stranded. DNA includes cDNA, genomic DNA, synthetic DNA, and semi-synthetic DNA.

An "isolated nucleic acid molecule" or "isolated nucleic acid fragment" refers to the phosphate ester polymeric form of ribonucleosides (adenosine, guanosine, uridine, or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences are described herein according to the normal convention of giving only the sequence in the 5' to 3' direction along the non-transcribed strand of DNA (i.e., the strand having a sequence homologous to the mRNA).

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences. The terms "gene(s)" or "polynucleotide" or "nucleic acid" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. Also, the terms are intended to include a specific gene for a selected purpose. The gene can be endogenous to the host cell or can be recombinantly introduced into the host cell, e.g., as a plasmid maintained episomally or a plasmid (or fragment thereof) that is stably integrated into the genome. In addition to the plasmid form, a gene can, for example, be in the form of linear DNA or RNA. The term "gene" is also intended to refer to multiple copies of a particular gene, e.g., all of the DNA sequences in a cell encoding a particular gene product.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein (hereinafter "Maniatis", entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see, e.g., Maniatis at 9.50-9.51). For hybridizations with shorter nucleic acids, i.e., oligonucleotides, the position of mismatches becomes more important, and the length of the oligonucleotide determines its specificity (see, e.g., Maniatis, at 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration can be adjusted as necessary according to factors such as length of the probe.

As used herein the term "codon-optimized" means that a nucleic acid coding region has been adapted for expression in the cells of a given organism by replacing one, or more than one, or a significant number, of codons with one or more codons that are more frequently used in the genes of that organism.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case can be, as determined by the match between strings of such sequences.

As known in the art, "similarity" between two polypeptides is determined by comparing the amino acid sequence and conserved amino acid substitutes thereto of the polypeptide to the sequence of a second polypeptide. Similarity can be between two full sequences, or between a fragment of one sequence and a fragment of a second sequence wherein the fragments are of comparable length or size, or between a fragment of one sequence and the entirety of a second sequence.

"Identity" and "similarity" can be readily calculated by known methods, including but not limited to those described in: Computational Molecular Biology (Lesk, A. M, ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations can be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid sequences or fragments thereof (isolated polynucleotides of the present invention) encode polypeptides that are at least about 70% to about 75% identical to the amino acid sequences reported herein, at least about 80%, at least about 85%, at least about 86%, at least about 87%, at least about 88%, at least about 89%, or at least about 90% identical to the amino acid sequences reported herein, at least about 91%, at least about 92%, at least about 93%, at least about 94%, or at least about 95% identical to the amino acid sequences reported herein, or at least about 96%, at least about 97%, at least about 98%, at least about 99%, or about 100% identical to the amino acid sequences reported herein. Suitable nucleic acid fragments are at least about 50%, at least about 55%, at least about 60%, at least about 65%, at least about 70%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% identical to the nucleic acid sequences reported herein. Suitable nucleic acid fragments not only have the above identities/similarities but typically encode a polypeptide having at least 50 amino acids, at least 100 amino acids, at least 150 amino acids, at least 200 amino acids, or at least 250 amino acids.

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

An "isoform" is a protein that has the same function as another protein but which is encoded by a different gene and can have small differences in its sequence.

A "paralogue" is a protein encoded by a gene related by duplication within a genome.

An "orthologue" is gene from a different species that has evolved from a common ancestral gene by speciation. Normally, orthologues retain the same function in the course of evolution as the ancestral gene.

"Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

"Promoter" refers to a DNA fragment capable of controlling the expression of a coding sequence or functional RNA. In general, a coding region is located 3' to a promoter. Promoters can be isolated in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths can have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease SI), as well as protein binding domains (consensus sequences) responsible for the binding of RNA polymerase. Several promoters are specifically identified by the present invention, however, one having ordinary skill in the art would understand that any number of additional promoters capable of driving the expression in yeast would be included in the present invention.

The term "linker" as used herein refers to a series of nucleotides or amino acids that connect one section of the chimeric polynucleotide or polypeptide to another section of the chimeric polynucleotide of polypeptide. In some embodiments, the linker serves a structural function.

A coding region is "under the control" of transcriptional and translational control elements in a cell when RNA polymerase transcribes the coding region into mRNA, which is then trans-RNA spliced (if the coding region contains introns) and translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

As used herein the term "N-terminal region" refers to the portion of the amino acid sequence consisting of the most N-terminal amino acid residue up to the amino acid residue at position n/2, wherein n is the total number of residues in the sequence. As used herein the term "C-terminal region" refers to the portion of the amino acid sequence consisting of the most C-terminal amino acid residue up to the amino acid residue at position n/2, wherein n is the total number of residues in the sequence.

The term "operably associated" refers to the association of nucleic acid sequences on a single nucleic acid fragment so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation.

The term "expression," as used herein, refers to the transcription and stable accumulation of sense (mRNA) or antisense RNA derived from the nucleic acid fragment of the invention. Expression can also refer to translation of mRNA into a polypeptide.

The term "lignocellulose" refers to material that is comprised of lignin and cellulose. Examples of lignocelluloses are provided herein and are known in the art. Examples of lignocellulosic materials include but are not limited to corn stover, straw, bagasse, switchgrass, paper, and wood.

The "pentose phosphate pathway" or "PPP" refers to a biochemical pathway that creates NADPH from glucose-6-P. The PPP has both an oxidative phase and a non-oxidative phase. There are several enzymes that have been identified to play a role in the PPP, including but not limited to glucose-6-P dehydrogenase, gluconolactonase, 6-phosphogluconate dehydrogenase, ribulose-5-phosphate isomerase, ribose-5-phosphate ketol-isomerase (RKI1), ribulose-5-phosphate 3-epimerase (RPE1), transketolase (TKL1), and transaldolase (TAL1).

As used herein "xylose isomerase activity" refers to the ability of an enzyme to directly convert xylose to xylulose. A "xylose isomerase" or "XI" as used herein refers to a protein having xylose isomerase activity.

The term "chimeric" or "chimera" refers to a polynucleotide or polypeptide having a nucleotide or polypeptide sequence derived from two or more distinct parent sequences. A "parent sequence" or "donor sequence" is a nucleotide or amino acid sequence used as a source sequence to create the chimeric polynucleotide or polypeptide.

As used herein the term "XYM1" or "XYM2" refers to a xylose isomerase coding sequence or polypeptide isolated from an uncultured bacterium as described by Parachin and Gorwa-Grauslund, "Isolation of xylose isomerase by sequence- and function-based screening from a soil metagenome library," *Biotechnology Biofuels* 4(1):9 (2011).

As used herein, the term "anaerobic" refers to an organism, biochemical reaction, or process that is active or occurs under conditions of an absence of gaseous $O_2$.

"Anaerobic conditions" are defined as conditions under which the oxygen concentration in the fermentation medium is too low for the microorganism to use it as a terminal electron acceptor. Anaerobic conditions can be achieved by sparging a fermentation medium with an inert gas such as nitrogen until oxygen is no longer available to the microorganism as a terminal electron acceptor. Alternatively, anaerobic conditions can be achieved by the microorganism consuming the available oxygen of fermentation until oxygen is unavailable to the microorganism as a terminal electron acceptor.

"Aerobic metabolism" refers to a biochemical process in which oxygen is used as a terminal electron acceptor to convert energy, typically in the form of ATP, from carbohydrates. Aerobic metabolism typically occurs, for example, via the electron transport chain in mitochondria in eukaryotes, wherein a single glucose molecule is metabolized completely into carbon dioxide in the presence of oxygen.

In contrast, "anaerobic metabolism" refers to a biochemical process in which oxygen is not the final acceptor of electrons generated. Anaerobic metabolism can be divided into anaerobic respiration, in which compounds other than oxygen serve as the terminal electron acceptor, and substrate level phosphorylation, in which no exogenous electron acceptor is used and products of an intermediate oxidation state are generated via a "fermentative pathway."

In "fermentative pathways", the amount of NAD(P)H generated by glycolysis is balanced by the consumption of the same amount of NAD(P)H in subsequent steps. For example, in one of the fermentative pathways of certain yeast strains, NAD(P)H generated through glycolysis donates its electrons to acetaldehyde, yielding ethanol. Fermentative pathways are usually active under anaerobic conditions but can also occur under aerobic conditions, under conditions where NADH is not fully oxidized via the respiratory chain.

As used herein, the term "end-product" refers to a chemical compound that is not or cannot be used by a cell, and so is excreted or allowed to diffuse into the extracellular environment. Common examples of end-products from anaerobic fermentation include, but are not limited to, ethanol, acetic acid, formic acid, lactic acid, hydrogen, and carbon dioxide.

As used herein, "cofactors" are compounds involved in biochemical reactions that are recycled within the cells and remain at approximately steady state levels. Common examples of cofactors involved in anaerobic fermentation include, but are not limited to, $NAD^+$ and $NADP^+$. In metabolism, a cofactor can act in oxidation-reduction reactions to accept or donate electrons. When organic compounds are broken down by oxidation in metabolism, their energy can be transferred to $NAD^+$ by its reduction to NADH, to $NADP^+$ by its reduction to NADPH, or to another cofactor, $FAD^+$, by its reduction to $FADH_2$. The reduced cofactors can then be used as a substrate for a reductase.

As used herein, a "pathway" is a group of biochemical reactions that together can convert one compound into another compound in a step-wise process. A product of the first step in a pathway can be a substrate for the second step, and a product of the second step can be a substrate for the third, and so on. Pathways of the present invention include, but are not limited to, the pentose phosphate pathway, the xylose utilization pathway, the ethanol production pathway, and the glycerol production pathway. The term "recombination" or "recombinant" refers to the physical exchange of DNA between two identical (homologous), or nearly identical, DNA molecules. Recombination can be used for targeted gene deletion or to modify the sequence of a gene. The terms "recombinant microorganism" and "recombinant host cell" are used interchangeably herein and refer to microorganisms that have been genetically modified to express or over-express endogenous polynucleotides, or to express heterologous polynucleotides, such as those included in a vector, or which have a modification in expression of an endogenous gene.

By "expression modification" it is meant that the expression of the gene, or level of a RNA molecule or equivalent RNA molecules encoding one or more polypeptides or polypeptide subunits, or activity of one or more polypeptides or polypeptide subunits is up regulated or down-regulated, such that expression, level, or activity, is greater than or less than that observed in the absence of the modification.

In one aspect of the invention, genes or particular polynucleotide sequences are partially, substantially, or completely deleted, silenced, inactivated, or down-regulated in order to inactivate the enzymatic activity they encode. Complete deletions provide maximum stability because there is no opportunity for a reverse mutation to restore function. Alternatively, genes can be partially, substantially, or completely deleted, silenced, inactivated, or down-regulated by insertion, deletion, removal, or substitution of nucleic acid sequences that disrupt the function and/or expression of the gene.

II. Chimeric Polypeptides

The present invention provides polypeptides having xylose isomerase activity and the making and use thereof. In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any one of SEQ ID NOs: 1, 3, 5, 7, or 9. In some embodiments, the polypeptide has an amino acid sequence of SEQ ID NOs: 1, 3, 5, 7, or 9. In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with any one of SEQ ID NOs: 2, 4, 6, 8, and/or 10. In some embodiments, the polypeptide is encoded by a polynucleotide sequence of SEQ ID NOs: 2, 4, 6, 8, or 10.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with SEQ ID NO: 25. In some embodiments, the polypeptide has an amino acid sequence of SEQ ID NO: 25. In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with SEQ ID NO: 26. In some embodiments, the polypeptide is encoded by a polynucleotide sequence of SEQ ID NO: 26.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with SEQ ID NO: 27. In some embodiments, the polypeptide has an amino acid sequence of SEQ ID NO: 27. In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with SEQ ID NO: 28. In some embodiments, the polypeptide is encoded by a polynucleotide sequence of SEQ ID NO: 28.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 1. In some embodiments, the polypeptide has an amino acid sequence having 100% sequence identity with the amino acid sequence of SEQ ID NO: 1.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 3. In some embodiments, the polypeptide has an amino acid sequence having 100% sequence identity with the amino acid sequence of SEQ ID NO: 3.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 5. In some embodiments, the polypeptide has an amino acid sequence having 100% sequence identity with the amino acid sequence of SEQ ID NO: 5.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 7. In some embodiments, the polypeptide has an amino acid sequence having 100% sequence identity with the amino acid sequence of SEQ ID NO: 7.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 9. In some embodiments, the polypeptide has an amino acid sequence having 100% sequence identity with the amino acid sequence of SEQ ID NO: 9.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 25. In some embodiments, the polypeptide has an amino acid sequence having 100% sequence identity with the amino acid sequence of SEQ ID NO: 25.

In some embodiments, the polypeptide has an amino acid sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the amino acid sequence of SEQ ID NO: 27. In some embodiments, the polypeptide has an amino acid sequence having 100% sequence identity with the amino acid sequence of SEQ ID NO: 27.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 2. In some embodiments, the polypeptide is encoded by a polynucleotide sequence of SEQ ID NO: 2.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 4.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 6. In some embodiments, the polypeptide is encoded by a polynucleotide sequence of SEQ ID NO: 6.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 8. In some embodiments, the polypeptide is encoded by a polynucleotide sequence of SEQ ID NO: 8.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 10. In some embodiments, the polypeptide is encoded by a polynucleotide sequence of SEQ ID NO: 10.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 26. In some embodiments, the polypeptide is encoded by a polynucleotide sequence of SEQ ID NO: 26.

In some embodiments, the polypeptide is encoded by a polynucleotide sequence having at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the nucleotide sequence of SEQ ID NO: 28. In some embodiments, the polypeptide is encoded by a polynucleotide sequence of SEQ ID NO: 28.

In some embodiments, the C-terminal region of the polypeptide and the N-terminal region of the polypeptide comprise one or more fragments that share sequence homology with one or more donor sequences. In some embodiments, the fragment is between about 25 and about 275, between about 50 and about 275, between about 75 and about 275, between about 100 and about 275, between about 125 and about 275, between about 150 and about 275, between about 175 and about 275, between about 200 and about 275, between about 225 and about 275, between about 250 and about 275 amino acids in length. In some embodiments, the fragment is between about 25 and about 50, between about 25 and about 75, between about 25 and about 100, between about 25 and about 125, between about 25 and about 150, between about 25 and about 175, between about 25 and about 200, between about 25 and about 225, between about 25 and about 250 amino acids in length. In some embodiments, the fragment is between about 50 and about 250, between about 75 and about 225, between about 100 and about 200, between about 125 and about 175, between about 25 and about 100, between about 50 and about 125, between about 75 and about 150, between about 100 and about 175, between about 125 and about 200, between about 150 and about 225, between about 175 and about 250, between about 200 and about 275 amino acids in length. In some embodiments, the C-terminal fragment comprises the most C-terminal at least 25, at least 50, at least 75, at least 100, at least 125, at least 150, at least 175, at least 200, at least 225, at least 250, or at least 275 amino acids of the donor polypeptide. In some embodiments, the C-terminal fragment comprises at least 25, at least 50, at least 75, at least 100, at least 125, at least 150, at least 175, at least 200, at least 225, at least 250, or at least 275 amino acids but does not comprise the most C-terminal amino acid of the donor polypeptide. In some embodiments, the N-terminal fragment comprises the most N-terminal at least 25, at least 50, at least 75, at least 100, at least 125, at least 150, at least 175, at least 200, at least 225, at least 250, or at least 275 amino acids of the donor polypeptide. In some embodiments, the N-terminal fragment comprises at least 25, at least 50, at least 75, at least 100, at least 125, at least 150, at least 175, at least 200, at least 225, at least 250, or at least 275 amino acids but does not comprise the most N-terminal amino acid of the donor polypeptide.

In some embodiments, the C-terminal region of the polypeptide comprises at least 5, at least 10, at least 15, at least 20, at least 25, at least 30, at least 40, at least 45, or at least 50 contiguous amino acids from the amino acid sequence of SEQ ID NO: 13. In some embodiments, the polypeptide comprises residues 186-442 of SEQ ID NO: 13 or residues 142-442 of SEQ ID NO:13, wherein the positions in the polypeptide align with the positions in SEQ ID NO: 13. In some embodiments, a fragment of the C-terminal region of the polypeptide comprises an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identical to a comparably sized fragment of SEQ ID NO:13. In some embodiments, the C-terminal fragment of the polypeptide is at least 25, at least 50, at least 75, at least 100, at least 125, at least 150, at least 175, at least 200, at least 225, at least 250, or at least 275 amino acids in length.

In some embodiments, the C-terminal region of the polypeptide comprises at least 5, at least 10, at least 15, at least 20, at least 25, at least 30, at least 40, at least 45, or at least 50 contiguous amino acids from the amino acid sequence of SEQ ID NO: 15. In some embodiments, the polypeptide comprises residues 269-437 of SEQ ID NO: 15, wherein the positions in the polypeptide align with the positions in SEQ ID NO: 15. In some embodiments, a fragment of the C-terminal region of the polypeptide comprises an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identical to a comparably sized fragment of SEQ ID NO:15. In some embodiments, the C-terminal fragment of the polypeptide is at least 25, at least 50, at least 75, at least 100, at least 125, at least 150, or at least 169 amino acids in length.

In some embodiments, the C-terminal region of the polypeptide comprises at least 5, at least 10, at least 15, at least 20, at least 25, at least 30, at least 40, at least 45, or at least 50 contiguous amino acids from the amino acid sequence of SEQ ID NO: 21. In some embodiments, the polypeptide comprises residues 190-285 of SEQ ID NO: 21, wherein the positions in the polypeptide align with the positions in SEQ ID NO: 21. In some embodiments, a fragment of the C-terminal region of the polypeptide comprises an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identical to a comparably sized fragment of SEQ ID NO:21. In some embodiments, the C-terminal region of the fragment of the polypeptide having identity to SEQ ID NO:21 is at least 25, at least 50, at least 60, or at least 69 amino acids in length.

In some embodiments, the N-terminal region comprises at least 5, at least 10, at least 15, at least 20, at least 25, at least 30, at least 40, at least 45, at least 50, at least 60, or at least 66 contiguous amino acids from the amino acid sequence of SEQ ID NO: 11. In some embodiments, the polypeptide comprises residues 137-202 of SEQ ID NO: 11 or residues 134-202 of SEQ ID NO:11, wherein the positions in the polypeptide align with the positions in SEQ ID NO: 11. In some embodiments, a fragment of the N-terminal region of the polypeptide comprises an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identical to a comparably sized fragment of SEQ ID NO:11. In some embodiments, the N-terminal region fragment of the polypeptide is at least 25, at least 50, at least 66, or at least 69 amino acids in length.

In some embodiments, the N-terminal region comprises at least 5, at least 10, at least 15, at least 20, at least 25, at least 30, at least 40, at least 45, or at least 50 contiguous amino acids from the amino acid sequence of SEQ ID NO: 15. In some embodiments, the polypeptide comprises residues 1-155 or residues 24-140 of SEQ ID NO: 15, wherein the positions in the polypeptide align with the positions in SEQ ID NO: 15, wherein the positions in the polypeptide align with the positions in SEQ ID NO:15. In some embodiments, a fragment of the N-terminal region of the polypeptide comprises an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identical to a comparably sized fragment of SEQ ID NO:15. In some embodiments, the N-terminal fragment of the polypeptide is at least 25, at least 50, at least 75, at least 100, at least 117, at least 125, at least 150, or at least 155 amino acids in length.

In some embodiments, the N-terminal region comprises at least 5, at least 10, at least 15, at least 20, at least 25, at least 30, at least 40, at least 45, or at least 50 contiguous amino acids from the amino acid sequence of SEQ ID NO: 17. In some embodiments, the polypeptide comprises residues 1-31 of SEQ ID NO: 17, wherein the positions in the polypeptide align with the positions in SEQ ID NO: 17. In some embodiments, a fragment of the N-terminal region of the polypeptide comprises an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identical to a comparably sized fragment of SEQ ID NO:17.

In some embodiments, the N-terminal region comprises at least 5, at least 10, at least 15, at least 20, or at least 24 contiguous amino acids from the amino acid sequence of SEQ ID NO: 19. In some embodiments, the polypeptide comprises residues 1-24 of SEQ ID NO: 19, wherein the positions in the polypeptide align with the positions in SEQ ID NO: 19. In some embodiments, a fragment of the N-terminal region of the polypeptide comprises an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identical to a comparably sized fragment of SEQ ID NO:19. In some embodiments, the N-terminal fragment of the polypeptide is at least 10, at least 15, at least 20, at least 24 amino acids in length.

In some embodiments, the N-terminal region comprises at least 5, at least 10, at least 15, at least 20, at least 25, at least 30, at least 40, at least 45, or at least 50 contiguous amino acids from the amino acid sequence of SEQ ID NO: 21. In some embodiments, a fragment of the N-terminal region of the polypeptide comprises an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identical to a comparably sized fragment of SEQ ID NO:21.

In some embodiments, the N-terminal region comprises at least 5, at least 10, at least 15, at least 20, at least 25, at least 30, at least 40, at least 45, or at least 50 contiguous amino acids from the amino acid sequence of SEQ ID NO: 23. In some embodiments, the polypeptide comprises residues 1-197 of SEQ ID NO: 23 or residues 13-197 of SEQ ID NO: 23, wherein the positions in the polypeptide align with the positions in SEQ ID NO: 23. In some embodiments, a fragment of the N-terminal region of the polypeptide comprises an amino acid sequence that is at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% identical to a comparably sized fragment of SEQ ID NO:23. In some embodiments, the N-terminal fragment of the polypeptide is at least 25, at least 50, at least 75, at least 100, at least 125, at least 150, at least 175, at least 184, or at least 197 amino acids in length.

In some embodiments, the polypeptide comprises a C-terminal region and an N-terminal region, wherein the C-terminal region of the polypeptide comprises at least 5 contiguous amino acids from the amino acid sequence of SEQ ID NO:13 and the N-terminal region of the polypeptide comprises at least 5 contiguous amino acids from an amino acid sequence selected from the group consisting of SEQ ID NOs: 11, 15, 17, 23, and combinations thereof. In some embodiments, the polypeptide comprises a C-terminal region and an N-terminal region, wherein the C-terminal region of the polypeptide comprises at least 10 contiguous amino acids from the amino acid sequence of SEQ ID NO:13 and the N-terminal region of the polypeptide comprises at least 10 contiguous amino acids from an amino acid sequence selected from the group consisting of SEQ ID NOs: 11, 15, 17, 23, and combinations thereof. In some embodiments, the polypeptide comprises a C-terminal region and an N-terminal region, wherein the C-terminal region of the polypeptide comprises at least 15 contiguous amino acids from the amino acid sequence of SEQ ID NO:13 and the N-terminal region of the polypeptide comprises at least 15 contiguous amino acids from an amino acid sequence selected from the group consisting of SEQ ID NOs: 11, 15, 17, 23, and combinations thereof. In some embodiments, the polypeptide comprises a C-terminal region and an N-terminal region, wherein the C-terminal region of the polypeptide comprises at least 20 contiguous amino acids from the amino acid sequence of SEQ ID NO:13 and the N-terminal region of the polypeptide comprises at least 20 contiguous amino acids from an amino acid sequence selected from the group consisting of SEQ ID NOs: 11, 15, 17, 23, and combinations thereof.

In some embodiments, the polypeptide comprises a C-terminal region and an N-terminal region, wherein the C-terminal region comprises at least 5 contiguous amino acids from the amino acid sequence of SEQ ID NO:15 and the N-terminal region comprises at least 5 contiguous amino acids from an amino acid sequence selected from the group consisting of SEQ ID NOs: 19, 21, 23, and combinations thereof. In some embodiments, the polypeptide comprises a C-terminal region and an N-terminal region, wherein the C-terminal region comprises at least 10 contiguous amino acids from the amino acid sequence of SEQ ID NO:15 and the N-terminal region comprises at least 10 contiguous amino acids from an amino acid sequence selected from the group consisting of SEQ ID NOs: 19, 21, 23, and combinations thereof. In some embodiments, the polypeptide comprises a C-terminal region and an N-terminal region, wherein the C-terminal region comprises at least 15 contiguous amino acids from the amino acid sequence of SEQ ID NO:15 and the N-terminal region comprises at least 15 contiguous amino acids from an amino acid sequence selected from the group consisting of SEQ ID NOs: 19, 21, 23, and combinations thereof. In some embodiments, the polypeptide comprises a C-terminal region and an N-terminal region, wherein the C-terminal region comprises at least 20 contiguous amino acids from the amino acid sequence of SEQ ID NO:15 and the N-terminal region comprises at least 20 contiguous amino acids from an amino acid sequence selected from the group consisting of SEQ ID NOs: 19, 21, 23, and combinations thereof.

In some embodiments, the polypeptide comprises an amino acid sequence wherein a fragment thereof has at least 90% sequence identity with a comparably sized fragment of SEQ ID NO:11, a second fragment thereof has at least 90% identity with a comparably sized fragment of SEQ ID NO:13, and a third fragment thereof has at least 90% identity with a comparably sized fragment of SEQ ID NO:23. In some embodiments, the polypeptide comprises an amino acid sequence wherein a fragment thereof has at least 91% sequence identity with a comparably sized fragment of SEQ ID NO:11, a second fragment thereof has at least 91% identity with a comparably sized fragment of SEQ ID NO:13, and a third fragment thereof has at least 91% identity with a comparably sized fragment of SEQ ID NO:23. In some embodiments, the polypeptide comprises an amino acid sequence wherein a fragment thereof has at least 92% sequence identity with a comparably sized fragment of SEQ ID NO:11, a second fragment thereof has at least 92% identity with a comparably sized fragment of SEQ ID NO:13, and a third fragment thereof has at least 92% identity with a comparably sized fragment of SEQ ID NO:23. In some embodiments, the polypeptide comprises an amino acid sequence wherein a fragment thereof has at least 93% sequence identity with a comparably sized fragment of SEQ ID NO:11, a second fragment thereof has at least 93% identity with a comparably sized fragment of SEQ ID NO:13, and a third fragment thereof has at least 93% identity with a comparably sized fragment of SEQ ID NO:23. In some embodiments, the polypeptide comprises an amino acid sequence wherein a fragment thereof has at least 94% sequence identity with a comparably sized fragment of SEQ ID NO:11, a second fragment thereof has at least 94% identity with a comparably sized fragment of SEQ ID NO:13, and a third fragment thereof has at least 94% identity with a comparably sized fragment of SEQ ID NO:23. In some embodiments, the polypeptide comprises an amino acid sequence wherein a fragment thereof has at least 95% sequence identity with a comparably sized fragment of SEQ ID NO:11, a second fragment thereof has at least 95% identity with a comparably sized fragment of SEQ ID NO:13, and a third fragment thereof has at least 95% identity with a comparably sized fragment of SEQ ID NO:23. In some embodiments, the polypeptide comprises an amino acid sequence wherein a fragment thereof has at least 96% sequence identity with a comparably sized fragment of SEQ ID NO:11, a second fragment thereof has at least 96% identity with a comparably sized fragment of SEQ ID NO:13, and a third fragment thereof has at least 96% identity with a comparably sized fragment of SEQ ID NO:23. In some embodiments, the polypeptide comprises an amino acid sequence wherein a fragment thereof has at least 97% sequence identity with a comparably sized fragment of SEQ ID NO:11, a second fragment thereof has at least 97% identity with a comparably sized fragment of SEQ ID NO:13, and a third fragment thereof has at least 97% identity with a comparably sized fragment of SEQ ID NO:23. In some embodiments, the polypeptide comprises an amino acid sequence wherein a fragment thereof has at least 98% sequence identity with a comparably sized fragment of SEQ ID NO:11, a second fragment thereof has at least 98% identity with a comparably sized fragment of SEQ ID NO:13, and a third fragment thereof has at least 98% identity with a comparably sized fragment of SEQ ID NO:23. In some embodiments, the polypeptide comprises an amino acid sequence wherein a fragment thereof has at least 99% sequence identity with a comparably sized fragment of SEQ ID NO:11, a second fragment thereof has at least 99% identity with a comparably sized fragment of SEQ ID NO:13, and a third fragment thereof has at least 99% identity with a comparably sized fragment of SEQ ID NO:23. In some embodiments, the polypeptide comprises an amino acid sequence wherein a fragment thereof has 100% sequence identity with a comparably sized fragment of SEQ ID NO:11, a second fragment thereof has at least 100% identity with a comparably sized fragment of SEQ ID NO:13, and a third fragment thereof has at least 100% identity with a comparably sized fragment of SEQ ID NO:23.

In some embodiments, the polypeptide comprises an amino acid sequence wherein a fragment thereof has at least 90% sequence identity with a comparably sized fragment of SEQ ID NO:11, a second fragment thereof has at least 90% identity with a comparably sized fragment of SEQ ID NO:13, a third fragment thereof has at least 90% identity with a comparably sized fragment of SEQ ID NO:15, and a fourth fragment thereof has at least 90% identity with SEQ ID NO:17. In some embodiments, the polypeptide comprises an amino acid sequence wherein a fragment thereof has at least 91% sequence identity with a comparably sized fragment of SEQ ID NO:11, a second fragment thereof has at least 91% identity with a comparably sized fragment of SEQ ID NO:13, a third fragment thereof has at least 91% identity with a comparably sized fragment of SEQ ID NO:15, and a fourth fragment thereof has at least 91% identity with a comparably sized fragment of SEQ ID NO:17. In some embodiments, the polypeptide comprises an amino acid sequence wherein a fragment thereof has at least 92% sequence identity with a comparably sized fragment of SEQ ID NO:11, a second fragment thereof has at least 92% identity with a comparably sized fragment of SEQ ID NO:13, a third fragment thereof has at least 92% identity with a comparably sized fragment of SEQ ID NO:15, and a fourth fragment thereof has at least 92% identity with a comparably sized fragment of SEQ ID NO:17. In some embodiments, the polypeptide comprises an amino acid sequence wherein a fragment thereof has at least 93% sequence identity with a comparably long fragment of SEQ ID NO:11, a second fragment thereof has at least 93% identity with a comparably long fragment of SEQ ID NO:13, a third fragment thereof has at least 93% identity with a comparably long fragment of SEQ ID NO:15, and a fourth fragment thereof has at least 93% identity with a comparably long fragment of SEQ ID NO:17. In some embodiments, the polypeptide comprises an amino acid sequence wherein a fragment thereof has at least 94% sequence identity with a comparably sized fragment of SEQ ID NO:11, a second fragment thereof has at least 94% identity with a comparably sized fragment of SEQ ID NO:13, a third fragment thereof has at least 94% identity with a comparably sized fragment of SEQ ID NO:15, and a fourth fragment thereof has at least 94% identity with a comparably sized fragment of SEQ ID NO:17. In some embodiments, the polypeptide comprises an amino acid sequence wherein a fragment thereof has at least 95% sequence identity with a comparably sized fragment of SEQ ID NO:11, a second fragment thereof has at least 95% identity with a comparably sized fragment of SEQ ID NO:13, a third fragment thereof has at least 95% identity with a comparably sized fragment of SEQ ID NO:15, and a fourth fragment thereof has at least 95% identity with a comparably sized fragment of SEQ ID NO:17. In some embodiments, the polypeptide comprises an amino acid sequence wherein a fragment thereof has at least 96% sequence identity with a comparably sized fragment of SEQ ID NO:11, a second fragment thereof has at least 96% identity with a comparably sized fragment of SEQ ID NO:13, a third fragment thereof has at least 96% identity with a comparably sized fragment of SEQ ID NO:15, and a fourth fragment thereof has at least 96% identity with a comparably sized fragment of SEQ ID NO:17. In some embodiments, the polypeptide comprises an amino acid sequence wherein a fragment thereof has at least 97% sequence identity with a comparably sized fragment of SEQ ID NO:11, a second fragment thereof has at least 97% identity with a comparably sized fragment of SEQ ID NO:13, a third fragment thereof has at least 97% identity with a comparably sized fragment of SEQ ID NO:15, and a fourth fragment thereof has at least 97% identity with a comparably sized fragment of SEQ ID NO:17. In some embodiments, the polypeptide comprises an amino acid sequence wherein a fragment thereof has at least 98% sequence identity with a comparably sized fragment of SEQ ID NO:11, a second fragment thereof has at least 98% identity with a comparably sized fragment of SEQ ID NO:13, a third fragment thereof has at least 98% identity with a comparably sized fragment of SEQ ID NO:15, and a fourth fragment thereof has at least 98% identity with a comparably sized fragment of SEQ ID NO:17. In some embodiments, the polypeptide comprises an amino acid sequence wherein a fragment thereof has at least 99% sequence identity with a comparably sized fragment of SEQ ID NO:11, a second fragment thereof has at least 99% identity with a comparably sized fragment of SEQ ID NO:13, a third fragment thereof has at least 99% identity with a comparably sized fragment of SEQ ID NO:15, and a fourth fragment thereof has at least 99% identity with a comparably sized fragment of SEQ ID NO:17. In some embodiments, the polypeptide comprises an amino acid sequence wherein a fragment thereof has 100% sequence identity with a comparably sized fragment of SEQ ID NO:11, a second fragment thereof has 100% identity with a comparably sized fragment of SEQ ID NO:13, a third fragment thereof has 100% identity with a comparably sized fragment of SEQ ID NO:15, and a fourth fragment thereof has 100% identity with a comparably sized fragment of SEQ ID NO:17.

In some embodiments, the polypeptide comprises an amino acid sequence wherein a fragment thereof has at least 90% sequence identity with a comparably sized fragment of SEQ ID NO:13 and a second fragment thereof has at least 90% identity with a comparably sized fragment of SEQ ID NO:15. In some embodiments, the polypeptide comprises an amino acid sequence wherein a fragment thereof has at least 91% sequence identity with a comparably sized fragment of SEQ ID NO:13 and a second fragment thereof has at least 91% identity with a comparably sized fragment of SEQ ID NO:15. In some embodiments, the polypeptide comprises an amino acid sequence wherein a fragment thereof has at least 92% sequence identity with a comparably sized fragment of SEQ ID NO:13 and a second fragment thereof has at least 92% identity with a comparably sized fragment of SEQ ID NO:15. In some embodiments, the polypeptide comprises an amino acid sequence wherein a fragment thereof has at least 93% sequence identity with a comparably sized fragment of SEQ ID NO:13 and a second fragment thereof has at least 93% identity with a comparably sized fragment of SEQ ID NO:15. In some embodiments, the polypeptide comprises an amino acid sequence wherein a fragment thereof has at least 94% sequence identity with a comparably sized fragment of SEQ ID NO:13 and a second fragment thereof has at least 94% identity with a comparably sized fragment of SEQ ID NO:15. In some embodiments, the polypeptide comprises an amino acid sequence wherein a fragment thereof has at least 95% sequence identity with a comparably sized fragment of SEQ ID NO:13 and a second fragment thereof has at least 95% identity with a comparably sized fragment of SEQ ID NO:15. In some embodiments, the polypeptide comprises an amino acid sequence wherein a fragment thereof has at least 96% sequence identity with a comparably sized fragment of SEQ ID NO:13 and a second fragment thereof has at least 96% identity with a comparably sized fragment of SEQ ID NO:15. In some embodiments, the polypeptide comprises an amino acid sequence wherein a fragment thereof has at least 97% sequence identity with a comparably sized fragment of SEQ ID NO:13 and a second fragment thereof has at least 97% identity with a comparably sized fragment of SEQ ID NO:15. In some embodiments, the polypeptide comprises an amino acid sequence wherein a fragment thereof has at least 98% sequence identity with a comparably sized fragment of SEQ ID NO:13 and a second fragment thereof has at least 98% identity with a comparably sized fragment of SEQ ID NO:15. In some embodiments, the polypeptide comprises an amino acid sequence wherein a fragment thereof has at least 99% sequence identity with a comparably sized fragment of SEQ ID NO:13 and a second fragment thereof has at least 99% identity with a comparably sized fragment of SEQ ID NO:15. In some embodiments, the polypeptide comprises an amino acid sequence wherein a fragment thereof has 100% sequence identity with a comparably sized fragment of SEQ ID NO:13 and a second fragment thereof has 100% identity with a comparably sized fragment of SEQ ID NO:15.

In some embodiments, the polypeptide comprises an amino acid sequence wherein a fragment thereof has at least 90% sequence identity with a comparably sized fragment of SEQ ID NO:15, a second fragment thereof has at least 90% identity with a comparably sized fragment of SEQ ID NO:21, and a third fragment thereof has at least 90% identity with a comparably sized fragment of SEQ ID NO:23. In some embodiments, the polypeptide comprises an amino acid sequence wherein a fragment thereof has at least 91% sequence identity with a comparably sized fragment of SEQ ID NO:15, a second fragment thereof has at least 91% identity with a comparably sized fragment of SEQ ID NO:21, and a third fragment thereof has at least 91% identity with a comparably sized fragment of SEQ ID NO:23. In some embodiments, the polypeptide comprises an amino acid sequence wherein a fragment thereof has at least 92% sequence identity with a comparably sized fragment of SEQ ID NO:15, a second fragment thereof has at least 92% identity with a comparably sized fragment of SEQ ID NO:21, and a third fragment thereof has at least 92% identity with a comparably sized fragment of SEQ ID NO:23. In some embodiments, the polypeptide comprises an amino acid sequence wherein a fragment thereof has at least 93% sequence identity with a comparably sized fragment of SEQ ID NO:15, a second fragment thereof has at least 93% identity with a comparably sized fragment of SEQ ID NO:21, and a third fragment thereof has at least 93% identity with a comparably sized fragment of SEQ ID NO:23. In some embodiments, the polypeptide comprises an amino acid sequence wherein a fragment thereof has at least 94% sequence identity with a comparably sized fragment of SEQ ID NO:15, a second fragment thereof has at least 94% identity with a comparably sized fragment of SEQ ID NO:21, and a third fragment thereof has at least 94% identity with a comparably sized fragment of SEQ ID NO:23. In some embodiments, the polypeptide comprises an amino acid sequence wherein a fragment thereof has at least 95% sequence identity with a comparably sized fragment of SEQ ID NO:15, a second fragment thereof has at least 95% identity with a comparably sized fragment of SEQ ID NO:21, and a third fragment thereof has at least 95% identity with a comparably sized fragment of SEQ ID NO:23. In some embodiments, the polypeptide comprises an amino acid sequence wherein a fragment thereof has at least 96% sequence identity with a comparably sized fragment of SEQ ID NO:15, a second fragment thereof has at least 96% identity with a comparably sized fragment of SEQ ID NO:21, and a third fragment thereof has at least 96% identity with a comparably sized fragment of SEQ ID NO:23. In some embodiments, the polypeptide comprises an amino acid sequence wherein a fragment thereof has at least 97% sequence identity with a comparably sized fragment of SEQ ID NO:15, a second fragment thereof has at least 97% identity with a comparably sized fragment of SEQ ID NO:21, and a third fragment thereof has at least 97% identity with a comparably sized fragment of SEQ ID NO:23. In some embodiments, the polypeptide comprises an amino acid sequence wherein a fragment thereof has at least 98% sequence identity with a comparably sized fragment of SEQ ID NO:15, a second fragment thereof has at least 98% identity with a comparably sized fragment of SEQ ID NO:21, and a third fragment thereof has at least 98% identity with a comparably sized fragment of SEQ ID NO:23. In some embodiments, the polypeptide comprises an amino acid sequence wherein a fragment thereof has at least 99% sequence identity with a comparably sized fragment of SEQ ID NO:15, a second fragment thereof has at least 99% identity with a comparably sized fragment of SEQ ID NO:21, and a third fragment thereof has at least 99% identity with a comparably sized fragment of SEQ ID NO:23. In some embodiments, the polypeptide comprises an amino acid sequence wherein a fragment thereof has 100% sequence identity with a comparably sized fragment of SEQ ID NO:15, a second fragment thereof has at least 100% identity with a comparably sized fragment of SEQ ID NO:21, and a third fragment thereof has at least 100% identity with a comparably sized fragment of SEQ ID NO:23.

In some embodiments, the polypeptide comprises an amino acid sequence wherein a fragment thereof has at least 90% sequence identity with a comparably sized fragment of SEQ ID NO:13, a second fragment thereof has at least 90% identity with a comparably sized fragment of SEQ ID NO:21, and a third fragment thereof has at least 90% identity with a comparably sized fragment of SEQ ID NO:23. In some embodiments, the polypeptide comprises an amino acid sequence wherein a fragment thereof has at least 91% sequence identity with a comparably sized fragment of SEQ ID NO:13, a second fragment thereof has at least 91% identity with a comparably sized fragment of SEQ ID NO:21, and a third fragment thereof has at least 91% identity with a comparably sized fragment of SEQ ID NO:23. In some embodiments, the polypeptide comprises an amino acid sequence wherein a fragment thereof has at least 92% sequence identity with a comparably sized fragment of SEQ ID NO:13, a second fragment thereof has at least 92% identity with a comparably sized fragment of SEQ ID NO:21, and a third fragment thereof has at least 92% identity with a comparably sized fragment of SEQ ID NO:23. In some embodiments, the polypeptide comprises an amino acid sequence wherein a fragment thereof has at least 93% sequence identity with a comparably sized fragment of SEQ ID NO:13, a second fragment thereof has at least 93% identity with a comparably sized fragment of SEQ ID NO:21, and a third fragment thereof has at least 93% identity with a comparably sized fragment of SEQ ID NO:23. In some embodiments, the polypeptide comprises an amino acid sequence wherein a fragment thereof has at least 94% sequence identity with a comparably sized fragment of SEQ ID NO:13, a second fragment thereof has at least 94% identity with a comparably sized fragment of SEQ ID NO:21, and a third fragment thereof has at least 94% identity with a comparably sized fragment of SEQ ID NO:23. In some embodiments, the polypeptide comprises an amino acid sequence wherein a fragment thereof has at least 95% sequence identity with a comparably sized fragment of SEQ ID NO:13, a second fragment thereof has at least 95% identity with a comparably sized fragment of SEQ ID NO:21, and a third fragment thereof has at least 95% identity with a comparably sized fragment of SEQ ID NO:23. In some embodiments, the polypeptide comprises an amino acid sequence wherein a fragment thereof has at least 96% sequence identity with a comparably sized fragment of SEQ ID NO:13, a second fragment thereof has at least 96% identity with a comparably sized fragment of SEQ ID NO:21, and a third fragment thereof has at least 96% identity with a comparably sized fragment of SEQ ID NO:23. In some embodiments, the polypeptide comprises an amino acid sequence wherein a fragment thereof has at least 97% sequence identity with a comparably sized fragment of SEQ ID NO:13, a second fragment thereof has at least 97% identity with a comparably sized fragment of SEQ ID NO:21, and a third fragment thereof has at least 97% identity with a comparably sized fragment of SEQ ID NO:23. In some embodiments, the polypeptide comprises an amino acid sequence wherein a fragment thereof has at least 98% sequence identity with a comparably sized fragment of SEQ ID NO:13, a second fragment thereof has at least 98% identity with a comparably sized fragment of SEQ ID NO:21, and a third fragment thereof has at least 98% identity with a comparably sized fragment of SEQ ID NO:23. In some embodiments, the polypeptide comprises an amino acid sequence wherein a fragment thereof has at least 99% sequence identity with a comparably sized fragment of SEQ ID NO:13, a second fragment thereof has at least 99% identity with a comparably sized fragment of SEQ ID NO:21, and a third fragment thereof has at least 99% identity with a comparably sized fragment of SEQ ID NO:23. In some embodiments, the polypeptide comprises an amino acid sequence wherein a fragment thereof has 100% sequence identity with a comparably sized fragment of SEQ ID NO:13, a second fragment thereof has at least 100% identity with a comparably sized fragment of SEQ ID NO:21, and a third fragment thereof has at least 100% identity with a comparably sized fragment of SEQ ID NO:23.

In some embodiments, the polypeptide comprises an amino acid sequence wherein a fragment thereof has at least 90% sequence identity with a comparably sized fragment of SEQ ID NO:15, a second fragment thereof has at least 90% identity with a comparably sized fragment of SEQ ID NO:19, a third fragment thereof has at least 90% identity with a comparably sized fragment of SEQ ID NO:21, and a fourth fragment thereof has at least 90% identity with a comparably sized fragment of SEQ ID NO:23. In some embodiments, the polypeptide comprises an amino acid sequence wherein a fragment thereof has at least 91% sequence identity with a comparably sized fragment of SEQ ID NO:15, a second fragment thereof has at least 91% identity with a comparably sized fragment of SEQ ID NO:19, a third fragment thereof has at least 91% identity with a comparably sized fragment of SEQ ID NO:21, and a fourth fragment thereof has at least 91% identity with a comparably sized fragment of SEQ ID NO:23. In some embodiments, the polypeptide comprises an amino acid sequence wherein a fragment thereof has at least 92% sequence identity with a comparably sized fragment of SEQ ID NO:15, a second fragment thereof has at least 92% identity with a comparably sized fragment of SEQ ID NO:19, a third fragment thereof has at least 92% identity with a comparably sized fragment of SEQ ID NO:21, and a fourth fragment thereof has at least 92% identity with a comparably sized fragment of SEQ ID NO:23. In some embodiments, the polypeptide comprises an amino acid sequence wherein a fragment thereof has at least 93% sequence identity with a comparably sized fragment of SEQ ID NO:15, a second fragment thereof has at least 93% identity with a comparably sized fragment of SEQ ID NO:19, a third fragment thereof has at least 93% identity with a comparably sized fragment of SEQ ID NO:21, and a fourth fragment thereof has at least 93% identity with a comparably sized fragment of SEQ ID NO:23. In some embodiments, the polypeptide comprises an amino acid sequence wherein a fragment thereof has at least 94% sequence identity with a comparably sized fragment of SEQ ID NO:15, a second fragment thereof has at least 94% identity with a comparably sized fragment of SEQ ID NO:19, a third fragment thereof has at least 94% identity with a comparably sized fragment of SEQ ID NO:21, and a fourth fragment thereof has at least 94% identity with a comparably sized fragment of SEQ ID NO:23. In some embodiments, the polypeptide comprises an amino acid sequence wherein a fragment thereof has at least 95% sequence identity with a comparably sized fragment of SEQ ID NO:15, a second fragment thereof has at least 95% identity with a comparably sized fragment of SEQ ID NO:19, a third fragment thereof has at least 95% identity with a comparably sized fragment of SEQ ID NO:21, and a fourth fragment thereof has at least 95% identity with a comparably sized fragment of SEQ ID NO:23. In some embodiments, the polypeptide comprises an amino acid sequence wherein a fragment thereof has at least 96% sequence identity with a comparably sized fragment of SEQ ID NO:15, a second fragment thereof has at least 96% identity with a comparably sized fragment of SEQ ID NO:19, a third fragment thereof has at least 96% identity with a comparably sized fragment of SEQ ID NO:21, and a fourth fragment thereof has at least 96% identity with a comparably sized fragment of SEQ ID NO:23. In some embodiments, the polypeptide comprises an amino acid sequence wherein a fragment thereof has at least 97% sequence identity with a comparably sized fragment of SEQ ID NO:15, a second fragment thereof has at least 97% identity with a comparably sized fragment of SEQ ID NO:19, a third fragment thereof has at least 97% identity with a comparably sized fragment of SEQ ID NO:21, and a fourth fragment thereof has at least 97% identity with a comparably sized fragment of SEQ ID NO:23. In some embodiments, the polypeptide comprises an amino acid sequence wherein a fragment thereof has at least 98% sequence identity with a comparably sized fragment of SEQ ID NO:15, a second fragment thereof has at least 98% identity with a comparably sized fragment of SEQ ID NO:19, a third fragment thereof has at least 98% identity with a comparably sized fragment of SEQ ID NO:21, and a fourth fragment thereof has at least 98% identity with a comparably sized fragment of SEQ ID NO:23. In some embodiments, the polypeptide comprises an amino acid sequence wherein a fragment thereof has at least 99% sequence identity with a comparably sized fragment of SEQ ID NO:15, a second fragment thereof has at least 99% identity with a comparably sized fragment of SEQ ID NO:19, a third fragment thereof has at least 99% identity with a comparably sized fragment of SEQ ID NO:21, and a fourth fragment thereof has at least 99% identity with a comparably sized fragment of SEQ ID NO:23. In some embodiments, the polypeptide comprises an amino acid sequence wherein a fragment thereof has 100% sequence identity with a comparably sized fragment of SEQ ID NO:15, a second fragment thereof has 100% identity with a comparably sized fragment of SEQ ID NO:19, a third fragment thereof has 100% identity with a comparably sized fragment of SEQ ID NO:21, and a fourth fragment thereof has 100% identity with a comparably sized fragment of SEQ ID NO:23.

In some embodiments, the chimeric polypeptide is an enzyme. In some embodiments, the chimeric polypeptide is an enzyme capable of converting xylose to xylulose. In some embodiments, the chimeric polypeptide is a xylose isomerase (XI). In some embodiments, at least one parent sequence used as donor material for the chimeric polynucleotide is derived from a polynucleotide that encodes an XI. In some embodiments, when expressed heterologously in a yeast cell, the parent XI sequence is capable of conferring xylose isomerase activity to the host yeast cell. In some embodiments, when expressed heterologously in a yeast cell, the parent XI sequence is not capable of conferring xylose isomerase activity to the host yeast cell. When the donor XI does not function in the yeast host cell, it is referred to herein as a non-functional parent XI.

It is understood that nucleotide sequences encoding engineered forms of any of the chimeric polypeptides defined above are expressly included in the present invention. Further, any nucleotide sequence that comprises one or more amino acid substitutions, insertions and/or deletions as compared to the corresponding naturally occurring donor sequences, but that are within the ranges of identity or similarity as defined herein are expressly included in the invention. However, the chimeric polypeptides having xylose isomerase activity maintain certain conserved motifs. In one embodiment, the chimeric nucleotide sequence of the invention encodes a chimeric xylose isomerase amino acid sequence comprising a xylose isomerase signature sequence as defined, e.g., by Meaden et al. (1994, Gene, 141: 97-101): VXW[GP]GREG[YSTA] (present at positions 188-196, relative to SEQ ID NO: 11) and [LIVM]EPKPX[EQ]P (present at positions 233-240, relative to SEQ ID NO: 11), wherein "X" can be any amino acid and wherein amino acids in brackets indicates that one of the bracketed amino acids can be present at that position in the signature sequence. A xylose isomerase amino acid sequence of the invention can further comprise the conserved amino acid residues His-103, Asp-106, and Asp-341, which constitute a triad directly involved in catalysis, Lys-236 plays a structural as well as a functional catalytic role, and Glu-234 (relative to SEQ ID NO: 11), which is involved in magnesium binding (Vangrysperre et al., "Localization of the essential histidine and carboxylate group in D-xylose isomerases," *Biochem. J.* 265: 699-705(1990); Henrick et al., "Structures of D-xylose isomerase from *Arthrobacter* strain B3728 containing the inhibitors xylitol and D-sorbitol at 2.5 A and 2.3 A resolution, respectively," *J. Mol. Biol.* 208: 129-157 (1989); Bhosale et al., "Molecular and industrial aspects of glucose isomerase," *Microbiol. Rev.* 60: 280-300 (1996)). Amino acid positions of the above signature sequences and conserved residues refer to positions in the reference amino acid sequence of the *B. thetaiotaomicron* xylose isomerase of SEQ ID NO: 11. In amino acid sequences of the invention other than SEQ ID NO: 11, the amino acid positions of the above signature sequences and conserved residues are present in amino acid positions corresponding to the positions of the signature sequences and conserved residues in SEQ ID NO: 11, for example in a ClustalW (1.83 or 1.81) sequence alignment using default settings. The skilled person will know how to identify corresponding amino acid positions in xylose isomerase amino acid sequences other than SEQ ID NO: 11 using amino acid sequence alignment algorithms as defined hereinabove. These regions and positions will tolerate no or only conservative amino acid substitutions. One having ordinary skill in the art would understand that even conserved motifs can remain functional with conservative amino acid substitutions, and such substitutions are envisioned by the present invention. Amino acid substitutions outside of these regions and positions are unlikely to greatly affect xylose isomerase activity.

Additional structural features common to XIs have been described, e.g., by Chang et al., "Crystal Structures of Thermostable Xylose Isomerases from *Thermus caldophilus* and *Thermus thermophiles*: Possible Structural Determinants of Thermostability," *J. Mol. Biol.* 288:623-34 (1999), which is incorporated by reference in its entirety, and RCSB Protein Data Bank, "Xylose Isomerase From *Thermotoga neapolitana*," http://www.rcsb.org/pdb/explore/explore.do-?structure Id=1A0E, last accessed Jun. 29, 2014, at 5:15 pm. There are several known metal binding sits in the XI sequence, including at residues Glu-234, Glu-270, His-273, Asp-298, Asp-309, Asp-311, and Asp-341. One having ordinary skill in the art would understand that any deletions or non-conservative substitutions at any one or more of these residues may lead to a decreased functionability of the resulting XI.

In some embodiments, a host cell is engineered to express one or more of the chimeric polypeptides. In some embodiments, the host cell is a fungal cell, e.g. a yeast cell, e.g. a *S. cerevisiae* cell. In some embodiments the host cell is modified to have mutations affecting at least one gene encoding a protein of the pentose phosphate pathway. In some embodiments, the host cell has at least one mutation affecting the expression of at least one of XKS1, RKI1, RPE1, TKL1, TAL1 or a combination thereof. In some embodiments, the host cell has one or more mutations that correlate with an increase in the expression or an up-regulation of one or more of XKS1, RKI1, RPE1, TKL1, and/or TAL1. In some embodiments the host cell can be modified through the heterologous expression of one or more polynucleotides encoding XKS1, RKI1, RPE1, TKL1, and/or TAL1. In some embodiments, the host cell has one or more mutations that correlate with a decrease in the expression or down-regulation of one or more of XKS1, RKI1, RPE1, TKL1, and/or TAL1. In some embodiments, the host cell has a modification of one or more endogenous aldose reductases. In some embodiments, the aldose reductase is GRE3. In some embodiments, the host cell has a deletion or disruption of all or part of the endogenous GRE3 gene. In some embodiments, the aldose reductase gene is YPR1. In some embodiments, the host cell has a deletion or disruption of all or part of the endogenous YPR1 gene. In some embodiments, the host cell has a deletion or disruption of all or part of both the endogenous GRE3 gene and the endogenous YPR1 gene. In some embodiments, the host cell has a modification of PGM1 and/or PGM2. In some embodiments, the host cell overexpresses PGM1 and/or PGM2. In some embodiments, the host cell has increased levels of Pgm1 and/or Pgm2 polypeptide and/or mRNA relative to a comparable host cell lacking a modification of PGM1 and/or PGM2. In some embodiments, the host cell is a modified industrial yeast strain.

In some embodiments, the host cell comprises a deletion or disruption of one or more native enzymes that function to produce glycerol and/or regulate glycerol synthesis as described, e.g., in U.S. Patent Application Publication No. 2014/0186930, which is incorporated by reference herein in its entirety. In some embodiments, the host cell produces less glycerol than a control recombinant microorganism without deletion or disruption of said one or more endogenous enzymes that function to produce glycerol and/or regulate glycerol synthesis. In some embodiments, the one or more endogenous enzymes that function to produce glycerol are encoded by a GPD1 polynucleotide, a GPD2 polynucleotide, or both a GPD1 polynucleotide and a GPD2 polynucleotide. In some embodiments, one or both of the endogenous GPD1 and/or GPD2 genes are modified by mutation or deletion. In some embodiments, the host cell comprises a heterologous ADHE sequence. In some embodiments, the heterologous ADHE is from *Bifidobacterium adolescentis*. In some embodiments the native STL1 gene is upregulated by either modifying the promoter of the native copies or by introducing additional copies of STL1. In some embodiments the host cell comprises an ortholog of the native STL1. In some embodiments the native ACS2 gene is upregulated by either modifying the promoter of the native copies or by introducing additional copies of ACS2.

In some embodiments, the host cell comprises more than one copy of the chimeric polynucleotide. In some embodiments, the host cell comprises two copies, three copies, four copies, five copies, six copies, seven copies, eight copies, nine copies, ten copies, eleven copies, at least twelve copies, at least fifteen copies, or at least twenty copies of the chimeric polynucleotide.

In some embodiments, the chimeric polynucleotide can be present in a vector. In some embodiments, the host cell can comprise the chimeric polynucleotide within a vector. In some embodiments, the vector is a plasmid. In some embodiments, the host cell can express the chimeric polynucleotide from the vector. In some embodiments, the chimeric polynucleotide can be incorporated into the genome of the host cell. In some embodiments, the host cell is a fungal cell. In some embodiments, the host cell is a yeast cell. In some embodiments, the host cell is a *S. cerevisiae* cell.

Certain embodiments of the present invention describe methods for producing a fermentation product. In certain embodiments, the recombinant host cell comprising the chimeric polynucleotide or the recombinant polypeptide is contacted with a carbon source. In certain embodiments, the carbon source comprises xylose. In certain embodiments, xylose is the sole source of carbon in the carbon source. In certain embodiments, a fermentation product is produced by contacting the host cell with the carbon source. In certain embodiments, the fermentation product is recovered. In certain embodiments, the fermentation product is selected from the group consisting of ethanol, lactic acid, 3-hydroxypropionic acid, hydrogen, butyric acid, acrylic acid, acetic acid, succinic acid, citric acid, malic acid, fumaric acid, an amino acid, 1,3-propane-diol, ethylene, glycerol, acetone, isopropyl alcohol, butanol, a β-lactam, an antibiotic, cephalosporin, or a combination thereof. In certain embodiments, the fermentation product is ethanol.

III. Methods of Synthesis

Certain embodiments of the present invention describe methods of synthesizing a chimeric polynucleotide or chimeric polypeptide. In some embodiments, the chimeric polypeptide is synthesized by providing two or more parent xylose isomerase-encoding DNA sequences; providing a linearized vector capable of replication in yeast; providing a yeast cell; transforming the yeast cell with the at least two parent DNA sequences and the linearized vector; and screening the transformed yeast cells for recombination of the parent DNA sequences.

In some embodiments, the chimeric polypeptide is synthesized by providing at least two or more parent polynucleotide sequences; inserting each parent polynucleotide into a vector backbone creating a parent vector library; transforming host cells with at least two parent vectors; screening the transformed yeast cells for recombination of the parent polynucleotide sequence; and identifying transformed host cells wherein recombination of the at least two parent vectors has led to a chimeric polynucleotide sequence encoding a chimeric polypeptide.

In some embodiments, the method further comprises isolating the chimeric polynucleotide.

In some embodiments, at least two parent DNA sequences are used to create the chimeric polynucleotide or chimeric polypeptide. In some embodiments, at least three parent DNA sequences are used to create the chimeric polynucleotide or chimeric polypeptide. In some embodiments, at least four parent DNA sequences are used to create the chimeric polynucleotide or chimeric polypeptide.

In some embodiments, each parent DNA sequence used to create the chimeric polynucleotide or chimeric polypeptide is unique, such that no two parent sequences used in the same chimeric polynucleotide or polypeptide are derived from the same species. In some embodiments, at least one parent DNA sequence used to create the chimeric polynucleotide or chimeric polypeptide is derived from the same species as at least one other parent DNA sequence.

In some embodiments, at least one of the full length parent DNA sequences used to create the chimeric polynucleotide or the chimeric polypeptide encodes a polypeptide having xylose isomerase activity. In some embodiments, each full length parent DNA sequence used to create the chimeric polynucleotide or the chimeric polypeptide encodes a polypeptide having xylose isomerase activity.

In some embodiments, the donor parent sequences are codon optimized. In some embodiments, the donor parent sequences are synthesized as two independent but overlapping DNA fragments. In some embodiments, the donor parent sequences are synthesized as two independent and non-overlapping DNA fragments. In some embodiments, the two fragments together encompass the entire parent sequence. In some embodiments, the two fragments together encompass an incomplete portion of the entire parent sequence. In some embodiments, at least one independent DNA fragment comprises a region homologous to either the *S. cerevisiae* HSP150 promoter (HSP150p) or the *S. cerevisiae* ADH1 promoter (ADH1p). In some embodiments, at least one independent DNA fragment comprises a region homologous to HSP150p. In some embodiments, at least one independent DNA fragment comprises a region homologous to at least one of the *S. cerevisiae* HXT7 (HXT7t), PDC1 (PDC1t), RPL41B (RPL41Bt), RPL15A (RPL15At), DIT1 (DIT1t), RPL3 (RPL3t), IDP1 (IDP1t), YHI9 (YHI9t), EFM1 (EFM1t), or VMA16 (VMA16t) terminator sequences. In some embodiments, at least one independent DNA fragment comprises a region homologous to HXT7t. In some embodiments, one independent DNA fragment from a parent DNA sequence comprises a region homologous to the *S. cerevisiae* HSP150 promoter (HSP150p) and a second independent DNA fragment from the same parent DNA sequence comprises a region homologous to the *S. cerevisiae* HXT7 terminator sequence (HXT7t). In some embodiments, a promoter that is native to the host cell is used. In some embodiments, a promoter that is not native to the host cell is used. In some embodiments, a synthetic promoter is used.

In some embodiments, the vector backbone comprises one or more regions homologous to the *S. cerevisiae* HSP150 promoter (HSP150p). In some embodiments, the vector backbone comprises one or more regions homologous to the *S. cerevisiae* HXT7 (HXT7t) terminator sequence. In some embodiments, the vector backbone comprises one or more regions homologous to the *S. cerevisiae* HSP150 promoter (HSP150p) and comprises one or more regions homologous to the *S. cerevisiae* HXT7 terminator sequence (HXT7t). In some embodiments, the vector backbone is comprised of all or a fragment of pMU2116. In some embodiments the vector is circular. In some embodiments, the vector is linear. In certain embodiments, the vector comprises a single parent DNA fragment. In some embodiments, the vector comprises two independent and overlapping parent DNA fragments. In some embodiments, the vector comprises two independent and non-overlapping parent DNA fragments. In some embodiments, the vector is linear with a 5' fragment of the parent polynucleotide ligated to one end of the linear vector and a 3' fragment of the parent polynucleotide ligated to the opposite end of the linear vector, wherein the 5' and 3' fragments are independent and overlap. In some embodiments, the vector is linear with a 5' fragment of the parent polynucleotide ligated to one end of the linear vector and a 3' fragment of the parent polynucleotide ligated to the opposite end of the linear vector, wherein the 5' and 3' fragments are independent and do not overlap. In some embodiments, the circular vector comprises the entire parent XI coding region. In some embodiments, the circular vector comprises one or more fragments of the parent XI coding region.

In some embodiments the parent DNA is ligated directly with the vector backbone. In some embodiments a linker is used. In some embodiments the DNA fragments and the vector backbone fragments are transformed into the same host cell. In some embodiments, the host cell is a yeast. In some embodiments, the yeast is *S. cerevisiae*. In some embodiments, the *S. cerevisiae* is an industrial yeast strain. In some embodiments, the industrial yeast strain is genetically modified. In some embodiments, the formation of the chimeric sequence occurs in the host cell. In some embodiments, the chimeric sequence occurs through natural homologous recombination. In some embodiments, the chimeric polynucleotide or polypeptide is created through in vitro assembly methods. In some embodiments, the chimeric polynucleotide or polypeptide is created by in vitro homologous recombination. In some embodiments, the chimeric polynucleotide or polypeptide is created by sequence and ligase independent cloning (SLIC). In some embodiments, the chimeric polynucleotide or polypeptide is created by successive hybridization assembling (SHA).

In some embodiments, a chimeric polynucleotide library is created. In some embodiments, the chimeric library is created by transforming host cells with two or more vector backbone fragments; one or more full length non-functional parent DNA sequences, wherein the non-functional parent DNA sequence encodes a polypeptide unable to confer function normally in the host cell; and at least two fragments from functional parent DNA sequences, wherein the functional DNA sequences are able to function normally in the host cell. In some embodiments, the donor sequences encode for a polypeptide having xylose isomerase activity (e.g. an XI). In some embodiments, the donor DNA sequences include but are not limited to DNA sequences derived from the XI coding sequences of *Clostridium difficile* (CdXI), *C. aberensis* (CaXI), *Abiotrophia defectiva* (AdXI), *Lachnoanaerobaculum saburreum* (LsXI), *Reticulitermes speratus* (RsXI), *Prevotella ruminicola* (PrXI), *Lactobacillus_xylosus* (LxXI), *B. thetaiotaomicron* (BtXI), *Piromyces* (PiXI), *Clostridium phytofermentans* (CpXI), *Ciona intestinalis* (CiXI), *Fusobacterium morfiferum* (FmXI), *Thermotoga maritima* (TmXI), *Mastotermes darwiniensis* (MdXI), *Bacillus stearothermophilus* (BsXI), *Hordeum vulgare* (HvXI), *Zea mays* (ZmXI), *Arabidopsis thaliana* (AtXI), *Xanthomonas campestris* (XcXI), *C. pinensis* (CpiXI), and *P. distasonis* (PdXI) and the DNA sequences encoding XYM1 and XYM2.

In some embodiments, the transformed host cells are allowed to recover following transformation. In some embodiments, the transformed host cells are incubated overnight to allow for recovery following transformation. In some embodiments, the transformed host cells are plated onto plates comprising media comprising xylose as a carbon source. In some embodiments, the host cells are plated onto plates comprising media comprising xylose as the only carbon source. In some embodiments, the cells are cultured in a liquid media comprising xylose as the only carbon source. In some embodiments, colonies of transformed host cells are selected, wherein the selected colonies are able to grown on media comprising xylose or comprising xylose as the sole source of carbon. In some embodiments, the selected colonies are re-struck to fresh plates or cultured in liquid media. In some embodiments, a chimeric XI can be selected by culturing the transformed host cells in the presence of xylose and xylitol to select for a xylose isomerase with decreased xylitol inhibition. In some embodiments, the host cells can be cultured at varying temperatures. In some embodiments, the host cells are cultured at a temperature selected from the group consisting of about 25, about 26, about 27, about 28, about 29, about 30, about 31, about 32, about 33, about 34, about 35, about 36, about 37, about 38, about 39, and about 40 degrees C. In some embodiments, the host cells are cultured at a temperature of from about 25 to about 40 degrees C., from about 25 to about 35 degrees C., from about 25 to about 30 degrees C., from about 30 to about 40 degrees C., from about 30 to about 35 degrees C., from about 20 to about 45 degrees C., or from about 35 to about 40 degrees C.

In some embodiments, DNA from the selected transformed host cells is isolated, and the DNA is subjected to PCR amplification. In some embodiments, PCR is used to amplify all or a fragment of the chimeric polynucleotide. In some embodiments, primers specific to the HSP150p/HXT7t sequences are used in a PCR reaction to amplify the chimeric polynucleotide. In some embodiments, the amplified chimeric polynucleotide or a fragment thereof is sequenced. In some embodiments, the amplified chimeric polynucleotide or fragment thereof is sequenced using the Sanger method. In some embodiments, the resulting sequence of the chimeric polynucleotide or fragment thereof is aligned with one or more of the parent DNA sequences to determine the origin of the chimeric polynucleotide. In some embodiments, the amplified chimeric polynucleotide or fragment thereof is re-cloned into a vector backbone and rescreened for activity on xylose.

In some embodiments, a selected chimeric XI can be used in subsequent rounds of generating additional chimeric XIs. Any chimeric XI can be further modified by directed modifications of the sequence. In some embodiments, the chimeric polynucleotide is subjected to mutagenesis. In some embodiments, site-directed mutagenesis is used to introduce mutations to the chimeric polynucleotide. In some embodiments, site-directed mutagenesis is performed using PCR-based methods. In some embodiments, site-directed mutagenesis is performed using traditional PCR. In some embodiments, site-directed mutagenesis is performed using primer extension. In some embodiments, site-directed mutagenesis is performed using inverse PCR. In some embodiments, random mutagenesis is used to introduce mutations to the chimeric polynucleotide. In some embodiments, random mutagenesis is performed using PCR-based methods. In some embodiments, random mutagenesis is performed using error-prone PCR. In some embodiments, random mutagenesis is performed using insertion mutagenesis (e.g. through the use of transposons that randomly insert into the DNA sequence). In some embodiments, random mutagenesis is performed using chemical exposure (e.g. ethyl methanesulfonate (EMS) or nitrous acid. In some embodiments, random mutagenesis is performed using radiation exposure (e.g. exposure to UV light). In some embodiments, mutated chimeric polynucleotides are screened for growth and/or activity on xylose.

IV. Codon-Optimization

In some embodiments, the nucleotide sequence of the chimeric polynucleotide is codon-optimized for expression in a fungal host cell. In some embodiments, one or more of the parent polynucleotide sequences used to create the chimeric polynucleotide is codon optimized for expression in a fungal host cell. In some embodiments, the nucleotide sequence of the chimeric polynucleotide or the nucleotide sequence of one or more of the parent polynucleotide sequences is codon-optimized for expression in a yeast host cell. In some embodiments the nucleotide sequence of the chimeric polynucleotide or the nucleotide sequence of one or more of the parent polynucleotide sequences is codon-optimized for expression in *S. cerevisiae*. Codon-optimized polynucleotides can have a codon adaptation index (CAI) of about 0.8 to 1.0, about 0.9 to 1.0, or about 0.95 to 1.0.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The Codon Adaptation Index is described in more detail in Sharp and Li, *Nucleic Acids Research* 15:1281-1295 (1987), which is incorporated by reference herein in its entirety.

The CAI of codon-optimized sequences used in the present invention corresponds to from about 0.6 to about 1.0, from about 0.7 to about 1.0, from about 0.8 to about 1.0, from about 0.9 to about 1.0, from about 9.5 to about 1.0, or about 1.0. A codon-optimized sequence can be further modified for expression in a particular organism, depending on that organism's biological constraints. For example, large runs of "As" or "Ts" (e.g., runs greater than 4, 5, 6, 7, 8, 9, or 10 consecutive bases) can be removed from the sequences if these are known to effect transcription negatively. Furthermore, specific restriction enzyme sites can be removed for molecular cloning purposes. Examples of such restriction enzyme sites include PaI, AscI, BamHI, BgIII, EcoRJ and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is well known to one of skill in the art. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables and codon-optimizing programs are readily available, for example, at http://www.kazusa.or.jp/codon/(visited Jul. 15, 2014), and these tables can be adapted in a number of ways. See, e.g., Nakamura, Y., et al. "Codon usage tabulated from the international DNA sequence databases: status for the year 2000," *Nucl. Acids Res.* 28:292 (2000).

By utilizing one or more available tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods known to one having ordinary skill in the art.

In certain embodiments, an entire polypeptide sequence, or fragment, variant, or derivative thereof is codon-optimized by any method known in the art. Various desired fragments, variants or derivatives are designed, and each is then codon-optimized individually. In addition, partially codon-optimized coding regions of the present invention can be designed and constructed. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the codon positions have been codon-optimized for a given species. That is, they contain a codon that is preferentially used in the genes of a desired species, e.g., a yeast species such as *S. cerevisiae*, in place of a codon that is normally used in the native nucleic acid sequence.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon-optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

In some embodiments, one or more of the donor parent polynucleotide sequences are codon-optimized for expression in yeast. In some embodiments, the chimeric polynucleotide is codon-optimized for expression in yeast.

V. Methods of Producing Ethanol

Certain aspects of the present invention are directed to methods of producing a fermentation product. In some embodiments of the invention, the recombinant host cell is used to produce a fermentation product from a cellulosic or lignocellulosic material. In some embodiments, the fermentation product is ethanol, lactic acid, 3-hydroxy-propionic acid, hydrogen, butyric acid, acrylic acid, acetic acid, succinic acid, citric acid, malic acid, fumaric acid, an amino acid, 1,3-propane-diol, ethylene, glycerol, acetone, isopropyl alcohol, butanol, a β-lactam, an antibiotic, a cephalosporin, or a combination thereof. In some embodiments, the cellulosic or lignocellulosic material is insoluble cellulose, crystalline cellulose, pretreated hardwood, paper sludge, pretreated corn stover, pretreated sugar cane bagasse, pretreated corn cobs, pretreated switchgrass, pretreated municipal solid waste, pretreated distiller's dried grains, pretreated wheat straw, corn fiber, agave, or a combination thereof.

In some embodiments, one or more of the chimeric polypeptides are purified. In some embodiments, the one or more chimeric polypeptides are purified from a recombinant yeast host cell of the invention, a composition of the invention, a media supernatant of the invention, or a yeast strain of the invention. In some embodiments, one or more chimeric polypeptides in the composition are from a crude extract. In some embodiments, the crude extract is from a recombinant yeast host cell of the invention, a composition of the invention, a media supernatant of the invention, or a yeast strain of the invention.

One aspect of the invention is directed to a composition comprising a lignocellulosic material and a recombinant yeast host cell comprising at least one chimeric polypeptide having xylose isomerase activity. Another aspect of the invention is directed to a media supernatant generated by incubating a recombinant yeast host comprising as least one chimeric polypeptide having xylose isomerase activity with a medium containing xylose as the only carbon source. In some embodiments, the medium comprises a cellulosic or lignocellulosic material. In some embodiments, the cellulosic or lignocellulosic material is insoluble cellulose, crystalline cellulose, pretreated hardwood, paper sludge, saw mill or paper mill discards, pretreated corn stover, pretreated sugar cane bagasse, pretreated corn cobs, pretreated switchgrass, pretreated municipal solid waste, pretreated distiller's dried grains, pretreated wheat straw, corn fiber, agave, or a combination thereof.

In some embodiments, a fermentation product is produced by a method comprising contacting a recombinant host cell of the present invention with a carbon source, wherein the carbon source comprises xylose. In some embodiments, the fermentation product is selected from the group consisting of ethanol, lactic acid, 3-hydroxy-propionic acid, hydrogen, butyric acid, acrylic acid, acetic acid, succinic acid, citric acid, malic acid, fumaric acid, an amino acid, 1,3-propane-diol, ethylene, glycerol, acetone, isopropyl alcohol, butanol, a β-lactam, an antibiotic, and a cephalosporin. In some embodiments, the fermentation product is ethanol. In some embodiments, the fermentation product is recovered.

Certain aspects of the present invention are directed to a method of producing ethanol comprising contacting a source material comprising xylose with a polypeptide of the present invention. In some embodiments the polypeptide is a chimeric polypeptide. In some embodiments, the chimeric polypeptide has xylose isomerase activity (e.g. is an XI). In some embodiments, the source material is contacted by the polypeptide. In some embodiments, the polypeptide is isolated. In some embodiments, the source material is contacted by a produced by a transformed host cell. In some embodiments, the XI is not isolated. In some embodiments, the source material is contacted by a host cell of the present invention.

In some embodiments, the source material is a cellulosic biomass. In some embodiments, the source material is a lignocellulosic biomass. In some embodiments, the source material is selected from the group consisting of insoluble cellulose, crystalline cellulose, pretreated hardwood, softwood, paper sludge, newspaper, sweet sorghum, pretreated corn stover, pretreated sugar cane bagasse, pretreated corn cobs, pretreated switchgrass, pretreated municipal solid waste, pretreated distiller's dried grains, pretreated wheat straw, rice straw, nut shells, banana waste, sponge gourd fibers, corn fiber, agave, trees, corn stover, wheat straw, sugar cane bagasse, switchgrass, and combinations thereof. In some embodiments, the source material is corn stover.

EXAMPLES

The invention now being generally described, it will be more readily understood by reference to the following examples, which are included merely for purposes of illustration of certain aspect and embodiments of the present invention, and are not intended to limit the invention.

Example 1—S. cerevisiae Background Strain

A strain of S. cerevisiae was created that was suitable for the testing of functional xylose isomerases. The GRE3 locus of an industrial yeast strain was replaced with expression cassettes for the pentose phosphate pathway genes RPE1, RKI1, TKL1, and TAL1 as well as the native S. cerevisiae xyulokinase XKS1 (FIG. 1).

Example 2—Production of a Parent Vector Library

A total of 22 Donor XI sequences were codon optimized and synthesized by Integrated DNA Technologies (IDT gblocks) in two independent but overlapping DNA fragments. These XI fragments also contained homologous regions to either the *S. cerevisiae* HSP150 promoter (HSP150p) or the *S. cerevisiae* HXT7 terminator sequence (HXT7t), the regulatory regions used to drive the expression of the XIs (FIG. 3). The overlapping glocks for each XI were assembled via in vitro assembly (See, e.g., Gibson and Russello, "Gibson Assembly®-Building a Synthetic Biology Toolset," available at https://www.neb.com/tools-and-resources/feature-articles/gibson-assembly-building-a-synthetic-biology-toolset (last viewed Jul. 17, 2014)) along with the full length HSP150p and HXT7t. The in vitro assembly reaction was used as template for the PCR amplification of the full length expression cassette using Phusion polymerase. Parent XIs were tested for independent functionality by cloning them into the vector shown in FIG. 2 using YML within the *S. cerevisiae* strain described in Example 1. The resulting transformations were plated to YNBX plates and observed for the formation of colonies.

For use in the XI library, the vector shown in FIG. 2 was amplified in two over lapping fragments which resulted in the absence of the fragment spanning from the ADH1p through the PDC1t. This region was instead replaced with the HSP150p, the XIs, and the HXT7t via homologous recombination. Sequences enabling replication in yeast (2 micron ori, CEN/ARS ori) or *E. coli* (PBM1 ori, pBR322 ori, Col E1 ori, pUC ori) are shown. Protein coding sequences include the antibiotic resistance genes (ZEO R, Amp R) and the *S. cerevisiae* URA3 (Sc URA3) for selection in ura auxotrophs.

Nine of the 22 parent XIs screened were found to generate colonies when expressed within yeast; Cd XI, Ca XI, Ad XI, Ls XI, Rs XI, Pr XI, Lx XI, Bt XI, and Cp XI. For the generation of the XI chimera library, these donors were amplified in three overlapping segments using Phusion polymerase and gel extracted and purified using the nucleo-spin gel and PCR clean-up kit from Macherey-Nagel. In order to prevent the assembly of any functional parent XI the three fragments for any given XI were never included in the same transformation (Table 1).

TABLE 1

Summary of XI fragments added to each transformation. In addition to the fragments indicated in boxes with a "Y" below each transformation also received the two plasmid backbone fragments and each of the full length non-functional donor Xis. The boxes with a "Y" indicate DNA fragments which were added to each transformation.

|  | Transformation 1 | | | Transformation 2 | | | Transformation 3 | | |
| --- | --- | --- | --- | --- | --- | --- | --- | --- | --- |
|  | Frag A | Frag B | Frag C | Frag A | Frag B | Frag C | Frag A | Frag B | Frag C |
| Cd XI | Y | Y |  |  | Y | Y | Y |  | Y |
| Ca XI | Y | Y |  |  | Y | Y | Y |  | Y |
| Ad XI | Y | Y |  |  | Y | Y | Y |  | Y |
| Ls XI |  | Y | Y | Y |  | Y | Y | Y |  |
| Rs1 XI |  | Y | Y | Y |  | Y | Y | Y |  |
| Pr XI |  | Y | Y | Y |  | Y | Y | Y |  |
| Lx XI | Y |  | Y | Y | Y |  |  | Y | Y |
| Bt XI | Y |  | Y | Y | Y |  |  | Y | Y |
| Cp XI | Y |  | Y | Y | Y |  |  | Y | Y |

For the remaining 13 donors (Ci XI, Fm XI, Tm XI, Md XI, Bs XI, Hv XI, Zm XI, At XI, XYM1, XYM2, Xc XI, Cpi XI, Pd XI), which showed insufficient activity within the modified yeast strain to generate colony formation on xylose, full length XI sequences containing homology to the HSP150p and HXT7t sequences were amplified. PCR products were again gel extracted and purified using the nucleo-spin gel and PCR clean-up kit from Macherey-Nagel. The plasmid vector for which the XI expression cassette would assemble, as shown in FIG. 2, was also amplified using Phusion polymerase in two overlapping segments, which were gel extracted and purified as above. A schematic showing the amplification strategy is contained in FIG. 4.

Example 3—Chimeric XI Library Transformations

The DNA fragments generated above were transformed into the modified yeast strain described in Example 1 in three separate transformations using standard electroporation techniques. All reactions received two plasmid backbone fragments, each of the full length non-functional donor XIs, and two out of the three fragments for each of the nine functional XI parent sequences as outlined in Table 1 and summarized in FIG. 5. Transformations were allowed to recover in 1 ml of YPD for 2 hours at 35° C. prior to the addition of 1 ml of YPD+Zeo200 µg/ml (100 µg/ml final concentration) followed by overnight recovery. 1 ml of each transformation was plated to YNBX plates in 100 µl aliquots. Plates were incubated at 35° C. and observed daily for the formation of colonies. Any colonies obtained were re-struck to fresh YNBX plates prior to analysis.

Example 4—Amplification, Sequencing, and Screening

The plasmid inserts from each of the re-struck colonies were amplified by colony PCR using Phusion polymerase and primers specific to the HSP150p/HXT7t sequences. The products were checked by gel electrophoresis and purified using the gel and PCR clean-up kit from Macherey-Nagel. The purified PCR products were sequenced by the Sanger method at the Dartmouth College Sequencing Facility on the Applied Biosystems Model 3100 sequencer; the resulting reads were assembled using SeqMan Pro from the DNAS-TAR Lasergene 10 Core Suite. Chimeric sequences were aligned to all parent XIs in order to determine the origin of the DNA sequences. Sample chimeric polynucleotides created and identified using this approach are represented in FIG. 6.

For select chimeras of interest the amplified inserts were re-cloned into the plasmid backbone by YML and 8 independent colonies were chosen for screening on YNBX liquid media. Transformants were grown overnight in 600 ul of YPD+Zeo100 µg/ml in a 96 well plate along with control cultures grown in either YPD (integrated strains free of antibiotic markers) or YPD+Zeo100 µg/ml (plasmid containing controls, i.e. Bt XI). The overnight cultures were diluted 1/600 in fresh YNBX media and grown for 48 hours at 35° C. with constant shaking aerobically, prior to the measurement of the OD 600 for each culture.

Example 5—Growth Analysis

Selected chimera strains were inoculated into YPX media (yeast extract, peptone, and xylose) at identical starting cell concentrations in a 96-well plate format. Samples were then loaded into a Bioteck plate reader in an anaerobic chamber. Cell density was tracked using $OD_{600}$ measurements. Sample data of one such analysis is shown in FIGS. 7,8A and *B. Data is plotted for seven different strains over approximately 36 hours. In FIG. 7, the chimeric XI strain expressing the chimeric XI of SEQ ID NO:1 exhibits a better growth rate than the *B. thetaiotaomicron* XI strain in at least one of the strains tested. The data in FIG. 7 shows strains engineered with the *B. thetaiotaomicron* xylose isomerase (BtXI) and strains engineered with the chimeric XI 1 (SEQ ID NO:1), as provided in the present invention. The BtXI and chimeric strains are genetically identical except for the different XIs. A negative control strain is shown that is unable to grow on xylose. FIG. 8A shows the growth rates of various chimeric XI's integrated at the same copy number within the xylose screening background. FIG. 8B shows the growth rates of chimeric XI 1 and chimeric XI 6 integrated at the same copy number within the xylose screening background. FIGS. 8A and B also show a negative control strain that is unable to grow on xylose. Cell density was also tracked using $CO_2$ measurements. As shown in FIG. 8C, $CO_2$ production was monitored as an indirect measurement of xylose consumption and growth rate. FIG. 8C shows the growth rates of chimeric XI 1 and chimeric XI 7 integrated at the same copy number within the xylose screening background Example 6—Deletion of YPR1 Improves Ethanol Production from Xylose Selected chimera strains and a control strain were inoculated in YPX media (yeast extract, peptone, xylose) at identical starting cell concentrations in sealed pressure bottles. Samples were taken every six to twelve hours, and ethanol concentrations determined. The "chimera 1" strain, as shown in FIGS. 9 and 10, was created by stable genomic integration of a chimeric XI into the "host strain," used in FIGS. 9 and 10 as a negative control. Chimera 1 expresses a chimeric xylose isomerase comprising the amino acid sequence of SEQ ID NO:1. Chimera 1 further comprises additional copies of the native genes TKL1, TAL1, RPE1, RKI1, and XKS, and a deletion of the GRE3 gene. "Chimera 1+ypr1Δ" is identical to the Chimera 1 strain, except that Chimera 1+yprΔ has a deletion of the YPR1 gene. The "host strain" is a negative control that is unable to ferment xylose and produces no ethanol. FIG. 9 shows that the deletion of YPR1 enables the yeast cells to ferment xylose more quickly with no decrease in ethanol yield than comparable yeast cells that do not have a deletion of YPR1.

Example 7—Overexpression of PGM1 Improves Xylose Fermentation

Selected chimera strains and a control strain were inoculated in YPX media (yeast extract, peptone, xylose) at identical starting cell concentrations in a 96-well plate format and loaded into a Biotek plate reader in an anaerobic chamber. Cell density was tracked using $OD_{600}$ measurements. The data in FIG. 10 is plotted for three strains over approximately 48 hours. The "chimera 1" strain was created by stable genomic integration of a chimeric XI into the "host strain." Chimera 1 expresses a chimeric xylose isomerase comprising the amino acid sequence of SEQ ID NO:1. Chimera 1 further comprises additional copies of the native genes TKL1, TAL1, RPE1, RKI1, and XKS, and a deletion of the GRE3 gene. The "chimera 1+PGM1 o/e" strain is identical to the chimera 1 strain, except that chimera 1+PGM1 o/e has additional copies of the native PGM1 gene expressed under the control of a constitutive native promoter. The "host strain" is a negative control that is unable to grow on xylose. FIG. 10 shows that overexpression of PGM1 enables the yeast cells to grow more quickly on xylose than comparable yeast cells that do not overexpress PGM1.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

Following are particular embodiments of the disclosed invention:

E1. A polypeptide comprising an amino acid sequence having at least 90% sequence identity with an amino acid sequence selected from the group consisting of SEQ ID NOs: 1, 3, 5, 7, and 9.

E2. The polypeptide of claim 1, wherein the amino acid sequence has at least 95% sequence identity with an amino acid sequence selected from the group consisting of SEQ ID NOs: 1, 3, 5, 7, and 9.

E3. The polypeptide of claim 1, wherein the amino acid sequence has at least 98% sequence identity with an amino acid sequence selected from the group consisting of SEQ ID NOs: 1, 3, 5, 7, and 9.

E4. The polypeptide of claim 1, wherein the amino acid sequence has at least 99% sequence identity with an amino acid sequence selected from the group consisting of SEQ ID NOs: 1, 3, 5, 7, and 9.

E5. The polypeptide of claim 1, wherein the amino acid sequence has 100% sequence identity with an amino acid sequence selected from the group consisting of SEQ ID NOs: 1, 3, 5, 7, and 9.

E6. A polypeptide comprising an amino acid sequence having at least 90%, 95%, 98%, 99% or 100% sequence identity with an amino acid sequence of SEQ ID NO: 25 or SEQ ID NO: 27.

E7. A polypeptide comprising a C-terminal region and an N-terminal region, wherein the C-terminal region of the polypeptide comprises at least 5 contiguous amino acids from the amino acid sequence of SEQ ID NO:13 and the N-terminal region of the polypeptide comprises at least 5 contiguous amino acids from an amino acid sequence selected from the group consisting of SEQ ID NOs: 11, 15, 17, 23, and combinations thereof.

E8. The polypeptide of E7, wherein the N-terminal region of the polypeptide comprises at least 5 contiguous amino acids from the amino acid sequence of SEQ ID NO: 11.

E9. The polypeptide of E7, wherein the N-terminal region of the polypeptide comprises at least 5 contiguous amino acids from the amino acid sequence of SEQ ID NO: 15.

E10. The polypeptide of E7, wherein the N-terminal region of the polypeptide comprises at least 5 contiguous amino acids from the amino acid sequence of SEQ ID NO: 17.

E11. The polypeptide of E7, wherein the N-terminal region of the polypeptide comprises at least 5 contiguous amino acids from the amino acid sequence of SEQ ID NO: 23.

E12. The polypeptide of E7, E8, and E11, wherein the N-terminal region of the polypeptide comprises at least 5 contiguous amino acids from an amino acid sequence selected from the group consisting of SEQ ID NOs: 11, 23, and a combination thereof.

E13. The polypeptide of any one of E7 to E12, wherein the N-terminal region of the polypeptide comprises at least 5 contiguous amino acids from the amino acid sequence selected from the group consisting of SEQ ID NOs: 11, 17, 15, and combinations thereof.

E14. A polypeptide comprising a C-terminal region and an N-terminal region, wherein the C-terminal region comprises at least 5 contiguous amino acids from the amino acid sequence of SEQ ID NO:15 and the N-terminal region comprises at least 5 contiguous amino acids from an amino acid sequence selected from the group consisting of SEQ ID NOs: 19, 21, 23, and combinations thereof.

E15. The polypeptide of E14, wherein the C-terminal region further comprises at least 5 contiguous amino acids from SEQ ID NO:21.

E16. The polypeptide of E14 or E15, wherein the N-terminal region comprises at least 5 contiguous amino acids from SEQ ID NO:23.

E17. The polypeptide of E15 or E16, wherein the N-terminal region further comprises at least 5 contiguous amino acids from SEQ ID NO:21.

E18. The polypeptide of E16 or E17, wherein the N-terminal region further comprises at least 5 contiguous amino acids from SEQ ID NO:19.

E19. The polypeptide of any one of E1 to E18, wherein the polypeptide comprises:
a. the amino acids VXW[GP]GREG[YSTA] present at positions 188-196, wherein "X" is any amino acid and wherein amino acids in brackets indicate that one of the bracketed amino acids can be present at that position;
b. the amino acids [LIVM]EPKPX[EQ]P present at positions 233-240, wherein "X" can be any amino acid and wherein amino acids in brackets indicates that one of the bracketed amino acids can be present at that position; and
c. a His residue at position 103, an Asp residue at position 106, and an Asp residue at position 341;
wherein the positions refer to positions in the reference amino acid sequence of SEQ ID NO: 11.

E20. The polypeptide of any one of E7 to E19, wherein the polypeptide is an enzyme.

E21. The polypeptide of any one of E7 to E20, wherein the polypeptide has xylose isomerase activity.

E22. A polynucleotide having a nucleotide sequence encoding the amino acid sequence of any one of E1 to E18.

E23. The polynucleotide of E22, wherein the nucleotide sequence is codon optimized.

E24. The polynucleotide of E23, wherein the nucleotide sequence is codon optimized for expression in a fungal cell.

E25. The polynucleotide of E24, wherein the fungal cell is a yeast cell.

E26. The polynucleotide of E25, wherein the yeast cell is a *Saccharomyces cerevisiae* cell.

E27. A vector comprising the polynucleotide of any one of E22 to E26.

E28. A recombinant host cell comprising the vector of E27.

E29. A recombinant host cell comprising the polypeptide of any one of E1 to E21.

E30. A recombinant host cell comprising the polynucleotide of any one of E22 to E26.

E31. The recombinant host cell of E30, wherein the host cell has a genome and the polynucleotide is integrated into the genome of the host cell.

E32. The recombinant host cell of any one of E28 to E31, wherein the host cell is capable of growing on xylose as the sole carbon source.

E33. The recombinant host cell of any one of E28 to E32, wherein the host cell is a yeast cell.

E34. The recombinant host cell of any one of E28 to E33, wherein the host cell is a member of a genus selected from the group consisting of *Saccharomyces, Kluyveromyces, Candida, Pichia, Schizosaccharomyces, Hansenula, Kloeckera, Schwanniomyces,* and *Yarrowia*.

E35. The recombinant host cell of any one of E28 to E34, wherein the host cell is a member of a species selected from the group consisting of *Saccharomyces cerevisiae, Saccharomyces bulderi, Saccharomyces exiguus, Saccharomyces uvarum, Saccharomyces diastaticus, Kloeckera lactis, Kloeckera marxianus,* and *Kloeckera fragilis*.

E36. The recombinant host cell of any one of E28 to E35, wherein the host cell is a *S. cerevisiae* cell.

E37. The recombinant host cell of any one of E28 to E 36, wherein the host cell further comprises at least one additional genetic modification of one or more genes encoding a protein of the pentose phosphate pathway.

E38. The recombinant host cell of E37, wherein the host cell comprises additional genetic modifications in at least one of the endogenous genes selected from the group consisting of XKS1, RKI1, RPE1, TKL1, and TAL1.

E39. The recombinant host cell of E38, wherein the host cell comprises genetic modifications that lead to the overexpression of at least one of the endogenous genes selected from the group consisting of XKS1, RKI1, RPE1, TKL1, and TAL1.

E40. The recombinant host cell of any one of E28 to E39, wherein the host cell further comprises a modification of one or more aldose reductase genes.

E41. The recombinant host cell of E40, wherein the aldose reductase gene is GRE3.

E42. The recombinant host cell of E41, wherein the host cell comprises a deletion or disruption of the endogenous GRE3 gene.

E43. The recombinant host cell of E40, wherein the aldose reductase gene is YPR1.

E44. The recombinant host cell of E43, wherein the host cell comprises a deletion or disruption of the endogenous YPR1 gene.

E45. The recombinant host cell of E40, wherein said modification comprises a deletion or disruption of the endogenous aldose reductase genes GRE3 and YPR1.

E46. The recombinant host cell of any one of E28 to E45, wherein the host cell further comprises a modification of the endogenous PGM1 gene.

E47. The recombinant host cell of E46, wherein the modification of the endogenous PGM1 gene results in the overexpression of PGM1.

E48. A method for producing a fermentation product comprising contacting the recombinant host cell of any one of E28 to E47 with a carbon source, wherein said carbon source comprises xylose.

E49. The method of E48, wherein the fermentation product is selected from the group consisting of ethanol, lactic acid, 3-hydroxy-propionic acid, hydrogen, butyric acid, acrylic acid, acetic acid, succinic acid, citric acid, malic acid, fumaric acid, an amino acid, 1,3-propane-diol, ethylene, glycerol, acetone, isopropyl alcohol, butanol, a β-lactam, an antibiotic, and a cephalosporin.

E50. The method of E49, wherein the fermentation product is ethanol.

E51. The method of any one of E48 to E50, further comprising recovering the fermentation product.

E52. A method of synthesizing a chimeric polypeptide comprising:
a. providing at least two or more parent polynucleotide sequences, a linearized vector capable of replication in yeast, and a yeast cell;
b. transforming the yeast cell with the at least two parent polynucleotide sequences and the linearized vector; and
c. screening the transformed yeast cells for recombination of the parent polynucleotide sequences.

E53. The method of E52 wherein the identified yeast cells comprising the chimeric polynucleotide are isolated.

E54. The method of E52 or E53, wherein one or more of the parent polynucleotide sequences are derived from the genomes of a species selected from the group consisting of *Bacteroides thetaiotaomicron, Abiotrophia defectiva, Parabacteroides distasonis, Chitinophaga pinensis, Cyllamyces aberensis, Prevotella ruminicola*, and combinations thereof.

E55. The method of any one of E52 to E54, wherein at least one of the parent polynucleotide sequences encodes a polypeptide capable of converting xylose to xylulose.

E56. The method of any one of E52 to E54, wherein at least one of the polynucleotide sequences is a fragment of a full length polynucleotide sequence, wherein the full length polynucleotide sequence encodes a polypeptide capable of converting xylose to xylulose.

E57. The method of any one of E52 to E54, wherein the linearized vector comprises at least one homologous region comprising a polynucleotide sequence that has homology to at least one section of the parent polynucleotide sequence.

E58. The method of E57, wherein the at least one homologous region of the linearized vector is positioned at either the 5' or 3' end of the linearized vector.

E59. The method of E58, wherein the linearized vector comprises a homologous region at the 5' end and a homologous region at the 3' end.

E60. The method of any one of E52 to E59, wherein the transformed yeast cells undergo homologous recombination to generate a circular vector.

E61. The method of any one of E52 to E60, wherein the parent polynucleotide sequence is selected from the group consisting of SEQ ID NOs: 12, 14, 16, 18, 20, 22, and 24, or a fragment thereof.

E62. The method of any one of E52 to E61, wherein the synthesized chimeric polypeptide is capable of converting xylose to xylulose.

E63. The method of any one of E52 to E62, wherein the transformed yeast cells are screened by growing the transformed cells on xylose as the sole carbon source.

E64. The method of any one of E52 to E 62, wherein the identified cells are capable of growth on xylose as the sole carbon source are isolated.

E65. The method of any one of E52 to E 62, wherein the identified cells are lysed and DNA is extracted.

E66. The method of E65, wherein the extracted DNA is used as a template to amplify the chimeric polynucleotide sequence.

E67. A method of producing ethanol comprising contacting a source material comprising xylose with the polypeptide of any one of claims E1 to E 21.

E68. The method of E67, wherein the source material is a cellulosic or lignocellulosic biomass.

E69. The method of E67, wherein the source material is at least one material selected from the group consisting of insoluble cellulose, crystalline cellulose, pretreated hardwood, paper sludge, pretreated corn stover, pretreated sugar cane bagasse, pretreated corn cobs, pretreated switchgrass, pretreated municipal solid waste, pretreated distiller's dried grains, pretreated wheat straw, corn fiber, agave, trees, corn stover, wheat straw, sugar cane bagasse, and switchgrass.

E70. The method of E69, wherein the source material is corn stover.

E71. A method of producing ethanol comprising contacting a source material comprising xylose with the recombinant host cell of any one of E30 to E46.

E72. The method of E71, wherein the source material is a cellulosic biomass.

E73. The method of E71, wherein the source material is at least one material selected from the group consisting of trees, corn stover, wheat straw, sugarcane bagasse, switchgrass, corn, sugarcane, sugarbeet, and combinations thereof.

E74. The method of E73, wherein the source material is corn stover.

Those skilled in the art will recognize, or be able to ascertain using no more than routine experimentation, many equivalents to the specific embodiments of the invention described herein. Such equivalents are intended to be encompassed by the following claims.

---

The invention claimed is:

1. A chimeric polypeptide having a xylose isomerase activity, the chimeric polypeptide comprising an amino acid sequence having at least 95% sequence identity with an amino acid sequence of SEQ ID NO: 27,
wherein the chimeric polypeptide further comprises:
a. the amino acids VXW[GP]GREG[YSTA] present at positions 188-196, wherein "X" is any amino acid and wherein amino acids in brackets indicate that one of the bracketed amino acids can be present at that position; and
b. the amino acids [LIVM]EPKPX[EQ]P present at positions 233-240, wherein "X" can be any amino acid and wherein amino acids in brackets indicates that one of the bracketed amino acids can be present at that position; and
c. a His residue at position 103, an Asp residue at position 106, and an Asp residue at position 341;
wherein the positions refer to positions in the reference amino acid sequence of SEQ ID NO: 11.

2. A method of synthesizing the chimeric polypeptide of claim 1 comprising:
a. providing at least two or more parent polynucleotide sequences, a linearized vector capable of replication in yeast, and a yeast cell;
b. transforming the yeast cell with the at least two parent polynucleotide sequences and the linearized vector and wherein the parent polynucleotide sequences undergo recombination forming a chimeric polynucleotide encoding the chimeric polypeptide of claim 1; and
c. screening the transformed yeast cells for said recombination wherein said chimeric polynucleotide encodes said chimeric polypeptide.

3. A method of producing ethanol comprising contacting a source material comprising xylose with the polypeptide of claim 1.

4. A polynucleotide having a nucleotide sequence encoding the amino acid sequence of claim 1.

5. The polynucleotide of claim 4, wherein the nucleotide sequence is codon optimized.

6. A vector comprising the polynucleotide of claim 4.

* * * * *

SEQUENCE LISTING

```
<160> NUMBER OF SEQ ID NOS: 28

<210> SEQ ID NO 1
<211> LENGTH: 436
<212> TYPE: PRT
<213> ORGANISM: Artificial Sequence
<220> FEATURE:
<223> OTHER INFORMATION: Chimeric Xylose Isomerase 1

<400> SEQUENCE: 1

Met Ser Glu Leu Phe Gln Asn Ile Pro Lys Ile Lys Tyr Glu Gly Ala
1               5                   10                  15

Asn Ser Lys Asn Pro Leu Ala Phe His Tyr Tyr Asp Ala Glu Lys Glu
            20                  25                  30

Ile Met Gly Lys Lys Met Lys Asp Trp Leu Arg Phe Ala Met Ala Trp
        35                  40                  45

Trp His Thr Leu Cys Ala Glu Gly Ser Asp Gln Phe Gly Pro Gly Thr
    50                  55                  60

Lys Thr Phe Pro Trp Asn Glu Gly Thr Asp Pro Ile Glu Lys Ala Lys
65                  70                  75                  80

Gln Lys Val Asp Ala Gly Phe Glu Ile Met Thr Lys Leu Gly Ile Glu
                85                  90                  95

His Tyr Cys Phe His Asp Val Asp Leu Val Asp Glu Gly Lys Asn Val
            100                 105                 110
```

Glu Tyr Glu Lys Asn Leu Lys Thr Ile Val Ala Tyr Leu Lys Glu
            115                 120                 125

Lys Gln Lys Glu Thr Gly Ile Lys Leu Leu Trp Gly Thr Ala Asn Val
        130                 135                 140

Phe Gly His Ala Arg Tyr Met Asn Gly Ala Ala Thr Asn Pro Asp Phe
145                 150                 155                 160

Asp Val Val Ala Arg Ala Ala Val Gln Ile Lys Asn Ala Ile Asp Ala
                165                 170                 175

Thr Ile Glu Leu Gly Gly Glu Asn Tyr Val Phe Trp Gly Gly Arg Glu
            180                 185                 190

Gly Tyr Met Ser Leu Leu Asn Thr Asn Met Lys Arg Glu Lys Asp His
        195                 200                 205

Leu Ala Met Met Leu Thr Met Ala Arg Asp Tyr Gly Arg Lys Asn Gly
    210                 215                 220

Phe Lys Gly Thr Phe Leu Ile Glu Pro Lys Pro Met Glu Pro Thr Lys
225                 230                 235                 240

His Gln Tyr Asp Val Asp Ser Glu Thr Val Ile Gly Phe Leu Arg His
                245                 250                 255

Tyr Gly Leu Asp Lys Asp Phe Ala Leu Asn Ile Glu Val Asn His Ala
            260                 265                 270

Thr Leu Ala Gly His Thr Phe Glu His Glu Leu Gln Ala Ala Ala Asp
        275                 280                 285

Ala Gly Met Leu Cys Ser Ile Asp Ala Asn Arg Gly Asp Tyr Gln Asn
    290                 295                 300

Gly Trp Asp Thr Asp Gln Phe Pro Met Asp Ile Tyr Glu Leu Ala Gln
305                 310                 315                 320

Ala Trp Leu Val Ile Leu Glu Gly Gly Gly Leu Thr Thr Gly Gly Thr
                325                 330                 335

Asn Phe Asp Ala Lys Thr Arg Arg Asn Ser Thr Asp Leu Glu Asp Ile
            340                 345                 350

Phe Ile Ala His Ile Gly Gly Met Asp Ala Phe Ala Arg Ala Leu Met
        355                 360                 365

Ile Ala Ala Asp Ile Leu Glu Asn Ser Asp Tyr Arg Lys Met Arg Ala
    370                 375                 380

Glu Arg Tyr Ala Ser Phe Asp Ala Gly Glu Gly Lys Ala Phe Glu Asp
385                 390                 395                 400

Gly Lys Leu Thr Leu Glu Asp Leu Arg Thr Ile Ala Leu Arg Asp Gly
                405                 410                 415

Glu Pro Lys Gln Ile Ser Gly Lys Gln Glu Leu Tyr Glu Met Ile Val
            420                 425                 430

Asn Leu His Ile
        435

<210> SEQ ID NO 2
<211> LENGTH: 1311
<212> TYPE: DNA
<213> ORGANISM: Artificial Sequence
<220> FEATURE:
<223> OTHER INFORMATION: Chimeric Xylose Isomerase 1

<400> SEQUENCE: 2
atgtctgaat tgttccaaaa catcccaaag atcaagtacg aaggtgctaa ctctaagaac    60
ccattggctt tccactacta cgacgctgaa aaggaaatca tgggtaagaa gatgaaggac   120
tggttgagat tcgctatggc ttggtggcac actttgtgtg ctgaaggttc tgaccaattc   180

```
ggtccaggta ctaagacttt cccatggaac gaaggtactg acccaatcga aaaggctaag      240
caaaaggttg acgctggttt cgaaatcatg actaagttgg gtatcgaaca ctactgtttc      300
cacgacgttg acttggttga cgaaggtaag aacgttgaag aatacgaaaa gaacttgaag      360
actatcgttg cttacttgaa ggaaaagcaa aaggaaactg gtatcaagtt gttgtggggt      420
actgctaacg ttttcggtca cgctagatac atgaacggtg ctgctactaa cccagacttc      480
gacgttgttg ccagagctgc tgttcaaatt aagaacgcta ttgacgctac tattgaattg      540
ggtggtgaaa actacgtttt ctggggtggt agagaaggtt acatgtcttt gttgaacacc      600
aacatgaaga gagaaaagga tcatttggcc atgatgttga ctatggctag agattacggt      660
agaaagaatg gtttcaaggg tactttcttg atcgaaccta aacctatgga acctactaag      720
caccaatacg atgttgattc cgaaaccgtt atcggtttct tgagacatta cggtttggat      780
aaggatttcg ccttgaacat cgaagttaac catgctactt tggctggtca tactttcgaa      840
catgaattgc aagctgctgc tgatgctggt atgttgtgtt ctattgatgc taacagaggt      900
gactaccaaa atggttggga tactgatcaa ttcccaatgg atatctacga attggctcaa      960
gcttggttgg ttatttttga aggtggtggt ttgactactg gtggtactaa ttttgatgcc     1020
aagaccagaa gaaactccac tgatttggaa gacatcttca ttgcccatat cggtggtatg     1080
gatgcttttg ctagagcttt gatgattgct gccgatattt ggaaaactc cgactacaga     1140 aagatgagag ctgaaagata cgcttctttt gatgctggtg aaggtaaggc tttcgaagat     1200
ggtaaattga ccttggaaga tttgagaacc attgctttga gagatggtga acctaagcaa     1260
atttccggta agcaagaatt atacgaaatg atcgtcaact tgcacatcta a              1311
```

<210> SEQ ID NO 3
<211> LENGTH: 438
<212> TYPE: PRT
<213> ORGANISM: Artificial Sequence
<220> FEATURE:
<223> OTHER INFORMATION: Chimeric Xylose Isomerase 2

<400> SEQUENCE: 3

```
Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Glu Thr
            100                 105                 110

Ile Ala Glu Tyr Glu Arg Arg Met Lys Glu Ile Thr Asp Tyr Ala Leu
        115                 120                 125

Val Lys Met Lys Glu Tyr Pro Asn Ile Lys Leu Leu Trp Gly Thr Ala
    130                 135                 140

Asn Val Phe Gly His Ala Arg Tyr Met Asn Gly Ala Ala Thr Asn Pro
145                 150                 155                 160
```

```
Asp Phe Asp Val Val Ala Arg Ala Ala Val Gln Ile Lys Asn Ala Ile
            165                 170                 175
Asp Ala Thr Ile Glu Leu Gly Gly Glu Asn Tyr Val Phe Trp Gly Gly
        180                 185                 190
Arg Glu Gly Tyr Met Ser Leu Leu Asn Thr Asn Met Lys Arg Glu Lys
    195                 200                 205
Asp His Leu Ala Met Met Leu Thr Met Ala Arg Asp Tyr Gly Arg Lys
210                 215                 220
Asn Gly Phe Lys Gly Thr Phe Leu Ile Glu Pro Lys Pro Met Glu Pro
225                 230                 235                 240
Thr Lys His Gln Tyr Asp Val Asp Ser Glu Thr Val Ile Gly Phe Leu
                245                 250                 255
Arg His Tyr Gly Leu Asp Lys Asp Phe Ala Leu Asn Ile Glu Val Asn
            260                 265                 270
His Ala Thr Leu Ala Gly His Thr Phe Glu His Glu Leu Gln Ala Ala
        275                 280                 285
Ala Asp Ala Gly Met Leu Cys Ser Ile Asp Ala Asn Arg Gly Asp Tyr
    290                 295                 300
Gln Asn Gly Trp Asp Thr Asp Gln Phe Pro Met Asp Ile Tyr Glu Leu
305                 310                 315                 320
Ala Gln Ala Trp Leu Val Ile Leu Glu Gly Gly Leu Thr Thr Gly
                325                 330                 335
Gly Thr Asn Phe Asp Ala Lys Thr Arg Arg Asn Ser Thr Asp Leu Glu
            340                 345                 350
Asp Ile Phe Ile Ala His Ile Gly Gly Met Asp Ala Phe Ala Arg Ala
        355                 360                 365
Leu Met Ile Ala Ala Asp Ile Leu Glu Asn Ser Asp Tyr Arg Lys Met
    370                 375                 380
Arg Ala Glu Arg Tyr Ala Ser Phe Asp Ala Gly Glu Gly Lys Ala Phe
385                 390                 395                 400
Glu Asp Gly Lys Leu Thr Leu Glu Asp Leu Arg Thr Ile Ala Leu Arg
                405                 410                 415
Asp Gly Glu Pro Lys Gln Ile Ser Gly Lys Gln Glu Leu Tyr Glu Met
            420                 425                 430
Ile Val Asn Leu His Ile
        435

<210> SEQ ID NO 4
<211> LENGTH: 1317
<212> TYPE: DNA
<213> ORGANISM: Artificial Sequence
<220> FEATURE:
<223> OTHER INFORMATION: Chimeric Xylose Isomerase 2

<400> SEQUENCE: 4
atggctaagg aatacttccc attcactggt aagatcccat tcgaaggtaa ggactctaag     60
aacgttatgg ctttccacta ctacgaacca gaaaaggttg ttatgggtaa gaagatgaag    120
gactggttga agttcgctat ggcttggtgg cacactttgg gtggtgcttc tgctgaccaa    180
ttcggtggtc aaactagatc ttacgaatgg gacaaggctg ctgacgctgt tcaaagagct    240
aaggacaaga tggacgctgg tttcgaaatc atggacaagt gggtatcga atacttctgt    300 ttccacgacg ttgacttggt tgaagaaggt gaaactatcg ctgaatacga agaagaatg    360 aaggaaatca ctgactacgc tttggttaag atgaaggaat acccaaacat caagttgttg    420
tggggtactg ctaacgtttt cggtcacgct agatacatga acggtgctgc tactaaccca    480
```

```
gacttcgacg ttgttgccag agctgctgtt caaattaaga acgctattga cgctactatt    540
gaattgggtg gtgaaaacta cgttttctgg ggtggtagaa aaggttacat gtctttgttg    600
aacaccaaca tgaagagaga aaaggatcat ttggccatga tgttgactat ggctagagat    660
tacggtagaa agaatggttt caagggtact ttcttgatcg aacctaaacc tatggaacct    720
actaagcacc aatacgatgt tgattccgaa accgttatcg gtttcttgag acattacggt    780
ttggataagg atttcgcctt gaacatcgaa gttaaccatg ctactttggc tggtcatact    840
ttcgaacatg aattgcaagc tgctgctgat gctggtatgt tgtgttctat tgatgctaac    900
agaggtgact accaaaatgg ttgggatact gatcaattcc caatggatat ctacgaattg    960
gctcaagctt ggttggttat tttggaaggt ggtggtttga ctactggtgg tactaatttt   1020
gatgccaaga ccagaagaaa ctccactgat ttggaagaca tcttcattgc ccatatcggt   1080
ggtatggatg cttttgctag agctttgatg attgctgccg atattttgga aaactccgac   1140
tacagaaaga tgagagctga agatacgct tcttttgatg ctggtgaagg taaggctttc   1200
gaagatggta aattgacctt ggaagatttg agaaccattg ctttgagaga tggtgaacct   1260
aagcaaattt ccggtaagca agaattatac gaaatgatcg tcaacttgca catctaa      1317
```

<210> SEQ ID NO 5
<211> LENGTH: 437
<212> TYPE: PRT
<213> ORGANISM: Artificial Sequence
<220> FEATURE:
<223> OTHER INFORMATION: Chimeric Xylose Isomerase 3

<400> SEQUENCE: 5

```
Met Val Lys Glu Tyr Phe Pro Ala Ile Gln Lys Ile Lys Phe Glu Gly
1               5                   10                  15

Lys Asp Ser Lys Asn Pro Met Ala Phe His Tyr Tyr Asp Ala Glu Lys
            20                  25                  30

Glu Ile Met Gly Lys Lys Met Lys Asp Trp Leu Arg Phe Ala Met Ala
        35                  40                  45

Trp Trp His Thr Leu Cys Ala Glu Gly Ser Asp Gln Phe Gly Pro Gly
    50                  55                  60

Thr Lys Thr Phe Pro Trp Asn Glu Gly Thr Asp Pro Ile Glu Lys Ala
65                  70                  75                  80

Lys Gln Lys Val Asp Ala Gly Phe Glu Ile Met Thr Lys Leu Gly Ile
                85                  90                  95

Glu His Tyr Cys Phe His Asp Val Asp Leu Val Asp Glu Gly Lys Asn
            100                 105                 110

Val Glu Glu Tyr Glu Lys Asn Leu Lys Thr Ile Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ala Thr Asn Pro Tyr
145                 150                 155                 160

Phe Pro Thr Val Ala Cys Val Gly Thr Gln Ile Lys Asn Ala Ile Asp
                165                 170                 175

Ala Cys Ile Ala Leu Gly Gly Glu Asn Tyr Val Phe Trp Gly Gly Arg
            180                 185                 190

Glu Gly Tyr Met Ser Leu Leu Asn Thr Asn Met Lys Arg Glu Lys Asp
        195                 200                 205

His Leu Ala Met Met Leu Thr Met Ala Arg Asp Tyr Gly Arg Lys Asn
```

```
               210                 215                 220
Gly Phe Lys Gly Thr Phe Leu Ile Glu Pro Lys Pro Met Glu Pro Thr
225                 230                 235                 240

Lys His Gln Tyr Asp Val Asp Ser Glu Thr Val Ile Gly Phe Leu Arg
                245                 250                 255

His Tyr Gly Leu Asp Lys Asp Phe Ala Leu Asn Ile Glu Val Asn His
                    260                 265                 270

Ala Thr Leu Ala Gly His Thr Phe Glu His Glu Leu Gln Ala Ala Ala
                275                 280                 285

Asp Ala Gly Met Leu Cys Ser Ile Asp Ala Asn Arg Gly Asp Tyr Gln
            290                 295                 300

Asn Gly Trp Asp Thr Asp Gln Phe Pro Met Asp Ile Tyr Glu Leu Ala
305                 310                 315                 320

Gln Ala Trp Leu Val Ile Leu Glu Gly Gly Leu Thr Thr Gly Gly
                325                 330                 335

Thr Asn Phe Asp Ala Lys Thr Arg Arg Asn Ser Thr Asp Leu Glu Asp
                340                 345                 350

Ile Phe Ile Ala His Ile Gly Gly Met Asp Ala Phe Ala Arg Ala Leu
                355                 360                 365

Met Ile Ala Ala Asp Ile Leu Glu Asn Ser Asp Tyr Arg Lys Met Arg
                370                 375                 380

Ala Glu Arg Tyr Ala Ser Phe Asp Ala Gly Glu Gly Lys Ala Phe Glu
385                 390                 395                 400

Asp Gly Lys Leu Thr Leu Glu Asp Leu Arg Thr Ile Ala Leu Arg Asp
                405                 410                 415

Gly Glu Pro Lys Gln Ile Ser Gly Lys Gln Glu Leu Tyr Glu Met Ile
                420                 425                 430

Val Asn Leu His Ile
                435

<210> SEQ ID NO 6
<211> LENGTH: 1314
<212> TYPE: DNA
<213> ORGANISM: Artificial Sequence
<220> FEATURE:
<223> OTHER INFORMATION: Chimeric Xylose Isomerase 3

<400> SEQUENCE: 6
atggttaagg aatacttccc agctatccaa agatcaagt tcgaaggtaa ggactctaag      60
aacccaatgg ctttccacta ctacgacgct gaaaaggaaa tcatgggtaa gaagatgaag    120
gactggttga gattcgctat ggcttggtgg cacactttgt gtgctgaagg ttctgaccaa    180
ttcggtccag gtactaagac tttcccatgg aacgaaggta ctgacccaat cgaaaaggct    240
aagcaaaagg ttgacgctgg tttcgaaatc atgactaagt gggtatcga acactactgt    300 ttccacgacg ttgacttggt tgacgaaggt aagaacgttg aagaatacga aaagaacttg    360
aagactatcg ttgcttactt gaaggaaaag caaaaggaaa ctggtatcaa gttgttgtgg    420
tctactgcta acgttttcgg tcacaagaga tatatgaacg gtgctgctac taatccatac    480
tttccaactg ttgcttgcgt tggtactcaa atcaagaatg ctattgatgc ttgcattgct    540
ttgggtggtg aaaattatgt tttctggggt ggtagagaag gttacatgtc tttgttgaac    600
accaacatga gagagaaaa ggatcatttg gccatgatgt tgactatggc tagagattac    660
ggtagaaaga atggtttcaa gggtactttc ttgatcgaac taaacctat ggaacctact    720 aagcaccaat acgatgttga ttccgaaacc gttatcggtt tcttgagaca ttacggtttg    780
```

```
gataaggatt tcgccttgaa catcgaagtt aaccatgcta ctttggctgg tcatactttc    840
gaacatgaat tgcaagctgc tgctgatgct ggtatgttgt gttctattga tgctaacaga    900
ggtgactacc aaaatggttg ggatactgat caattcccaa tggatatcta cgaattggct    960
caagcttggt tggttatttt ggaaggtggt ggtttgacta ctggtggtac taattttgat   1020
gccaagacca aagaaactc cactgatttg aagacatct tcattgccca tatcggtggt   1080
atggatgctt tgctagagc tttgatgatt gctgccgata ttttggaaaa ctccgactac   1140
agaaagatga gagctgaaag atacgcttct tttgatgctg gtgaaggtaa ggctttcgaa   1200
gatggtaaat tgaccttgga agatttgaga accattgctt tgagagatgg tgaacctaag   1260
caaatttccg gtaagcaaga attatacgaa atgatcgtca acttgcacat ctaa         1314
```

<210> SEQ ID NO 7
<211> LENGTH: 438
<212> TYPE: PRT
<213> ORGANISM: Artificial Sequence
<220> FEATURE:
<223> OTHER INFORMATION: Directed Chimeric Xylose Isomerase 1

<400> SEQUENCE: 7

```
Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Glu Thr
            100                 105                 110

Ile Ala Glu Tyr Glu Arg Arg Met Lys Glu Ile Thr Asp Tyr Ala Leu
        115                 120                 125

Val Lys Met Lys Glu Tyr Pro Asn Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Thr Asn Tyr Val Phe Trp Gly Gly
            180                 185                 190

Arg Glu Gly Tyr Met Thr Leu Leu Asn Thr Asp Met Lys Arg Glu Gln
        195                 200                 205

Glu His Leu Ala Arg Phe Leu Thr Met Ala Lys Asp Tyr Ala Arg Lys
    210                 215                 220

Gln Gly Phe Thr Gly Thr Phe Phe Ile Glu Pro Lys Pro Cys Glu Pro
225                 230                 235                 240

Thr Lys His Gln Tyr Asp Tyr Asp Ala Ala Thr Val Ile Gly Phe Leu
                245                 250                 255

Arg His Phe Gly Leu Asp Lys Asp Phe Lys Leu Asn Leu Glu Val Asn
            260                 265                 270
```

```
His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Tyr
    290                 295                 300

Gln Asn Gly Trp Asp Thr Asp Gln Phe Pro Ile Asp Gln Tyr Glu Leu
305                 310                 315                 320

Val Gln Ala Trp Met Glu Ile Ile Arg Gly Gly Phe Thr Thr Gly
                325                 330                 335

Gly Thr Asn Phe Asp Ala Lys Thr Arg Arg Asn Ser Thr Asp Leu Glu
            340                 345                 350

Asp Ile Ile Ala His Ile Ser Gly Met Asp Ala Met Ala Arg Ala
        355                 360                 365

Leu Glu Asn Ala Ala Lys Leu Leu Thr Glu Ser Pro Tyr Lys Lys Met
    370                 375                 380

Lys Ala Asp Arg Tyr Ala Ser Phe Asp Ser Gly Met Gly Lys Asp Phe
385                 390                 395                 400

Glu Asp Gly Lys Leu Thr Phe Glu Gln Val Tyr Glu Tyr Gly Lys Lys
                405                 410                 415

Val Asn Glu Pro Lys Gln Thr Ser Gly Lys Gln Glu Leu Tyr Glu Ala
            420                 425                 430

Ile Val Ala Met Tyr Met
        435

<210> SEQ ID NO 8
<211> LENGTH: 1317
<212> TYPE: DNA
<213> ORGANISM: Artificial Sequence
<220> FEATURE:
<223> OTHER INFORMATION: Directed Chimeric Xylose Isomerase 1

<400> SEQUENCE: 8
atggctaagg aatacttccc attcactggt aagatcccat tcgaaggtaa ggactctaag      60
aacgttatgg ctttccacta ctacgaacca gaaaaggttg ttatgggtaa gaagatgaag     120
gactggttga gttcgctat ggcttggtgg cacactttgg gtggtgcttc tgctgaccaa     180
ttcggtggtc aaactagatc ttacgaatgg gacaaggctg ctgacgctgt tcaaagagct     240
aaggacaaga tggacgctgg tttcgaaatc atggacaagt tgggtatcga atacttctgt     300
ttccacgacg ttgacttggt tgaagaaggt gaaactatcg ctgaatacga agaagaatg      360 aaggaaatca ctgactacgc tttggttaag atgaaggaat acccaaacat caagttgttg     420
tggggtactg ctaacgtttt cggtaacaag agatacgcta acggtgcttc tactaaccca     480
gacttcgacg ttgttgctag agctatcgtt caaatcaaga acgctatcga cgctactatc     540
aagttgggtg gtactaacta cgttttctgg ggtggtagag aaggttacat gactttgttg     600
aacaccgaca tgaagagaga caagaacat ttggctagat tcttgaccat ggctaaagat     660
tacgctagaa agcaaggttt caccggtact ttttcattg aacctaagcc atgcgaacct     720
accaaacatc aatatgatta cgatgctgcc accgttattg gttttttgag acatttcggt     780
ttggacaagg acttcaagtt gaacttggaa gttaaccatg ctactttggc tggtcacact     840
ttcgaacacg aattggcttg tgctgttgac gctggtatgt tgggttctat cgacgctaac     900
agaggtgact accaaaacgg ttgggacact gaccaattcc caatcgacca atacgaattg     960
gttcaagctt ggatggaaat catcagaggt ggtggtttca ctactggtgg tactaacttc    1020
gacgctaaga ctagaagaaa ctctactgac ttggaagaca tcatcatcgc tcacatctct    1080
```

```
ggtatggacg ctatggctag agctttggaa aacgctgcta agttgttgac tgaatctcca    1140
tacaagaaga tgaaggctga cagatacgct tctttcgact ctggtatggg taaggacttc    1200
gaagacggta agttgacttt cgaacaagtt tacgaatacg gtaagaaggt taacgaacca    1260
aagcaaactt ctggtaagca agaattgtac gaagctatcg ttgctatgta catgtga      1317
```

<210> SEQ ID NO 9
<211> LENGTH: 443
<212> TYPE: PRT
<213> ORGANISM: Artificial Sequence
<220> FEATURE:
<223> OTHER INFORMATION: Directed Chimeric Xylose Isomerase 2

<400> SEQUENCE: 9

```
Met Lys Leu Thr Val Gly Asp Lys Glu Tyr Phe Lys Gly Ile Lys Pro
1               5                   10                  15

Ile Lys Phe Glu Gly Lys Asp Ser Lys Asn Val Met Ala Phe His Tyr
            20                  25                  30

Tyr Glu Pro Glu Lys Val Val Met Gly Lys Lys Met Lys Asp Trp Leu
        35                  40                  45

Lys Phe Ala Met Ala Trp Trp His Thr Leu Gly Gly Ala Ser Ala Asp
    50                  55                  60

Gln Phe Gly Gly Gln Thr Arg Ser Tyr Glu Trp Asp Lys Ala Ala Asp
65                  70                  75                  80

Ala Val Gln Arg Ala Lys Asp Lys Met Asp Ala Gly Phe Glu Ile Met
                85                  90                  95

Asp Lys Leu Gly Ile Glu Tyr Phe Cys Phe His Asp Val Asp Leu Val
            100                 105                 110

Glu Glu Gly Glu Thr Ile Ala Glu Tyr Glu Arg Arg Met Lys Glu Ile
        115                 120                 125

Thr Asp Tyr Ala Leu Val Lys Met Lys Glu Tyr Pro Asn Ile Lys Leu
    130                 135                 140

Leu Trp Gly Thr Ala Asn Val Phe Gly Asn Lys Arg Tyr Ala Asn Gly
145                 150                 155                 160

Ala Ser Thr Asn Pro Asp Phe Asp Val Val Ala Arg Ala Ile Val Gln
                165                 170                 175

Ile Lys Asn Ala Ile Asp Ala Thr Ile Lys Leu Gly Gly Thr Asn Tyr
            180                 185                 190

Val Phe Trp Gly Gly Arg Glu Gly Tyr Met Thr Leu Leu Asn Thr Asp
        195                 200                 205

Met Lys Arg Glu Gln Glu His Leu Ala Arg Phe Leu Thr Met Ala Lys
    210                 215                 220

Asp Tyr Ala Arg Lys Gln Gly Phe Thr Gly Thr Phe Phe Ile Glu Pro
225                 230                 235                 240

Lys Pro Cys Glu Pro Thr Lys His Gln Tyr Asp Tyr Asp Ala Ala Thr
                245                 250                 255

Val Ile Gly Phe Leu Arg His Phe Gly Leu Asp Lys Asp Phe Lys Leu
            260                 265                 270

Asn Leu Glu Val Asn His Ala Thr Leu Ala Gly His Thr Phe Glu His
        275                 280                 285

Glu Leu Ala Cys Ala Val Asp Ala Gly Met Leu Gly Ser Ile Asp Ala
    290                 295                 300

Asn Arg Gly Asp Tyr Gln Asn Gly Trp Asp Thr Asp Gln Phe Pro Ile
305                 310                 315                 320
```

Asp Gln Tyr Glu Leu Val Gln Ala Trp Met Glu Ile Ile Arg Gly Gly
              325                 330                 335

Gly Phe Thr Thr Gly Gly Thr Asn Phe Asp Ala Lys Thr Arg Arg Asn
          340                 345                 350

Ser Thr Asp Leu Glu Asp Ile Ile Ile Ala His Ile Ser Gly Met Asp
      355                 360                 365

Ala Met Ala Arg Ala Leu Glu Asn Ala Ala Lys Leu Leu Thr Glu Ser
370                 375                 380

Pro Tyr Lys Lys Met Lys Ala Asp Arg Tyr Ala Ser Phe Asp Ser Gly
385                 390                 395                 400

Met Gly Lys Asp Phe Glu Asp Gly Lys Leu Thr Phe Glu Gln Val Tyr
              405                 410                 415

Glu Tyr Gly Lys Lys Val Asn Glu Pro Lys Gln Thr Ser Gly Lys Gln
          420                 425                 430

Glu Leu Tyr Glu Ala Ile Val Ala Met Tyr Met
      435                 440

```
<210> SEQ ID NO 10
<211> LENGTH: 1332
<212> TYPE: DNA
<213> ORGANISM: Artificial Sequence
<220> FEATURE:
<223> OTHER INFORMATION: Directed Chimeric Xylose Isomerase 2

<400> SEQUENCE: 10
atgaagttga ccgttggtga caaagaatac ttcaagggta ttaagccaat caagttcgaa      60
ggtaaggact ctaagaacgt tatggctttc cactactacg aaccagaaaa ggttgttatg     120
ggtaagaaga tgaaggactg gttgaagttc gctatggctt ggtggcacac tttgggtggt     180
gcttctgctg accaattcgg tggtcaaact agatcttacg aatgggacaa ggctgctgac     240
gctgttcaaa gagctaagga caagatggac gctggtttcg aaatcatgga caagttgggt     300
atcgaatact ctgtttcca cgacgttgac ttggttgaag aaggtgaaac tatcgctgaa     360
tacgaaagaa gaatgaagga aatcactgac tacgctttgg ttaagatgaa ggaatacccca    420
aacatcaagt tgttgtgggg tactgctaac gttttcggta caagagata cgctaacggt     480
gcttctacta acccagactt cgacgttgtt gctagagcta tcgttcaaat caagaacgct     540
atcgacgcta ctatcaagtt gggtggtact aactacgttt tctggggtgg tagagaaggt     600
tacatgactt tgttgaacac cgacatgaag agagaacaag aacatttggc tagattcttg     660
accatggcta agattacgc tagaaagcaa ggtttcaccg gtacttttttt cattgaacct     720
aagccatgcg aacctaccaa acatcaatat gattacgatg ctgccaccgt tattggtttt     780
ttgagacatt tcggttttgga caaggacttc aagttgaact ggaagttaa ccatgctact     840
ttggctggtc acactttcga cacgaattg gcttgtgctg ttgacgctgg tatgttgggt     900
tctatcgacg ctaacagagg tgactaccaa acggttggg acactgacca attcccaatc     960
gaccaatacg aattggttca gcttggatg gaaatcatca gaggtggtgg tttcactact    1020
ggtggtacta acttcgacgc taagactaga agaaactcta ctgacttgga agacatcatc    1080
atcgctcaca tctctggtat ggacgctatg gctagagctt tggaaaacgc tgctaagttg    1140
ttgactgaat ctccatacaa gaagatgaag gctgacagat acgcttcttt cgactctggt    1200
atgggtaagg acttcgaaga cggtaagttg acttttcgaac aagtttacga atacggtaag    1260
aaggttaacg aaccaaagca aacttctggt aagcaagaat tgtacgaagc tatcgttgct    1320
atgtacatgt ga                                                        1332
```

<210> SEQ ID NO 11
<211> LENGTH: 438
<212> TYPE: PRT
<213> ORGANISM: Bacteroides thetaiotaomicron

<400> SEQUENCE: 11

```
Met Ala Thr Lys Glu Phe Phe Pro Gly Ile Glu Lys Ile Lys Phe Glu
1               5                   10                  15

Gly Lys Asp Ser Lys Asn Pro Met Ala Phe Arg Tyr Tyr Asp Ala Glu
            20                  25                  30

Lys Val Ile Asn Gly Lys Lys Met Lys Asp Trp Leu Arg Phe Ala Met
        35                  40                  45

Ala Trp Trp His Thr Leu Cys Ala Glu Gly Gly Asp Gln Phe Gly Gly
    50                  55                  60

Gly Thr Lys Gln Phe Pro Trp Asn Gly Asn Ala Asp Ala Ile Gln Ala
65                  70                  75                  80

Ala Lys Asp Lys Met Asp Ala Gly Phe Glu Phe Met Gln Lys Met Gly
                85                  90                  95

Ile Glu Tyr Tyr Cys Phe His Asp Val Asp Leu Val Ser Glu Gly Ala
            100                 105                 110

Ser Val Glu Glu Tyr Glu Ala Asn Leu Lys Glu Ile Val Ala Tyr Ala
        115                 120                 125

Lys Gln Lys Gln Ala Glu Thr Gly Ile Lys Leu Leu Trp Gly Thr Ala
    130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Glu Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Gln Met Leu Thr Ile Ala Arg Asp Tyr Ala Arg Ala
    210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
    290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Leu Gly Thr Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Ala Met Ala Arg Ala
        355                 360                 365

Leu Glu Ser Ala Ala Ala Leu Leu Asp Glu Ser Pro Tyr Lys Lys Met
```

```
                370             375             380
Leu Ala Asp Arg Tyr Ala Ser Phe Asp Gly Gly Lys Gly Lys Glu Phe
385                 390                 395                 400

Glu Asp Gly Lys Leu Thr Leu Glu Asp Val Val Ala Tyr Ala Lys Thr
                405                 410                 415

Lys Gly Glu Pro Lys Gln Thr Ser Gly Lys Gln Glu Leu Tyr Glu Ala
            420                 425                 430

Ile Leu Asn Met Tyr Cys
            435

<210> SEQ ID NO 12
<211> LENGTH: 1317
<212> TYPE: DNA
<213> ORGANISM: Bacteroides thetaiotaomicron

<400> SEQUENCE: 12
atggcaacaa agaattttt tccgggaatt gaaaagatta aatttgaagg taaagatagt      60
aagaacccga tggcattccg ttattacgat gcagagaagg tgattaatgg taaaaagatg     120
aaggattggc tgagattcgc tatggcatgg tggcacacat tgtgcgctga aggtggtgat     180
cagttcggtg gcgaacaaa gcaattccca tggaatggta atgcagatgc tatacaggca     240
gcaaaagata gatggatgc aggatttgaa ttcatgcaga gatgggtat cgaatactat      300 tgcttccatg acgtagactt ggtttcgaa ggtgccagtg tagaagaata cgaagctaac     360
ctgaaagaaa tcgtagctta tgcaaaacag aaacaggcag aaaccggtat caaactactg     420
tggggtactg ctaatgtatt cggtcacgcc cgctatatga acgtgcagc taccaatcct      480 gacttcgatg tagtagctcg tgctgctgtt cagatcaaaa atgcgattga tgcaacgatt     540
gaacttggcg agagaattat tgtgttttgg ggtggtcgtg aaggctatat gtctcttctg     600
aacacagatc agaaacgtga aaagaacac cttgcacaga tgttgacgat tgctcgtgac      660
tatgcccgtg cccgtggttt caaaggtact ttcctgatcg aaccgaaacc gatggaaccg     720
actaaacatc aatatgacgt agatacggaa actgtaatcg gcttcctgaa agctcatggt     780
ctggataagg attcaaagt aaatatcgag gtgaatcacg caactttggc aggtcacact     840
ttcgagcatg aattggctgt agctgtagac aatggtatgt gggctcaat tgacgccaat     900 cgtggtgact atcagaatgg ctgggataca gaccaattcc cgatcgacaa ttatgaactg     960
actcaggcta tgatgcagat tatccgtaat ggtggtctcg gtaccggtgg tacgaacttt    1020
gatgctaaaa cccgtcgtaa ttctactgat ctggaagata tctttattgc tcacatcgca    1080
ggtatggacg ctatggcccg tgcactcgaa agtgcagcgg ctctgctcga cgaatctccc    1140
tataagaaga tgctggctga ccgttatgct tcatttgatg ggggcaaagg taaagaattt    1200
gaagacggca agctgactct ggaggatgtg gttgcttatg caaaaacaaa aggcgaaccg    1260
aaacagacta gcggcaagca agaacttat gaggcaattc tgaatatgta ttgctaa       1317

<210> SEQ ID NO 13
<211> LENGTH: 442
<212> TYPE: PRT
<213> ORGANISM: Parabacteroides distasonis

<400> SEQUENCE: 13

Met Ser Tyr Phe Lys Gly Glu Lys Glu Phe Phe Pro Gly Ile Gly Gln
1               5                   10                  15

Ile Gln Phe Glu Gly Arg Glu Ser Lys Asn Pro Leu Ala Phe His Tyr
            20                  25                  30
```

```
Tyr Asp Ala Asp Lys Val Val Met Gly Lys Thr Leu Lys Asp His Leu
         35                  40                  45

Arg Phe Ala Met Ala Tyr Trp His Thr Leu Cys Ala Glu Gly Gly Asp
 50                  55                  60

Gln Phe Gly Gly Gly Thr Lys Thr Phe Pro Trp Asn Asp Ser Thr Asp
 65                  70                  75                  80

Ala Ile Thr Arg Ala Lys Tyr Lys Met Asp Ala Ala Phe Glu Phe Met
                 85                  90                  95

Thr Lys Cys Asn Ile Pro Tyr Tyr Cys Phe His Asp Val Asp Val Val
                100                 105                 110

Asp Glu Ala Pro Thr Leu Gly Glu Phe Glu Lys Arg Leu Gln Thr Met
                115                 120                 125

Val Glu His Ala Lys Glu His Gln Ala Ala Thr Gly Lys Lys Leu Leu
130                 135                 140

Trp Ser Thr Ala Asn Val Phe Gly His Lys Arg Tyr Met Asn Gly Ala
145                 150                 155                 160

Ala Thr Asn Pro Tyr Phe Pro Thr Val Ala Cys Val Gly Thr Gln Ile
                165                 170                 175

Lys Asn Ala Ile Asp Ala Cys Ile Ala Leu Gly Gly Glu Asn Tyr Val
                180                 185                 190

Phe Trp Gly Gly Arg Glu Gly Tyr Met Ser Leu Leu Asn Thr Asn Met
195                 200                 205

Lys Arg Glu Lys Asp His Leu Ala Met Met Leu Thr Met Ala Arg Asp
210                 215                 220

Tyr Gly Arg Lys Asn Gly Phe Lys Gly Thr Phe Leu Ile Glu Pro Lys
225                 230                 235                 240

Pro Met Glu Pro Thr Lys His Gln Tyr Asp Val Asp Ser Glu Thr Val
                245                 250                 255

Ile Gly Phe Leu Arg His Tyr Gly Leu Asp Lys Asp Phe Ala Leu Asn
                260                 265                 270

Ile Glu Val Asn His Ala Thr Leu Ala Gly His Thr Phe Glu His Glu
                275                 280                 285

Leu Gln Ala Ala Ala Asp Ala Gly Met Leu Cys Ser Ile Asp Ala Asn
290                 295                 300

Arg Gly Asp Tyr Gln Asn Gly Trp Asp Thr Asp Gln Phe Pro Met Asp
305                 310                 315                 320

Ile Tyr Glu Leu Ala Gln Ala Trp Leu Val Ile Leu Glu Gly Gly Gly
                325                 330                 335

Leu Thr Thr Gly Gly Thr Asn Phe Asp Ala Lys Thr Arg Arg Asn Ser
                340                 345                 350

Thr Asp Leu Glu Asp Ile Phe Ile Ala His Ile Gly Gly Met Asp Ala
                355                 360                 365

Phe Ala Arg Ala Leu Met Ile Ala Ala Asp Ile Leu Glu Asn Ser Asp
370                 375                 380

Tyr Arg Lys Met Arg Ala Glu Arg Tyr Ala Ser Phe Asp Ala Gly Glu
385                 390                 395                 400

Gly Lys Ala Phe Glu Asp Gly Lys Leu Thr Leu Glu Asp Leu Arg Thr
                405                 410                 415

Ile Ala Leu Arg Asp Gly Glu Pro Lys Gln Ile Ser Gly Lys Gln Glu
                420                 425                 430

Leu Tyr Glu Met Ile Val Asn Leu His Ile
                435                 440
```

<210> SEQ ID NO 14
<211> LENGTH: 1329
<212> TYPE: DNA
<213> ORGANISM: Parabacteroides_distasonis

<400> SEQUENCE: 14

```
atgtcttact ttaagggtga aaagaattc ttcccaggta tcggtcaaat ccaatttgaa      60
ggtagagaat ccaagaaccc attggctttt cattattacg atgccgataa ggttgtcatg     120
ggtaaaactt tgaaggacca tttgagattc gctatggctt attggcatac tttgtgtgct    180
gaaggtggtg atcaatttgg tggtggtaca aaaactttcc catggaatga ttccaccgat    240
gctattacta gagccaagta caaaatggat gctgcttttg aattcatgac caagtgcaac    300
attccttact actgcttcca cgatgttgat gttgttgatg aagctccaac tttgggtgaa    360
ttcgaaaaaa gattgcaaac catggtcgaa catgccaaag aacatcaagc tgctactggt    420
aaaaagttgt tgtggtctac tgctaatgtt tccggtcaca agagatatat gaacggtgct    480
gctactaatc atactttcc aactgttgct tgcgttggta ctcaaatcaa gaatgctatt    540
gatgcttgca ttgctttggg tggtgaaaat tatgttttct ggggtggtag agaaggttac    600
atgtctttgt tgaacaccaa catgaagaga gaaaaggatc atttggccat gatgttgact    660
atggctagag attacggtag aaagaatggt ttcaagggta cttttcttgat cgaacctaaa    720
cctatggaac tactaagca ccaatacgat gttgattccg aaaccgttat cggtttcttg    780
agacattacg gtttggataa ggatttcgcc ttgaacatcg aagttaacca tgctactttg    840
gctggtcata ctttcgaaca tgaattgcaa gctgctgctg atgctggtat gttgtgttct    900
attgatgcta acagaggtga ctaccaaaat ggttgggata ctgatcaatt cccaatggat    960
atctacgaat tggctcaagc ttggttggtt attttggaag tggtggttt gactactggt   1020
ggtactaatt tgatgccaa gaccagaaga aactccactg atttggaaga catcttcatt   1080
gcccatatcg gtgtatgga tgcttttgct agagctttga tgattgctgc cgatatttg   1140
gaaaactccg actacagaaa gatgagagct gaaagatacg cttcttttga tgctggtgaa   1200
ggtaaggctt tcgaagatgg taaattgacc ttggaagatt tgagaaccat tgctttgaga   1260
gatggtgaac ctaagcaaat ttccggtaag caagaattat acgaaatgat cgtcaacttg   1320
cacatctaa                                                         1329
```

<210> SEQ ID NO 15
<211> LENGTH: 437
<212> TYPE: PRT
<213> ORGANISM: Cyllamyces aberensis

<400> SEQUENCE: 15

```
Met Val Lys Glu Tyr Phe Pro Ala Ile Gln Lys Ile Lys Phe Glu Gly
1               5                   10                  15

Lys Asp Ser Lys Asn Pro Met Ala Phe His Tyr Tyr Asp Ala Glu Lys
            20                  25                  30

Glu Ile Met Gly Lys Lys Met Lys Asp Trp Leu Arg Phe Ala Met Ala
        35                  40                  45

Trp Trp His Thr Leu Cys Ala Glu Gly Ser Asp Gln Phe Gly Pro Gly
    50                  55                  60

Thr Lys Thr Phe Pro Trp Asn Glu Gly Thr Asp Pro Ile Glu Lys Ala
65                  70                  75                  80

Lys Gln Lys Val Asp Ala Gly Phe Glu Ile Met Thr Lys Leu Gly Ile
                85                  90                  95
```

```
Glu His Tyr Cys Phe His Asp Val Asp Leu Val Asp Glu Gly Lys Asn
            100                 105                 110
Val Glu Glu Tyr Glu Lys Asn Leu Lys Thr Ile Val Ala Tyr Leu Lys
            115                 120                 125
Glu Lys Gln Lys Glu Thr Gly Ile Lys Leu Leu Trp Ser Thr Ala Asn
130                 135                 140
Val Phe Gly His Lys Arg Tyr Met Asn Gly Ala Ser Thr Asn Pro Asp
145                 150                 155                 160
Phe Asp Val Val Ala Arg Ala Ile Val Gln Ile Lys Asn Ala Met Asp
                165                 170                 175
Ala Gly Ile Glu Leu Gly Ala Glu Asn Tyr Val Phe Trp Gly Gly Arg
            180                 185                 190
Glu Gly Tyr Met Ser Leu Leu Asn Thr Asp Gln Lys Arg Glu Lys Glu
            195                 200                 205
His Met Ala Met Met Leu Gly Leu Ala Arg Asp Tyr Ala Arg Ser Lys
            210                 215                 220
Gly Phe Lys Gly Thr Phe Leu Ile Glu Pro Lys Pro Met Glu Pro Thr
225                 230                 235                 240
Lys His Gln Tyr Asp Val Asp Thr Glu Thr Val Ile Gly Phe Leu Arg
                245                 250                 255
Ala His Gly Leu Asp Lys Asp Phe Lys Ile Asn Ile Glu Val Asn His
            260                 265                 270
Ala Thr Leu Ala Gly His Thr Phe Glu His Glu Leu Ala Cys Ala Val
            275                 280                 285
Asp Ala Gly Met Leu Gly Ser Ile Asp Ala Asn Arg Gly Asp Tyr Gln
            290                 295                 300
Asn Gly Trp Asp Thr Asp Gln Phe Pro Ile Asp Gln Tyr Glu Leu Val
305                 310                 315                 320
Gln Ala Trp Met Glu Ile Ile Arg Gly Gly Phe Thr Thr Gly Gly
                325                 330                 335
Thr Asn Phe Asp Ala Lys Thr Arg Arg Asn Ser Thr Asp Leu Glu Asp
                340                 345                 350
Ile Ile Ile Ala His Ile Ser Gly Met Asp Ala Met Ala Arg Ala Leu
            355                 360                 365
Glu Asn Ala Ala Lys Leu Leu Thr Glu Ser Pro Tyr Lys Lys Met Lys
370                 375                 380
Ala Asp Arg Tyr Ala Ser Phe Asp Ser Gly Met Gly Lys Asp Phe Glu
385                 390                 395                 400
Asp Gly Lys Leu Thr Phe Glu Gln Val Tyr Glu Tyr Gly Lys Lys Val
                405                 410                 415
Asn Glu Pro Lys Gln Thr Ser Gly Lys Gln Glu Leu Tyr Glu Ala Ile
            420                 425                 430
Val Ala Met Tyr Met
            435

<210> SEQ ID NO 16
<211> LENGTH: 1314
<212> TYPE: DNA
<213> ORGANISM: Cyllamyces_aberensis

<400> SEQUENCE: 16
atggttaagg aatacttccc agctatccaa aagatcaagt tcgaaggtaa ggactctaag      60
aacccaatgg ctttccacta ctacgacgct gaaaaggaaa tcatgggtaa gaagatgaag     120
```

```
gactggttga gattcgctat ggcttggtgg cacactttgt gtgctgaagg ttctgaccaa      180
ttcggtccag gtactaagac tttcccatgg aacgaaggta ctgacccaat cgaaaaggct      240
aagcaaaagg ttgacgctgg tttcgaaatc atgactaagt tgggtatcga acactactgt     300
ttccacgacg ttgacttggt tgacgaaggt aagaacgttg aagaatacga aaagaacttg      360
aagactatcg ttgcttactt gaaggaaaag caaaaggaaa ctggtatcaa gttgttgtgg     420
tctactgcta acgttttcgg tcacaagaga tacatgaacg gtgcttctac taacccagac     480
ttcgacgttg ttgctagagc tatcgttcaa atcaagaacg ctatggacgc tggtatcgaa     540
ttgggtgctg aaaactacgt tttctggggt ggtagagaag ttacatgtc tttgttgaac      600 actgaccaaa agagagaaaa ggaacacatg gctatgatgt tgggtttggc tagagactac     660
gctagatcta agggtttcaa gggtactttc ttgatcgaac caaagccaat ggaaccaact     720
aagcaccaat acgacgttga cactgaaact gttatcggtt tcttgagagc tcacggtttg     780
gacaaggact tcaagatcaa catcgaagtt aaccacgcta cttttggctgg tcacactttc     840 gaacacgaat tggcttgtgc tgttgacgct ggtatgttgg ttctatcga cgctaacaga      900 ggtgactacc aaaacggttg ggacactgac caattcccaa tcgaccaata cgaattggtt     960
caagcttgga tggaaatcat cagaggtggt ggtttcacta ctggtggtac taacttcgac    1020
gctaagacta aagaaactc tactgacttg aagacatca tcatcgctca catctctggt     1080
atggacgcta tggctagagc tttggaaaac gctgctaagt tgttgactga atctccatac    1140
aagaagatga aggctgacag atacgcttct ttcgactctg gtatgggtaa ggacttcgaa    1200
gacggtaagt tgactttcga acaagtttac gaataccgta gaaggttaa cgaaccaaag    1260 caaacttctg gtaagcaaga attgtacgaa gctatcgttg ctatgtacat gtga          1314
```

<210> SEQ ID NO 17
<211> LENGTH: 440
<212> TYPE: PRT
<213> ORGANISM: Abiotrophia defectiva

<400> SEQUENCE: 17

```
Met Ser Glu Leu Phe Gln Asn Ile Pro Lys Ile Lys Tyr Glu Gly Ala
1               5                   10                  15

Asn Ser Lys Asn Pro Leu Ala Phe His Tyr Tyr Asp Ala Glu Lys Ile
            20                  25                  30

Val Leu Gly Lys Thr Met Lys Glu His Leu Pro Phe Ala Met Ala Trp
        35                  40                  45

Trp His Asn Leu Cys Ala Ala Gly Thr Asp Met Phe Gly Arg Asp Thr
    50                  55                  60

Ala Asp Lys Ser Phe Gly Leu Glu Lys Gly Ser Met Glu His Ala Lys
65                  70                  75                  80

Ala Lys Val Asp Ala Gly Phe Glu Phe Met Glu Lys Leu Gly Ile Lys
                85                  90                  95

Tyr Phe Cys Phe His Asp Val Asp Leu Val Pro Glu Ala Cys Asp Ile
            100                 105                 110

Lys Glu Thr Asn Ser Arg Leu Asp Glu Ile Ser Asp Tyr Ile Leu Glu
        115                 120                 125

Lys Met Lys Gly Thr Asp Ile Lys Cys Leu Trp Gly Thr Ala Asn Met
    130                 135                 140

Phe Ser Asn Pro Arg Phe Val Asn Gly Ala Gly Ser Thr Asn Ser Ala
145                 150                 155                 160

Asp Val Tyr Cys Phe Ala Ala Ala Gln Ile Lys Lys Ala Leu Asp Ile
```

|  |  |  | 165 |  |  |  | 170 |  |  |  | 175 |  |
|---|---|---|---|---|---|---|---|---|---|---|---|---|
| Thr | Val | Lys | Leu | Gly | Gly | Arg | Gly | Tyr | Val | Phe | Trp | Gly | Gly | Arg | Glu |
|  |  |  | 180 |  |  |  | 185 |  |  |  | 190 |  |

Gly Tyr Glu Thr Leu Leu Asn Thr Asp Val Lys Phe Glu Gln Glu Asn
    195                    200                   205

Ile Ala Asn Leu Met Lys Met Ala Val Glu Tyr Gly Arg Ser Ile Gly
210                    215                    220

Phe Lys Gly Asp Phe Tyr Ile Glu Pro Lys Pro Lys Glu Pro Met Lys
225                    230                    235                    240

His Gln Tyr Asp Phe Asp Ala Ala Thr Ala Ile Gly Phe Leu Arg Gln
                245                    250                    255

Tyr Gly Leu Asp Lys Asp Phe Lys Leu Asn Ile Glu Ala Asn His Ala
                260                    265                    270

Thr Leu Ala Gly His Ser Phe Gln His Glu Leu Arg Ile Ser Ser Ile
                275                    280                    285

Asn Gly Met Leu Gly Ser Val Asp Ala Asn Gln Gly Asp Met Leu Leu
                290                    295                    300

Gly Trp Asp Thr Asp Glu Phe Pro Phe Asp Val Tyr Asp Thr Thr Met
305                    310                    315                    320

Cys Met Tyr Glu Val Leu Lys Asn Gly Gly Leu Thr Gly Gly Phe Asn
                325                    330                    335

Phe Asp Ala Lys Asn Arg Arg Pro Ser Tyr Thr Tyr Glu Asp Met Phe
                340                    345                    350

Tyr Gly Phe Ile Leu Gly Met Asp Ser Phe Ala Leu Gly Leu Ile Lys
                355                    360                    365

Ala Ala Lys Leu Ile Glu Glu Gly Thr Leu Asp Asn Phe Ile Lys Glu
                370                    375                    380

Arg Tyr Lys Ser Phe Glu Ser Glu Ile Gly Lys Lys Ile Arg Ser Lys
385                    390                    395                    400

Ser Ala Ser Leu Gln Glu Leu Ala Ala Tyr Ala Glu Glu Met Gly Ala
                405                    410                    415

Pro Ala Met Pro Gly Ser Gly Arg Gln Glu Tyr Leu Gln Ala Ala Leu
                420                    425                    430

Asn Gln Asn Leu Phe Gly Glu Val
                435                    440

```
<210> SEQ ID NO 18
<211> LENGTH: 1323
<212> TYPE: DNA
<213> ORGANISM: Abiotrophia defectiva

<400> SEQUENCE: 18
atgtctgaat tgttccaaaa catcccaaag atcaagtacg aaggtgctaa ctctaagaac      60
ccattggctt tccactacta cgacgctgaa aagatcgttt tgggtaagac tatgaaggaa     120
cacttgccat tcgctatggc ttggtggcac aacttgtgtg ctgctggtac tgacatgttc     180
ggtagagaca ctgctgacaa gtctttcggt ttggaaaagg ttctatgga acacgctaag     240 gctaaggttg acgctggttt cgaattcatg gaaaagttgg gtatcaagta cttctgtttc     300
cacgacgttg acttggttcc agaagcttgt gacatcaagg aaactaactc tagattggac     360
gaaatctctg actacatctt ggaaaagatg aagggtactg acatcaagtg tttgtggggt     420
actgctaaca tgttctctaa cccaagattc gttaacggtg ctggttctac taactctgct     480
gacgtttact gtttcgctgc tgctcaaatc aagaaggctt tggacatcac tgttaagttg     540
```

-continued

```
ggtggtagag gttacgtttt ctggggtggt agagaaggtt acgaaacttt gttgaacact      600
gacgttaagt tcgaacaaga aaacatcgct aacttgatga agatggctgt tgaatacggt      660
agatctatcg gtttcaaggg tgacttctac atcgaaccaa agccaaagga accaatgaag      720
caccaatacg acttcgacgc tgctactgct atcggtttct tgagacaata cggtttggac      780
aaggacttca agttgaacat cgaagctaac cacgctactt tggctggtca ctcttttccaa     840 cacgaattga gaatctcttc tatcaacggt atgttgggtt ctgttgacgc taaccaaggt      900
gacatgttgt tgggttggga cactgacgaa ttcccattcg acgtttacga cactactatg      960
tgtatgtacg aagttttgaa gaacggtggt ttgactggtg gtttcaactt cgacgctaag     1020
aacagaagac catcttacac ttacgaagac atgttctacg gtttcatctt gggtatggac     1080
tctttcgctt gggtttgat caaggctgct aagttgatcg aagaaggtac tttgacaaac      1140
ttcatcaagg aaagatacaa gtctttcgaa tctgaaatcg gtaagaagat cagatctaag     1200
tctgcttctt tgcaagaatt ggctgcttac gctgaagaaa tgggtgctcc agctatgcca     1260
ggttctggta gacaagaata cttgcaagct gctttgaacc aaaacttgtt cggtgaagtt     1320
tga                                                                  1323
```

<210> SEQ ID NO 19
<211> LENGTH: 442
<212> TYPE: PRT
<213> ORGANISM: Uncultured bacterium XYM2

<400> SEQUENCE: 19

```
Met Lys Leu Thr Val Gly Asp Lys Glu Tyr Phe Lys Gly Ile Lys Pro
1               5                   10                  15

Ile Lys Phe Glu Gly Lys Asp Ser Asp Asn Pro Leu Ala Phe Lys Tyr
            20                  25                  30

Tyr Asn Pro Ser Gln Lys Val Gly Lys Lys Thr Met Glu Glu His Phe
        35                  40                  45

Arg Phe Ala Ile Ala Tyr Trp His Thr Phe Cys Gly Thr Gly Gly Asp
    50                  55                  60

Pro Phe Gly Pro Gly Thr Lys Thr Phe Pro Trp Leu Gln Asn Ser Asp
65                  70                  75                  80

Ala Val Gln Arg Ala Tyr Asp Lys Met Asp Ala Ala Phe Glu Phe Ile
                85                  90                  95

Thr Lys Ile Gly Ala Pro Phe Tyr Cys Phe His Asp Tyr Asp Leu Val
            100                 105                 110

Asp Glu Gly Pro Thr Leu Lys Glu Ser Glu Ser Arg Leu Gln Lys Val
        115                 120                 125

Val Asp Tyr Ala Lys Lys Gln Lys Ala Ser Gly Val Lys Leu Leu
    130                 135                 140

Trp Gly Thr Ala Asn Leu Phe Ser His Pro Arg Tyr Met Asn Gly Ala
145                 150                 155                 160

Ala Thr Asn Pro Asp Phe Asp Val Val Cys Tyr Ala Ala Ser Gln Val
                165                 170                 175

Lys Asn Ala Leu Asp Ala Thr Ile Ala Leu Gly Gly Ala Asn Tyr Val
            180                 185                 190

Phe Trp Gly Gly Arg Glu Gly Tyr Met Ser Leu Leu Asn Thr Asn Met
        195                 200                 205

Lys Arg Glu Gln Glu His Met Ala Lys Phe Leu His Met Ala Lys Asp
    210                 215                 220

Tyr Ala Arg Ala Asn Gly Phe Lys Gly Thr Phe Phe Ile Glu Pro Lys
```

| | | | | | | | | 225 | | | | | 230 | | | | | 235 | | | | | 240 |
|---|---|---|---|---|---|---|---|---|---|---|---|---|---|---|---|---|---|---|---|---|---|---|---|
Pro Met Glu Pro Ser Lys His Gln Tyr Asp Phe Asp Ser Ala Thr Val
                        245                              250                        255

Ile Gly Phe Leu Arg Gln Phe Asp Leu Leu Gly Asp Phe Lys Leu Asn
                        260                              265                        270

Ile Glu Val Asn His Ala Thr Leu Ala His His Thr Phe Gln His Glu
                  275                              280                          285

Leu Gln Val Ala Ala Asp Ala Gly Ala Leu Gly Ser Ile Asp Ala Asn
          290                            295                              300

Arg Gly Asp Tyr Gln Asn Gly Trp Asp Thr Asp Gln Phe Pro Asn Asn
305                        310                              315                        320

Leu Tyr Glu Leu Ala Glu Ser Met Leu Val Ile Leu Glu Ala Gly Gly
                  325                              330                        335

Phe Lys Ser Gly Gly Val Asn Phe Asp Ala Lys Thr Arg Arg Asn Ser
                        340                              345                        350

Thr Asp Leu Val Asp Ile Phe His Ala His Ile Gly Gly Met Asp Thr
                  355                              360                          365

Phe Ala Arg Ser Leu Leu Ile Ala Gln Ala Val Leu Asp Asn Gly Glu
          370                            375                              380

Tyr Thr Lys Ile Arg Lys Asp Arg Tyr Ser Ser Phe Asp Ser Gly Lys
385                        390                              395                        400

Gly Lys Gln Phe Asp Gln Gly Lys Leu Ser Leu Glu Asp Leu Arg Asn
                        405                              410                        415

Leu Ala His Lys Ala Gly Glu Pro Lys Gln Leu Ser Gly Lys Gln Glu
          420                            425                              430

Tyr Ile Glu Asn Leu Ile Ser Arg Phe Ile
         435                            440

<210> SEQ ID NO 20
<211> LENGTH: 1329
<212> TYPE: DNA
<213> ORGANISM: Uncultured bacterium XYM2

<400> SEQUENCE: 20

```
atgaagttga ccgttggtga caaagaatac ttcaagggta ttaagccaat caagttcgaa    60
ggtaaggatt ccgataatcc attggctttc aagtactaca acccatctca aaaggttggt   120
aaaaagacca tggaagaaca tttcagattc gctattgctt actggcatac tttttgtggt   180
actggtggtg atccatttgg tccaggtaca aaaacttttc catggttgca aaactccgat   240
gctgttcaaa gagcttacga taagatggat gctgcctttg aattcattac aaaaattggt   300
gctccattct actgcttcca tgattacgat ttggttgatg aaggtccaac cttgaaagaa   360
tccgaatcca gattgcaaaa ggtcgttgat tacgctaaga aaaagcaaaa agcctccggt   420
gttaagttgt tgtggggtac tgctaatttg ttctcccatc aagatatat gaatggtgct   480
gctacaaacc agatttcga tgttgtttgt tatgctgcct ctcaagttaa gaatgctttg   540
gatgctacta ttgctttggg tggtgctaat tatgtttttt ggggtggtag agaaggttac   600
atgtctttgt tgaacaccaa catgaagaga gaacaagaac atatggctaa gttcttgcat   660
atggccaagg attatgctag agctaatggt tttaagggta cttctcttcat cgaacctaaa   720
cctatggaac catctaagca ccaatacgat tttgattccg ctaccgttat ggtttcttg   780
agacaatttg atttgttggg tgacttcaag ttgaacatcg aagttaacca tgctaccttg   840
gctcatcata cctttcaaca tgaattgcaa gttgctgctg atgctggtgc tttaggttct   900
```

-continued

```
attgatgcta atagaggtga ctaccaaaac ggttgggata ctgatcaatt tccaaacaac    960
ttgtacgaat tggccgaatc catgttggtt attttggaag ctggtggttt taaatccggt   1020
ggtgttaatt tcgatgctaa gaccagaaga aactctaccg atttggtcga tattttccat   1080
gctcatattg gtggtatgga tacctttgct agatccttgt tgattgctca agctgttttg   1140
gataatggtg aatacaccaa gatcagaaag gacagatact cctctttcga ttctggtaaa   1200
ggtaagcaat tcgatcaagg taaattgtcc ttggaagatt tgagaaactt ggctcacaaa   1260
gctggtgaac taagcaatt gtctggtaag caagaatata tcgaaaactt gatctccaga   1320
ttcatttga                                                           1329
```

<210> SEQ ID NO 21
<211> LENGTH: 442
<212> TYPE: PRT
<213> ORGANISM: Chitinophaga pinensis

<400> SEQUENCE: 21

```
Met Ser Ile Thr Leu Gly Asn Gln Glu Tyr Phe Lys Gly Ile Gly Lys
1               5                  10                  15

Ile Ala Tyr Glu Gly Pro Gln Ser Thr Asn Pro Phe Ala Tyr Lys Trp
            20                  25                  30

Tyr Asp Glu Asn Arg Lys Ile Gly Gly Lys Thr Met Lys Glu Leu Phe
        35                  40                  45

Arg Phe Ala Val Ser Tyr Trp His Thr Phe Cys Gly Thr Gly Gly Asp
    50                  55                  60

Pro Phe Gly Pro Gly Thr Lys Ala Phe Pro Trp Leu Thr Ala Thr Asp
65                  70                  75                  80

Ala Val Gln Ser Ala Lys Asp Lys Met Asp Ala Ala Phe Glu Phe Phe
                85                  90                  95

Thr Lys Leu Gly Val Pro Tyr Tyr Cys Phe His Asp Val Asp Leu Val
            100                 105                 110

Asp Glu Gly Ala Ser Ile Ser Glu Tyr Glu Ser Arg Met Gln Gln Ile
        115                 120                 125

Val Glu Tyr Ala Lys Glu Lys Gln Lys Ala Ser Gly Val Lys Leu Leu
    130                 135                 140

Trp Gly Thr Ala Asn Val Phe Ser Asn Pro Arg Tyr Met Asn Gly Ala
145                 150                 155                 160

Ala Thr Asn Pro Asp Phe Ala Val Ala Tyr Ala Gly Thr Gln Val
                165                 170                 175

Lys Asn Ser Leu Asp Ala Thr Ile Ala Leu Gly Gly Glu Asn Tyr Val
            180                 185                 190

Phe Trp Gly Gly Arg Glu Gly Tyr Met Thr Leu Leu Asn Thr Asp Met
        195                 200                 205

Lys Arg Glu Gln Glu His Leu Ala Arg Phe Leu Thr Met Ala Lys Asp
    210                 215                 220

Tyr Ala Arg Lys Gln Gly Phe Thr Gly Thr Phe Phe Ile Glu Pro Lys
225                 230                 235                 240

Pro Cys Glu Pro Thr Lys His Gln Tyr Asp Tyr Asp Ala Ala Thr Val
                245                 250                 255

Ile Gly Phe Leu Arg His Phe Gly Leu Asp Lys Asp Phe Lys Leu Asn
            260                 265                 270

Leu Glu Val Asn His Ala Thr Leu Ala Gly His Thr Phe Gln His Glu
        275                 280                 285

Leu Gln Val Ala Ala Asp Ala Gly Met Leu Gly Ser Ile Asp Ala Asn
```

```
                290                 295                 300
Arg Gly Asp Ala Gln Asn Gly Trp Asp Thr Asp Gln Phe Pro Met Asn
305                 310                 315                 320

Leu Asn Asp Met Val Glu Phe Met Leu Val Ile Leu Glu Ala Gly Gly
                325                 330                 335

Phe Ser Gly Gly Gly Val Asn Phe Asp Ala Lys Thr Arg Arg Asn Ser
                340                 345                 350

Thr Asp Leu Glu Asp Ile Phe His Ala His Ile Gly Gly Ile Asp Ser
            355                 360                 365

Phe Ala Arg Ala Ala Val Ile Ala Glu Lys Val Leu Glu Gln Ser Pro
        370                 375                 380

Tyr Lys Gln Phe Arg Lys Asp Arg Tyr Ala Ser Phe Asp Ser Gly Lys
385                 390                 395                 400

Gly Lys Asp Phe Glu Ala Gly Thr Leu Thr Leu Glu Asp Leu Arg Ser
                405                 410                 415

Phe Ala Val Ser Asn Gly Glu Pro Lys His Ile Ser Gly Lys Gln Glu
                420                 425                 430

Trp Leu Glu Asn Ile Ile Asn Gln Tyr Ile
            435                 440

<210> SEQ ID NO 22
<211> LENGTH: 1329
<212> TYPE: DNA
<213> ORGANISM: Chitinophaga pinensis

<400> SEQUENCE: 22
atgtccatca ccttgggtaa tcaagaatac ttcaagggta ttggtaagat tgcttacgaa      60
ggtccacaat ctactaatcc atttgcttac aagtggtacg acgaaaacag aaaaattggt     120
ggtaagacca tgaaggaatt attcagattc gctgtttcct actggcatac ttttttgtgg     180
actggtggtg atccatttgg tccaggtaca aaagcttttc catggttgac tgctactgat     240
gctgttcaat ctgctaagga taagatggat gctgcttttg aattcttcac caaattgggt     300
gttccttact actgcttcca cgatgttgat ttggttgatg aaggtgcttc catttctgaa     360
tacgaatcca gaatgcaaca aatcgtcgaa tacgccaaag aaaagcaaaa agcttccggt     420
gttaagttgt tgtggggtac tgctaatgtt ttctccaacc caagatatat gaacggtgct     480
gctactaatc cagattttgc tgctgttgct tatgctggta tcaagttaa gaactctttg     540 gatgctacca ttgctttggg tggtgaaaat tatgttttct ggggtggtag agaaggttac     600
atgactttgt tgaacaccga catgaagaga gaacaagaac atttggctag attcttgacc     660
atggctaaag attacgctag aaagcaaggt ttcaccggta cttttttcat tgaacctaag     720
ccatgcgaac tactaccaaca tcaatatgat tacgatgctg ccaccgttat tggtttttg     780 agacatttcg gtttggacaa ggacttcaag ttgaacttgg aagttaacca tgctactttg     840
gctggtcata ctttccaaca cgaattgcaa gttgctgctg atgctggtat gttgggttct     900
attgatgcta atagaggtga tgctcaaaac ggttgggata ctgatcaatt ccaatgaac     960 ttgaacgaca tggtcgaatt catgttggtt attttggaag ctggtggttt ttctggtggt    1020
ggtgttaatt ttgatgccaa gactagaaga aactccaccg atttggaaga tatttccat    1080 gctcatatcg gtggtattga ttcttttgct agagctgctg ttatcgctga aaaggttttg    1140
gaacaatccc catacaagca attcagaaag gatagatacg cttctttcga ttctggtaag    1200
ggtaaggatt ttgaagctgg tactttgacc ttggaagatt tgagatcttt cgctgttct    1260
```

-continued

```
aacggtgaac ctaaacatat ttccggtaag caagaatggt tggaaaacat catcaatcag    1320
tatatctaa                                                            1329
```

<210> SEQ ID NO 23
<211> LENGTH: 439
<212> TYPE: PRT
<213> ORGANISM: Prevotella ruminicola

<400> SEQUENCE: 23

```
Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Glu Thr
            100                 105                 110

Ile Ala Glu Tyr Glu Arg Arg Met Lys Glu Ile Thr Asp Tyr Ala Leu
        115                 120                 125

Val Lys Met Lys Glu Tyr Pro Asn Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Cys Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Asn Gly Met Leu Gly Ser Ile Asp Ala Asn Arg Gly Asp Ala
    290                 295                 300

Gln Asn Gly Trp Asp Thr Asp Gln Phe Pro Ile Asp Asn Phe Glu Leu
305                 310                 315                 320

Thr Gln Ala Met Leu Glu Ile Ile Arg Asn Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
```

```
                355                 360                 365
Leu Met Asn Ala Ala Ile Leu Glu Glu Ser Glu Leu Pro Lys Met
        370                 375                 380

Lys Lys Glu Arg Tyr Ala Ser Phe Asp Asn Gly Ile Gly Lys Asp Phe
385                 390                 395                 400

Glu Asp Gly Lys Leu Thr Leu Glu Gln Ala Tyr Glu Tyr Gly Lys Lys
                405                 410                 415

Val Glu Glu Pro Lys Gln Thr Ser Gly Lys Gln Glu Lys Tyr Glu Thr
            420                 425                 430

Thr Val Ala Leu Tyr Cys Lys
            435

<210> SEQ ID NO 24
<211> LENGTH: 1320
<212> TYPE: DNA
<213> ORGANISM: Prevotella ruminicola

<400> SEQUENCE: 24
atggctaagg aatacttccc attcactggt aagatcccat cgaaggtaa ggactctaag       60
aacgttatgg ctttccacta ctacgaacca gaaaaggttg ttatgggtaa gaagatgaag     120
gactggttga agttcgctat ggcttggtgg cacactttgg gtggtgcttc tgctgaccaa     180
ttcggtggtc aaactagatc ttacgaatgg gacaaggctg ctgacgctgt tcaaagagct     240
aaggacaaga tggacgctgg tttcgaaatc atggacaagt gggtatcga atacttctgt     300
ttccacgacg ttgacttggt tgaagaaggt gaaactatcg ctgaatacga agaagaatg      360
aaggaaatca ctgactacgc tttggttaag atgaaggaat acccaaacat caagttgttg     420
tggggtactg ctaacgtttt cggtaacaag agatacgcta acggtgcttc tactaaccca     480
gacttcgacg ttgttgctag agctatcgtt caaatcaaga acgctatcga cgctactatc     540
aagttgggtg gtactaacta cgttttctgg ggtggtagag aaggttacat gtctttgttg     600
aacactgacc aaaagagaga aaaggaacac atggctacta tgttgactat ggctagagac     660
tacgctagag ctaagggttt caagggtact ttcttgatcg aaccaaagcc aatggaacca     720
tctaagcacc aatacgacgt tgacactgaa actgtttgtg gtttcttgag agctcacggt     780
ttggacaagg acttcaaggt taacatcgaa gttaaccacg ctactttggc tggtcacact     840
ttcgaacacg aattggcttg tgctgttgac aacggtatgt tgggttctat cgacgctaac     900
agaggtgacg ctcaaaacgg ttgggacact gaccaattcc caatcgacaa cttcgaattg     960
actcaagcta tgttggaaat catcagaaac ggtggtttgg gtaacggtgg tactaacttc    1020
gacgctaaga tcagaagaaa ctctactgac ttggaagact tgttcatcgc tcacatctct    1080
ggtatggacg ctatggctag agctttgatg aacgctgctg ctatcttgga agaatctgaa    1140
ttgccaaaga tgaagaagga agatacgct tctttcgaca acggtatcgg taaggacttc    1200
gaagacggta agttgacttt ggaacaagct tacgaatacg gtaagaaggt tgaagaacca    1260
aagcaaactt ctggtaagca agaaaagtac gaaactactg ttgctttgta ctgtaagtga    1320

<210> SEQ ID NO 25
<211> LENGTH: 438
<212> TYPE: PRT
<213> ORGANISM: Artificial Sequence
<220> FEATURE:
<223> OTHER INFORMATION: CX386 chimeric xylose isomerase

<400> SEQUENCE: 25
```

-continued

```
Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Glu Pro Glu Lys
            20                  25                  30

Val Val Met Gly Lys Lys Met Lys Asp Trp Leu Lys Phe Ala Met Ala
            35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Glu Thr
                100                 105                 110

Ile Ala Glu Tyr Glu Arg Arg Met Lys Glu Ile Thr Asp Tyr Ala Leu
            115                 120                 125

Val Lys Met Lys Glu Tyr Pro Asn Ile Lys Leu Leu Trp Gly Thr Ala
    130                 135                 140

Asn Val Phe Ser Asn Pro Arg Tyr Met Asn Gly Ala Ala Thr Asn Pro
145                 150                 155                 160

Asp Phe Ala Ala Val Ala Tyr Ala Gly Thr Gln Val Lys Asn Ser Leu
                165                 170                 175

Asp Ala Thr Ile Ala Leu Gly Gly Glu Asn Tyr Val Phe Trp Gly Gly
            180                 185                 190

Arg Glu Gly Tyr Met Ser Leu Leu Asn Thr Asn Met Lys Arg Glu Lys
    195                 200                 205

Asp His Leu Ala Met Met Leu Thr Met Ala Arg Asp Tyr Gly Arg Lys
    210                 215                 220

Asn Gly Phe Lys Gly Thr Phe Leu Ile Glu Pro Lys Pro Met Glu Pro
225                 230                 235                 240

Thr Lys His Gln Tyr Asp Val Asp Ser Glu Thr Val Ile Gly Phe Leu
            245                 250                 255

Arg His Tyr Gly Leu Asp Lys Asp Phe Ala Leu Asn Ile Glu Val Asn
            260                 265                 270

His Ala Thr Leu Ala Gly His Thr Phe Glu His Glu Leu Gln Ala Ala
    275                 280                 285

Ala Asp Ala Gly Met Leu Cys Ser Ile Asp Ala Asn Arg Gly Asp Tyr
    290                 295                 300

Gln Asn Gly Trp Asp Thr Asp Gln Phe Pro Met Asp Ile Tyr Glu Leu
305                 310                 315                 320

Ala Gln Ala Trp Leu Val Ile Leu Glu Gly Gly Gly Leu Thr Thr Gly
            325                 330                 335

Gly Thr Asn Phe Asp Ala Lys Thr Arg Arg Asn Ser Thr Asp Leu Glu
            340                 345                 350

Asp Ile Phe Ile Ala His Ile Gly Gly Met Asp Ala Phe Ala Arg Ala
            355                 360                 365

Leu Met Ile Ala Ala Asp Ile Leu Glu Asn Ser Asp Tyr Arg Lys Met
    370                 375                 380

Arg Ala Glu Arg Tyr Ala Ser Phe Asp Ala Gly Glu Gly Lys Ala Phe
385                 390                 395                 400

Glu Asp Gly Lys Leu Thr Leu Glu Asp Leu Arg Thr Ile Ala Leu Arg
            405                 410                 415

Asp Gly Glu Pro Lys Gln Ile Ser Gly Lys Gln Glu Leu Tyr Glu Met
```

Ile Val Asn Leu His Ile
        435

<210> SEQ ID NO 26
<211> LENGTH: 1317
<212> TYPE: DNA
<213> ORGANISM: Artificial Sequence
<220> FEATURE:
<223> OTHER INFORMATION: CX386 chimeric xylose isomerase

<400> SEQUENCE: 26

```
atggctaagg aatacttccc attcactggt aagatcccat tcgaaggtaa ggactctaag      60
aacgttatgg ctttccacta ctacgaacca gaaaaggttg ttatgggtaa gaagatgaag     120
gactggttga agttcgctat ggcttggtgg cacactttgg gtggtgcttc tgctgaccaa     180
ttcggtggtc aaactagatc ttacgaatgg acaaggctg ctgacgctgt tcaaagagct      240
aaggacaaga tggacgctgg tttcgaaatc atggacaagt tgggtatcga atacttctgt     300
tccacgacg ttgacttggt tgaagaaggt gaaactatcg ctgaatacga agaagaatg       360
aaggaaatca ctgactacgc tttggttaag atgaaggaat acccaaacat caagttgttg     420
tggggtactg ctaatgtttt ctccaaccca agatatatga acggtgctgc tactaatcca     480
gattttgctg ctgttgctta tgctggtact caagttaaga actctttgga tgctaccatt     540
gctttgggtg gtgaaaatta tgttttctgg ggtggtagag aaggttacat gtctttgttg     600
aacaccaaca tgaagagaga aaaggatcat ttggccatga tgttgactat ggctagagat     660
tacggtagaa agaatggttt caagggtact ttcttgatcg aacctaaacc tatggaacct     720
actaagcacc aatacgatgt tgattccgaa accgttatcg gtttcttgag acattacggt     780
ttggataagg atttcgcctt gaacatcgaa gttaaccatg ctactttggc tggtcatact     840
ttcgaacatg aattgcaagc tgctgctgat gctggtatgt tgtgttctat tgatgctaac     900
agaggtgact accaaaatgg ttgggatact gatcaattcc caatggatat ctacgaattg     960
gctcaagctt ggttggttat tttgaaggt ggtggtttga ctactggtgg tactaatttt    1020
gatgccaaga ccagaagaaa ctccactgat ttggaagaca tcttcattgc ccatatcggt    1080
ggtatggatg ctttgctag agctttgatg attgctgccg atattttga aaactccgac     1140
tacagaaaga tgagagctga agatacgct tcttttgatg ctggtgaagg taaggctttc     1200
gaagatggta aattgacctt ggaagatttg agaaccattg ctttgagaga tggtgaacct    1260
aagcaaattt ccggtaagca agaattatac gaaatgatcg tcaacttgca catctaa       1317
```

<210> SEQ ID NO 27
<211> LENGTH: 438
<212> TYPE: PRT
<213> ORGANISM: Artificial Sequence
<220> FEATURE:
<223> OTHER INFORMATION: CX1224 chimeric xylose isomerase

<400> SEQUENCE: 27

Met Thr Lys Glu Tyr Phe Pro Phe Thr Gly Lys Ile Pro Tyr Glu Gly
1               5                   10                  15

Lys Asp Ser Asn Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln

```
            50                  55                  60
Thr Arg Ser Tyr Glu Trp Asp Lys Ala Ala Asp Ala Val Gln Arg Ala
 65                  70                  75                  80

Lys Asp Lys Met Asp Ala Gly Phe Glu Ile Met Asp Lys Leu Gly Ile
                 85                  90                  95

Glu Tyr Phe Cys Phe His Asp Val Asp Leu Val Glu Glu Gly Glu Thr
            100                 105                 110

Ile Ala Glu Tyr Glu Arg Arg Met Lys Glu Ile Thr Asp Tyr Ala Leu
        115                 120                 125

Val Lys Met Lys Glu Tyr Pro Asn Ile Lys Leu Leu Trp Gly Thr Ala
130                 135                 140

Asn Val Phe Ser Asn Pro Arg Tyr Met Asn Gly Ala Ala Thr Asn Pro
145                 150                 155                 160

Asp Phe Ala Ala Val Ala Tyr Ala Gly Thr Gln Val Lys Asn Ser Leu
                165                 170                 175

Asp Ala Thr Ile Ala Leu Gly Gly Glu Asn Tyr Val Phe Trp Gly Gly
            180                 185                 190

Arg Glu Gly Tyr Met Ser Leu Leu Asn Thr Asn Met Lys Arg Glu Lys
        195                 200                 205

Asp His Leu Ala Met Met Leu Thr Met Ala Arg Asp Tyr Gly Arg Lys
210                 215                 220

Asn Gly Phe Lys Gly Thr Phe Leu Ile Glu Pro Lys Pro Met Glu Pro
225                 230                 235                 240

Thr Lys His Gln Tyr Asp Val Asp Ser Glu Thr Val Ile Gly Phe Leu
                245                 250                 255

Arg His Tyr Gly Leu Asp Lys Asp Phe Ala Leu Asn Ile Glu Val Asn
            260                 265                 270

His Ala Thr Leu Ala Gly His Thr Phe Glu His Glu Leu Gln Ala Ala
        275                 280                 285

Ala Asp Ala Gly Met Leu Cys Ser Ile Asp Ala Asn Arg Gly Asp Tyr
290                 295                 300

Gln Asn Gly Trp Asp Thr Asp Gln Phe Pro Met Asp Ile Tyr Glu Leu
305                 310                 315                 320

Ala Gln Ala Trp Leu Val Ile Leu Glu Asn Gly Gly Leu Thr Thr Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Gly Gly Met Asp Ala Phe Ala Arg Ala
        355                 360                 365

Leu Met Ile Ala Ala Asp Ile Leu Glu Asn Ser Asp Tyr Arg Lys Met
370                 375                 380

Arg Ala Glu Arg Tyr Gly Thr Phe Asp Ala Gly Glu Gly Lys Ala Phe
385                 390                 395                 400

Glu Glu Gly Gln Leu Thr Leu Glu Asp Leu Arg Thr Ile Ala Leu Arg
                405                 410                 415

Asp Gly Asp Pro Lys Lys Ile Ser Gly Lys Gln Glu Leu Tyr Glu Met
            420                 425                 430

Ile Val Asn Leu His Ile
        435

<210> SEQ ID NO 28
<211> LENGTH: 1317
<212> TYPE: DNA
<213> ORGANISM: Artificial Sequence
```

<220> FEATURE:
<223> OTHER INFORMATION: CX1224 chimeric xylose isomerase

<400> SEQUENCE: 28

```
atgactaagg aatacttccc attcactggt aagatcccat acgaaggtaa ggactctaat      60
aacgttatgg ctttccacta ctacgaacca gaaaaggttg ttatgggtaa gaagatgaag     120
gactggttga agttcgctat ggcttggtgg cacactttgg gtggtgcttc tgctgaccaa     180
ttcggtggtc aaactagatc ttacgaatgg gacaaggctg ctgacgctgt tcaaagagct     240
aaggacaaga tggacgctgg tttcgaaatc atggacaagt tgggtatcga atacttctgt     300
ttccacgacg ttgacttggt tgaagaaggt gaaactatcg ctgaatacga agaagaatg      360
aaggaaatca ctgactacgc tttggttaag atgaaggaat acccaaacat caagttgttg     420
tggggtactg ctaatgtttt ctccaaccca agatatatga acggtgctgc tactaatcca     480
gattttgctg ctgttgctta tgctggtact caagttaaga actctttgga tgctaccatt     540
gctttgggtg gtgaaaatta tgttttctgg ggtggtagag aaggttacat gtctttgttg     600
aacaccaaca tgaagagaga aaaggatcat ttggccatga tgttgactat ggctagagat     660
tacggtagaa agaatggttt caagggtact ttcttgatcg aacctaaacc tatggaacct     720
actaagcacc aatacgatgt tgattccgaa accgttatcg gtttcttgag acattacggt     780
ttggataagg atttcgcctt gaacatcgaa gttaaccatg ctactttggc tggtcatact     840
ttcgaacatg aattgcaagc tgctgctgat gctggtatgt tgtgttctat tgatgctaac     900
agaggtgact accaaaatgg ttgggatact gatcaattcc caatggatat ctacgaattg     960
gctcaagctt ggttggttat tttggaaaac ggtggtttga ctactggtgg tactaatttt    1020
gatgccaaga ccagaagaaa ctccactgat ttggaagaca tcttcattgc ccatatcggt    1080
ggtatggatg cttttgctag agctttgatg attgctgccg atattttgga aaactccgac    1140
tacagaaaga tgagagctga aagatacggt acttttgatg ctggtgaagg taaggctttc    1200
gaagaaggtc aattgacctt ggaagatttg agaaccattg ctttgagaga tggtgatcct    1260
aagaagattt ccggtaagca agaattatac gaaatgatcg tcaacttgca catctaa       1317
```